US009968478B2

(12) United States Patent
Taylor et al.

(10) Patent No.: US 9,968,478 B2
(45) Date of Patent: May 15, 2018

(54) APPARATUS AND METHODS FOR BONE REPAIR PREPARATION

(71) Applicant: Conventus Orthopaedics, Inc., Maple Grove, MN (US)

(72) Inventors: Kyle Taylor, Brooklyn Park, MN (US); Todd A. Krinke, Buffalo, MN (US); Alex A. Peterson, Maple Grove, MN (US); Michael P. Brenzel, St. Paul, MN (US); Paul Hindrichs, Plymouth, MN (US)

(73) Assignee: Coventus Orthopaedics, Inc., Maple Grove, MN (US)

( * ) Notice: Subject to any disclaimer, the term of this patent is extended or adjusted under 35 U.S.C. 154(b) by 0 days. days.

(21) Appl. No.: 15/056,918

(22) Filed: Feb. 29, 2016

(65) Prior Publication Data
US 2016/0175012 A1    Jun. 23, 2016

Related U.S. Application Data

(63) Continuation of application No. 13/414,695, filed on Mar. 7, 2012, now Pat. No. 9,498,370.
(Continued)

(51) Int. Cl.
*A61B 17/66* (2006.01)
*A61B 17/17* (2006.01)
(Continued)

(52) U.S. Cl.
CPC ............ *A61F 5/3761* (2013.01); *A61B 17/17* (2013.01); *A61B 17/1717* (2013.01);
(Continued)

(58) Field of Classification Search
CPC .............. A61B 17/66; A61B 2017/565; A61B 2017/603; A61B 2017/681
See application file for complete search history.

(56) References Cited

U.S. PATENT DOCUMENTS 4,611,586 A * 9/1986 Agee .................. A61B 17/6425
606/55
4,620,533 A   11/1986 Mears
(Continued)

FOREIGN PATENT DOCUMENTS

EP    1844721 A1   10/2007
FR    2831792 A1   5/2003
(Continued)

OTHER PUBLICATIONS

Clifford R. Wheeless III, M.D., "External Fixators for Distal Radius Fractures," Wheelessonline.com, May 9, 2011.
(Continued)

*Primary Examiner* — Nicholas Woodall
(74) *Attorney, Agent, or Firm* — Weiss & Arons LLP

(57) ABSTRACT

Apparatus and methods for preparing a fractured bone for repair. Preparing the bone may include fracture reduction. Preparing the bone may include holding a fracture in reduction. Preparing the bone may include identifying locations for obtaining access to an interior region of the bone. The apparatus may include structures outside the bone that interact with fragments of the bone. The structures may participate in the reduction. The structures may participate in holding the reduction. The structures may participate in identifying the locations.

26 Claims, 53 Drawing Sheets

Related U.S. Application Data

(60) Provisional application No. 61/450,112, filed on Mar. 7, 2011.

(51) Int. Cl.
*A61F 5/37* (2006.01)
*A61B 17/68* (2006.01)
*A61B 17/56* (2006.01)
*A61B 17/60* (2006.01)
*A61B 17/72* (2006.01)
*A61B 17/64* (2006.01)

(52) U.S. Cl.
CPC .......... *A61B 17/6458* (2013.01); *A61B 17/66* (2013.01); *A61B 17/68* (2013.01); *A61B 17/1782* (2016.11); *A61B 17/6441* (2013.01); *A61B 17/72* (2013.01); *A61B 2017/565* (2013.01); *A61B 2017/603* (2013.01); *A61B 2017/681* (2013.01)

(56) References Cited

U.S. PATENT DOCUMENTS

| | | | |
|---|---|---|---|
| 4,920,959 | A | 5/1990 | Witzel et al. |
| 4,922,896 | A * | 5/1990 | Agee ................. A61B 17/6425 606/55 |
| 6,258,096 | B1 | 7/2001 | Seki |
| 6,652,524 | B1 | 11/2003 | Weiner |
| 6,709,433 | B1 | 3/2004 | Schoenefeld |
| 6,793,655 | B2 | 9/2004 | Orsak |
| 7,520,879 | B2 | 4/2009 | Justis et al. |
| 7,749,232 | B2 | 7/2010 | Salerni |
| 8,172,855 | B2 | 5/2012 | Abdou |
| 8,518,039 | B2 | 8/2013 | Mirza et al. |
| 2005/0234472 | A1 | 10/2005 | Huebner |
| 2006/0229602 | A1 | 10/2006 | Olsen |
| 2013/0116692 | A1 | 5/2013 | Daluiski et al. |
| 2013/0204250 | A1 | 8/2013 | McDevitt et al. |

FOREIGN PATENT DOCUMENTS

| | | |
|---|---|---|
| JP | 60077747 | 5/1985 |
| JP | 6266850 | 3/1987 |
| JP | 3092151 | 4/1991 |
| JP | 10509627 | 9/1998 |
| JP | 2006101896 | 4/2006 |
| JP | 2005065762 | 3/2007 |
| JP | 2011502028 | 1/2011 |
| WO | WO2013119833 | 8/2013 |

OTHER PUBLICATIONS

"Chinese Finger Trap," Wikipedia.com, Feb. 15, 2012.
"Chinese Finger Trap," Wikipedia.com, Mar. 5, 2012.
Supplementary Partial European Search Report for European Patent Application No. EP12743053, Nov. 6. 2014.
International Search Report for International Application No. PCT/US2012/028145, International Searching Authority, dated Sep. 13, 2012.
Written Opinion of the International Searching Authority for International Application No. PCT/US2012/028145, International Searching Authority, dated Sep. 13, 2012.
Extended European Search Report for European Patent Application No. EP12743053, Mar. 9, 2015.
Japanese Official Action for Japanese Patent Application No. 2013557842, dated Jan. 6, 2016.
Uncertified English language translation of Japanese Official Action for Japanese Patent Application No. 2013557842, dated Jan. 6, 2016.
English language abstract of JP2006101896, JPO and INPIT (National Center for Industrial Property Information and Training), retrieved on Jan. 12, 2016.
Australian Patent Examination Report for Australian Patent Application No. 2012225496, dated Aug. 15, 2016.

* cited by examiner

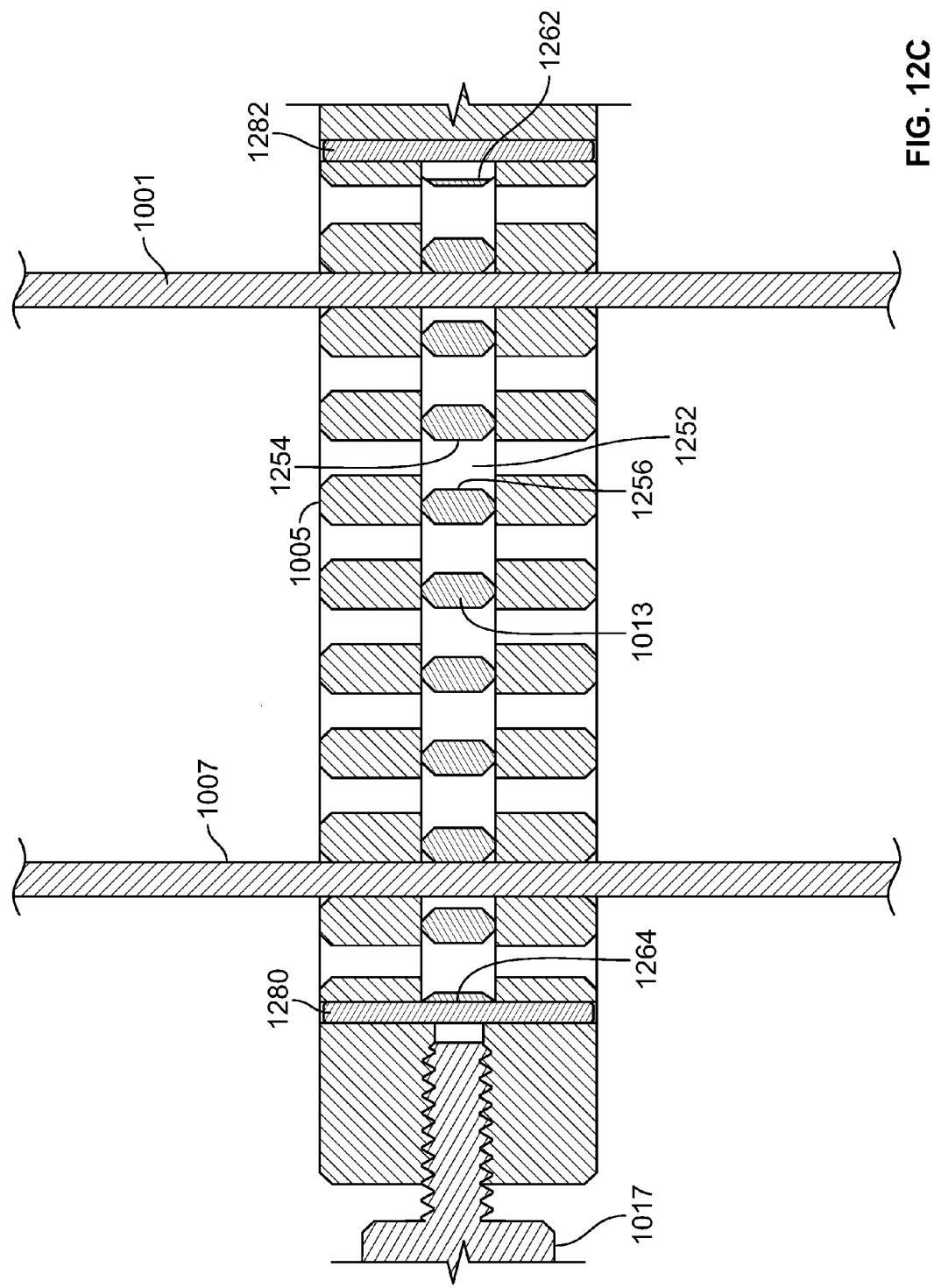

APPARATUS AND METHODS FOR BONE REPAIR PREPARATION

CROSS-REFERENCE TO OTHER APPLICATIONS

This application is a divisional of U.S. patent application Ser. No. 13/414,695, filed on Mar. 7, 2012, which is a nonprovisional of U.S. Provisional Application No. 61/450,112, which was filed on Mar. 7, 2011, both of which are hereby incorporated by reference herein in their entireties.

FIELD OF TECHNOLOGY

Aspects of the disclosure relate to providing apparatus and methods for repairing bone fractures. In particular, the disclosure relates to apparatus and methods for preparing a fractured bone for receiving a therapeutic implant.

BACKGROUND

Bone fracture fixation may involve the anchoring of bone fragments to a rigid support that is outside or inside the bone. Typical supports include (a) a plate that is screwed to the outside of the bone; and (b) an implant that is inserted inside the bone.

Therapeutic use of a support depends reducing the fracture and holding the reduction during administration of the support. Typically, a clinician inserts pins in the bone fragments and reduces the fracture by moving anatomy adjacent the bone fractures directly with hands. Another clinician then braces the pins, in a procedure known as external fixation, using wholly external pins that run between the inserted pins. The wholly external and internal pins are joined at junction members that are secured by set screws.

The use of direct manual reduction and bracing pins with junctions offers limited control over bone fragment positioning and may involve numerous manual tasks that may be difficult to coordinate in such a manner that a reduction is efficiently achieved and properly held.

It would be desirable, therefore, to provide apparatus and methods for preparing a fractured bone for repair.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which:

FIG. 12C shows a cross-sectional view, taken along lines 12C-12C (shown in FIG. 10) of the apparatus shown in FIG. 10.

DETAILED DESCRIPTION

Figures 1, 2A:
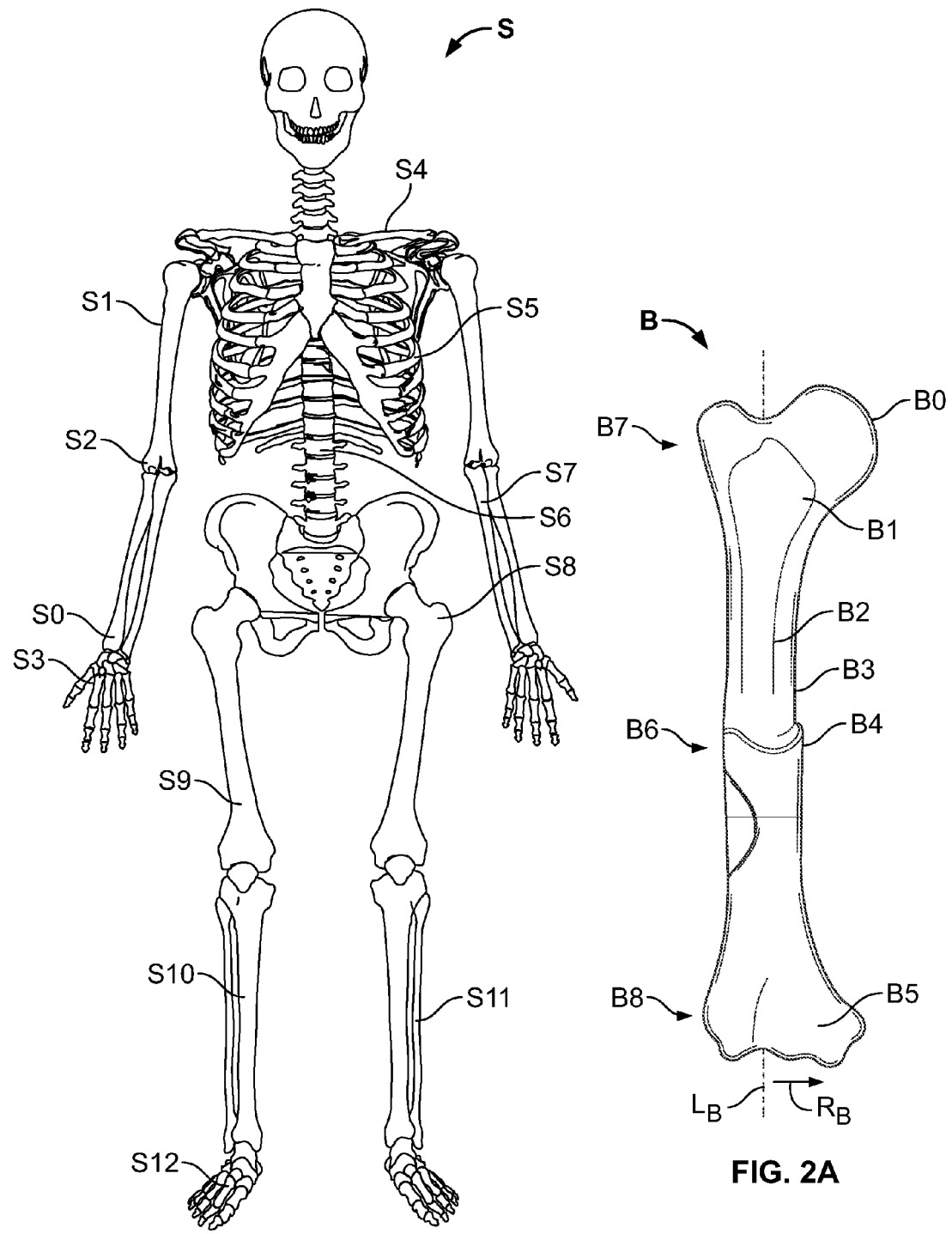
FIG. 1 shows anatomy in connection with which the invention may be practiced.
FIG. 2A shows a portion of the anatomy shown in FIG. 1.

Apparatus and methods for preparing a fractured bone for therapy are provided.

The bone may have one, two, three or more fragments. (A one-fragment fractured bone may have a fracture that did not completely separate the bone into two or more fragments.) The bone may be repaired using an implant and one or more anchors to fasten the fragments to the implant.

Preparation of the bone for repair may include reduction of the fracture, holding the fracture in a reduced configuration, selecting a site for the implant in the bone interior, selecting a site for an access hole in the bone through which to deliver the implant to the bone interior, opening the hole, clearing a cavity in the interior and any other suitable steps. Apparatus and methods shown and described in commonly owned U.S. Patent Application Publications Nos.: US20090182336, US20110178520, US20110190832, US20110218626 and US20110218585, all of which are hereby incorporated by reference herein in their entireties show apparatus and methods that may be used in connection with some of the aforementioned steps.

Fracture reduction may involve translation and rotation of a bone fragment along and about orthogonal axes having an origin in the fragment. For example, a clinician may translate or rotate (or translate and rotate) a bone fragment relative to the axes to maneuver the bone fragment into a position in which the fragment can be anchored to the implant. When the fragment is so positioned, the position may be fixed to prepare the fragment for anchoring to the implant.

The clinician may position the bone fragment without piercing the skin by manipulating anatomy.

The clinician may position the bone fragment using a bone penetrating member. Some of the apparatus and methods may be used to do so. The bone penetrating member may be elongated and have a first end that penetrates the bone fragment and forms an interference fit therewith. The bone penetrating member may have a second end that may be manipulated away from the bone. The bone penetrating member may pierce the skin. The bone penetrating member may penetrate bone from which skin has been displaced.

The clinician may fix a reduced position of a first bone fragment relative to a second bone fragment by securing the bone penetrating member to the second bone fragment. The second bone fragment may be naturally engaged with anatomy, such as skeletal anatomy, such that the second bone fragment is relatively stable. The second bone fragment may be used as a "reference" fragment for evaluating positioning, for example of the first bone fragment, in connection with fracture reduction.

The first and second bone fragments may be manipulated, perhaps with corresponding first and second bone penetrating members. The first and second bone penetrating members may be manipulated free of assistance from an exterior device. The first and second bone penetrating members may be manipulated in concert with external device. The external device may secure positions of the first and second bone penetrating members, relative to each other. The first and second bone penetrating members, when placed to transect one or more fractures, may fix the reduced positions of the first and second fragments without mutual securement of the first and second bone penetrating members.

The external device may support one or more other external devices for selecting a site for the implant in the bone interior, selecting a site for an access hole in the bone through which to deliver the implant to the bone interior, opening the hole, clearing a cavity in the interior, deploying the implant and any other suitable steps or procedures. Surgical tools that may be used in connection with these steps may include saws, drills, wires, broaches and any other suitable surgical tools.

The apparatus may include, and the methods may involve, the external device.

The apparatus may include exclusively radiolucent materials. The apparatus may include exclusively radiopaque materials. The apparatus may include both radiolucent and radiopaque materials.

In some embodiments, the apparatus may include, and the methods may involve, apparatus for reducing a fracture of a bone. The apparatus may include a first bone penetrating element. The apparatus may include a second bone penetrating element. The apparatus may include a bridging element. The bridging element may be deployed external to the bone. The bridging element may be configured to receive the first bone penetrating element and the second bone penetrating element. The apparatus may include a retention mechanism that is configured to retain a first position, relative to the bridging element, of the first bone penetrating element and a second position, relative to the bridging element, of the second bone penetrating element.

The retention mechanism may include an elongated pressure distribution member that is configured to apply pressure to the first bone penetrating element and the second bone penetrating element. The pressure distribution member may retain the first bone penetrating element in the first position and the second bone penetrating element in the second position.

The apparatus may include a fixation mechanism that is configured to deliver pressure to a portion of the pressure distribution member such that the pressure distribution member retains the first bone penetrating element in the first position and the second bone penetrating element in the second position.

The fixation mechanism may include a set screw.

The apparatus may include a third bone penetrating member and a base. The third bone penetrating member may be configured to engage the base with a reference bone fragment. The first bone penetrating member may be configured to position a first bone fragment relative to the reference bone fragment.

The base may include a collar that is configured to receive the third bone penetrating member.

The apparatus may include an elevation lock for fixing an elevation of the base relative to the bone.

The apparatus may include a length lock for fixing a length between the bridging member and the collar.

The second bone penetrating member may be configured to position a second bone fragment relative to the reference bone fragment.

The apparatus may include a support that is configured to rigidly join the base to the bridging element. The support may define a recess for electromagnetic imaging of the bone and attendant apparatus. A portion of the recess may substantially coincide with a longitudinal axis of the bone.

The apparatus may include a hinge that joins the support to the bridging element. The apparatus may include a hinge lock that is configured to fix the bridging member at an oblique angle to the support.

The apparatus may include a unitary frame. The frame may include a first receptacle for receiving a first bone penetrating element; a second receptacle for receiving a second bone penetrating element; and a third receptacle for receiving a third bone penetrating element.

The first and second bone penetrating elements may be configured to move first and second bone fragments, respectively, relative to a third bone fragment that corresponds to the third bone penetrating element. The first receptacle and the second receptacle may define a first ray that originates at the first receptacle. The first receptacle and the third receptacle may define a second ray that originates at the first receptacle; and the first and second rays define an acute angle.

The angle may range from about 40° to about 89°. The angle may range from about 45° to about 80°. The angle may range from about 55° to about 75°.

The first receptacle and the second receptacle may correspond to first and second anatomical half-spaces of the bone, the first anatomical half-space being separated by a plane that substantially bisects the bone. The first anatomical half-space may be an anterior half-space and the second anatomical half-space may be a posterior half-space. The first anatomical half-space may be a volar half-space; and the second anatomical half-space may be a dorsal half-space.

The first anatomical half-space may be a medial half-space; and the second anatomical half-space may be a lateral half-space.

Anatomical planes, or view planes, such as anterior-posterior and medial-lateral, may be instructive for illustrating the apparatus and methods. It will be understood that the anterior-posterior plane is a plane that is normal to an axis running from anterior to posterior in an anatomical feature. It will be understood that the medial-lateral plane is a plane that is normal to an axis running from medial to lateral in an anatomical feature.

The third receptacle may correspond to a plane that substantially bisects the bone and defines first and second anatomical half-spaces of the bone. The first anatomical half-space may be an anterior half-space; and the second anatomical half-space may be a posterior half-space.

The first anatomical half-space may be a volar half-space; and the second anatomical half-space may be a dorsal half-space. The first anatomical half-space may be a medial half-space; and the second anatomical half-space may be a lateral half-space.

The methods may include a method for reducing a fracture. The method may include inserting a first bone penetrating member in a first bone fragment; inserting a second bone penetrating member in a second bone fragment; and distributing a locking force from an actuator to the first bone penetrating member and the second bone penetrating member to lock the first bone penetrating member and the second bone penetrating member to a bridging member that spans from the first bone penetrating member to the second bone penetrating member.

The method may include rotating the bridging member to an oblique angle relative to a longitudinal axis of a reference bone fragment. The angle may be a radial inclination.

The method may include fixing the bridging member at the oblique angle by pinning a base to the reference fragment. The base may be rigidly joined to the bridging member.

The method may include adjusting an elevation, relative to a reference bone fragment, of a base to rotate the first and second bone fragments to an angle relative to the reference bone fragment. The angle may be a volar tilt. The method may include fixing the elevation to fix the angle.

The method may include adjusting a position, relative to a base, of a third bone penetrating member that is engaged with a reference bone fragment, to adjust a distance between (a) the first and second bone fragments; and (b) the reference bone fragment.

The distance may correspond to a radial height.

The method may include fixing a position of a collar relative to the base to fix the distance.

The method may include fixing the bridging member relative to a reference bone using a rigid radiopaque support having a recess; and imaging an interior of the bone via the recess.

The apparatus may include a base that is configured to be secured to a first bone fragment; and a bone fragment manipulator. The bone fragment manipulator may be in mechanical communication with the base. The bone fragment manipulator may be configured to: be rigidly engaged with a second bone fragment; displace the second bone fragment along three orthogonal axes; and rotate the bone second bone fragment along each of the three orthogonal axes.

The apparatus may include a pressure source that is configured to fix the manipulator to substantially prevent: displacement of the second bone fragment along the three orthogonal axes; and rotation of the second bone fragment about the three orthogonal axes.

The bone fragment manipulator may include an elongated bone penetrating member; and a collar configured to receive the elongated bone penetrating member. The bone fragment manipulator may include a pressure source that is configured to lock the bone penetrating member relative to the collar. The bone fragment manipulator may include a collar support that is configured to translate in: a first direction; and a second direction that is orthogonal to the first direction. The bone fragment manipulator may include a pressure source that is configured to lock the collar relative to the collar support.

The bone fragment manipulator may include a pressure source that is configured to lock the collar support relative to the base.

The pressure source may be configured to lock the collar relative to the collar support. The pressure source may be configured to lock the collar support relative to the base.

The pressure source may be a first pressure source. The apparatus may include a second pressure source that is configured to lock the collar support relative to the base.

The collar may include a collet. The collet may include an articulating surface that articulates relative to the collar support. The pressure source may include a thread of the collet. The articulating surface may include a substantially spherical curvature.

The collet may include a cannulated body for receiving the elongated bone penetrating member. The cannulated body may include outer threads. The cannulated body may include retention fingers. The retention fingers may be configured to retain the elongated bone penetrating member. The cannulated body may include a tapered form for receiving the cannulated body and compressing the retention fingers against the elongated bone penetrating member. The cannulated body may include a female threaded member for engaging the outer threads and directing the cannulated body into the tapered form.

The female threaded member may include a first curved articulating surface for articulating against the collar support. The tapered form may include a second curved articulating surface for articulating against the collar support. The tapered form may include expansion members that are configured to engage the collar support in response to engagement of the elongated bone penetrating member by the retention fingers.

The apparatus may include a detent that limits rotational displacement, relative to the collar support, of the tapered form. The detent may include a pin that extends from the tapered form and is configured to interfere with the collar support.

The female threaded member and the tapered form may be configured to be displaced from each other by force of the retention fingers against the form.

The collar support may include an upper plate and a lower plate. Displacement of the female threaded member from the tapered form may displace the upper plate from the lower plate.

The base may include a frame that is configured to limit displacement of the upper plate from the lower plate.

The collet may lock the elongated bone penetrating member by applying pressure: (a) through the female threaded member and the tapered form to the collar support; and (b) through the collar support to the frame.

The bone fragment manipulator may be a first bone-fragment-manipulator and the three orthogonal axes may correspond to the second bone fragment. The apparatus may include a second bone fragment manipulator that is in mechanical communication with the base. The second bone fragment manipulator may be configured to: be rigidly engaged with a third bone fragment; displace the third bone fragment along three orthogonal axes that correspond to the third bone fragment; and rotate the third bone fragment along each of the three orthogonal axes.

The apparatus may include a malleable frame; a first collar that is fixed to the frame and configured to receive a first elongated bone penetrating member; and a second collar that is fixed to the frame and configured to receive a second elongated bone penetrating member. The malleable frame may be configured to retain a position of the second elongated bone penetrating member relative to the first elongated bone penetrating member.

The apparatus may include a first control handle that is rigidly coupled to the first collar; and a second control handle that is rigidly coupled to the second collar. The second control handle may be configured to move the second collar from a first position relative to the first collar to a second position relative to the first collar.

The first control handle, in use, may be coupled to the first collar and may be, after use, removable from the first collar. The second control handle, in use, may be coupled to the second collar and may be, after use, removable from the second collar.

The first collar may include a first pressure source that is configured to lock the first elongated bone penetrating member relative to the first collar; and the second collar may include a second pressure source that is configured to lock the second elongated bone penetrating member relative to the second collar.

The apparatus may include: a first support configured to support first soft tissue that corresponds to a first bone fragment; a second support configured to support second soft tissue that corresponds to a second bone fragment, the second support articulating with respect to the first support via a joint; and a lock that is configured to fix the joint to set an angle between the first support and the second support.

The apparatus may include a first bracing element that braces the first soft tissue to the first support; and a second bracing element that braces the second soft tissue to the second support.

The second bracing element may be configured to apply tension to the second soft tissue to displace the second bone fragment away from the first bone fragment.

The second bracing element may include a soft tissue grasper. The soft tissue grasper may be configured to apply increasing traction to the soft tissue as a displacement of the second bone fragment away from the first bone fragment increases.

In some embodiments, the apparatus may include, and the methods may involve, apparatus for positioning a surgical tool relative to a site interior to a fractured bone.

The apparatus may include a pin configured to penetrate a fragment of the bone; and a support that is configured to articulate relative to the pin and indicate an access point that corresponds to the site.

The support may include a concave surface for articulating against the pin. The support may include an indicator for indicating the access point. The support may include a cannulated fixture that is configured to receive the pin, the cannulated fixture including a concave surface.

The support may include a curvature that is configured to span from a first anatomical aspect of the bone to a second anatomical aspect of the bone. The first and second anatomical aspects may be normal to each other.

The first anatomical aspect may be an anterior aspect and the second anatomical aspect may be a medial aspect. The first anatomical aspect may be an anterior aspect and the second anatomical aspect may be a lateral aspect.

The first anatomical aspect may be a posterior aspect and the second anatomical aspect may be a medial aspect. The first anatomical aspect may be a posterior aspect and the second anatomical aspect may be a lateral aspect.

The first anatomical aspect may be a dorsal aspect and the second anatomical aspect may be a medial aspect. The first anatomical aspect may be a dorsal aspect and the second anatomical aspect may be a lateral aspect.

The first anatomical aspect may be a volar aspect and the second anatomical aspect may be a medial aspect.

The first anatomical aspect may be a volar aspect and the second anatomical aspect may be a lateral aspect.

The bone fragment may be a first bone fragment. The pin may be fixed to a jig that retains the first bone fragment in a reduced orientation relative to a second bone fragment. The pin and the support, when mutually engaged, may define a spherical surface. The pin may lie along a radius of the spherical surface. The pin may include a tip that substantially coincides with the geometric center of the spherical surface. The support may be configured such that the access point is located at an intersection of the spherical surface and soft tissue adjacent the bone.

The pin may include a detent that defines a maximum penetration depth of the pin into the bone fragment. The pin may include a detent that defines a minimum elevation, relative to the bone fragment, of the support when the support and the pin are engaged. The detents, together, may function like a vertical spacer.

The support may include a fixture that is configured to engage the pin; and an extension that is configured to extend, away from the fixture, along a spherical trajectory, until it contacts soft tissue adjacent the bone.

The extension may include an indicator that indicates the access point when the indicator is proximate the bone. The indicator may extend away from the extension in a direction that is orthogonal to the spherical trajectory.

The apparatus may include an elongated guide that has an end and a guide surface. The guide may be in mechanical coordination with the support such that the guide end corresponds to the access point and the guide surface is oriented to align a surgical tool with the site.

The surgical tool may be a drill, a saw, a rotary drill, a rotary saw, a k-wire, or any other suitable surgical tool. The tool may be used to initiate a hole adjacent the guide surface at the access point. The tool may be inserted into or through a cortical layer of bone. After the hole is initiated, the tool may be rotated away from its primary axis of rotation to orient the hole along a direction that leads to a site for deployment of an implant.

The pin may include a penetrating end that is configured to be placed in the bone fragment. The support may be configured to orient the guide such that the guide surface is oriented to align the surgical tool with the penetrating end.

The apparatus may include a first radiopaque target on a first target arm. The apparatus may include a second radiopaque target on a second target arm. The site and the access point may define a guide axis. The first target arm may be in mechanical communication with the pin. The second target arm may be in mechanical communication with the pin. The first target arm may be configured to support the first target at a first distance along a first direction away from the guide axis. The second target arm may be configured to support the second target at a second distance along a second direction away from the guide axis. The second direction may be substantially perpendicular to the first direction.

The first direction and the second direction may define a plane that intersects the site.

In some embodiments, the apparatus may include, and the methods may involve, apparatus for provisionally reducing and holding reduced a bone fracture comprising. The apparatus may include a mechanism to hold bone fragments stable relative to a stable part of the bone. The stable part of the bone may be a bone fragment. The stable part of the bone may be naturally engaged with the skeleton. The stable part of the bone may be naturally engaged with the skeleton at a joint.

The apparatus may include alignment features to position an implant for the inside of the bone. The implant may be an intramedullary implant. The apparatus may include a tissue protector. The apparatus may include a guide sleeve to direct access to the bone. The apparatus may include a guide sleeve to direct positioning of the implant on the inside of the bone.

The apparatus may include a non joint spanning attachment mechanism. The apparatus may include a joint spanning attachment mechanism.

The apparatus may include a positioning system that is configured to template an implant. The template may be aligned with a site for the implant. The positioning system may be registered to the template to position surgical apparatus for accessing the site.

The positioning system may be registered to a positioned K-wire.

The positioning system may be configured to place bone fragment screws or anchors in the bone fragment and into the intramedullary implant.

The apparatus may include a mechanism that allows the fragments to be manipulated in position relative to the stable bone in a controlled manner and locked into desired position.

The apparatus may include a mechanism that allows the fragments to be manipulated in position relative to the stable bone and relative to other bone fragments in a controlled manner and locked into a desired position.

The apparatus may be configured to allow, while holding the reduction, an implant to be placed into the bone without obstructing an access path or a position of the implant.

In some embodiments, the apparatus may include, and the methods may involve, apparatus for positioning an access hole in a bone. The access hole may be used for delivery of an implant to a site in an interior cavity of the bone. The apparatus may include a first member that is configured to be registered to the site in a first anatomical viewing plane; and a second member that is attached to the first member. When the second member is brought into contact with tissue in a second anatomical viewing plane that is substantially orthogonal to the first anatomical viewing plane, the second member identifies a point on the tissue and a direction that leads from that point to the site. The tissue may include hard tissue, such as bone. The tissue may include soft tissue, such as skin and connective tissue or muscle.

The first member may include a radiopaque target for registering the first member to the site.

The first member may include a pivot end that rotatably supports a frame. The frame may include a receptacle for receiving a bone penetrating member. The bone penetrating member may be configured to affix the frame to a bone fragment of the bone. The first member may include a pressure source that is configured to fix the first member relative to the frame.

The apparatus may include a strut that spans from the first anatomical view to the second anatomical view. The first member and the second member may be elongated. The first member may, away from the pivot end, support the strut. The strut may support the second member. The strut may rotatably support the second member. The strut may lockably support the second member.

When the first member and the second member are parallel, the second member may be shorter than the first member by a length that corresponds to: (a) a length of the implant; and (b) a distance between an end of the second member and an end of the site.

The second member may include a guide tube. The guide tube may be used to guide the surgical tool to a location in the interior of the bone.

The second member may have a base adjacent a distal opening of the guide tube. The base may be configured to contact an outer surface of the bone.

The base may include a contact that is configured to grip the surface to prevent translation of the base relative to the surface.

The contact may be a first contact. The apparatus may include a second contact that is configured to grip the surface to prevent, in concert with the first contact, rotation of the base relative to the surface.

The base may include a first alignment member extending from a first side of the base and a second alignment member extending from a second side of the base opposite the first side. The alignment members may be configured to tangentially engage opposing surfaces of the bone to align the guide tube with a longitudinal axis of the bone.

The base may include a first lateral cleat extending from a first side of the base and a second lateral cleat extending from a second side of the base opposite the first side. The lateral cleats may be configured to grip opposing surfaces of the bone to prevent the base from rotating circumferentially about a longitudinal axis of the bone.

The base may include a receptacle for a bone penetrating member such that the bone penetrating member engages the base with the bone. The receptacle may be a first receptacle and the bone penetrating member may be a second bone penetrating member. The base may include a second receptacle for a second bone penetrating member such that the second bone penetrating member engages the base with the bone. The first and second receptacles may be skewed to cause the first and second bone penetrating members to fix the base to the bone by a toenail arrangement.

The apparatus may include a first radiopaque target for registering the pivot end of the first member to the site. The apparatus may include a second radiopaque target for registering the base to the site. The second radiopaque target may extend from the base. The second radiopaque target may lie substantially in the second anatomical view plane.

The apparatus may include a bone penetrating member guide. The bone penetrating member guide may be supported by the base. The bone penetrating member guide may be aligned with the guide tube. The frame may be configured to fix a first bone fragment to a second bone fragment. The base may be configured to contact the first bone fragment. The bone penetrating member guide may be configured to direct a bone penetrating member through the second bone fragment into the implant to anchor the second bone fragment to the implant.

In some embodiments, the apparatus may include, and the methods may involve, apparatus that includes a pointer that corresponds to first sites on a bone that are spaced a substantially uniform distance from an internal point in the bone. The internal point may correspond to a location for a bone implant. The apparatus may include an engagement element that extends away from the pointer. The engagement element may be configured to rotate about a pin that is fixed relative to the bone and oriented at an angle to the bone. A change in the angle may cause the pointer to correspond to second sites on the bone. The second sites may be different from the first sites and may be spaced apart from the internal point by the substantially uniform distance.

The substantially uniform distance may correspond to a length of the implant.

The apparatus may include a pointer that corresponds to sites on a bone that are spaced a substantially uniform distance from an internal point in the bone. The internal point may correspond to a location for a bone implant. The apparatus may include an engagement element that extends away from the pointer. The engagement element may be configured to rotate about a pin that is fixed relative to the bone. The substantially uniform distance may be independent of the angle at which the pin is fixed to the bone.

In some embodiments, the apparatus may include, and the methods may involve, apparatus for positioning orthopedic tools outside a bone near a site inside the bone. The apparatus may include a tool bracket defining three orthogonal axes. The tool bracket may be translatable along one or more of the axes. The tool bracket may be rotatable about one or more of the axes. The apparatus may include a support assembly. The support assembly may include a platform that is configured to be positioned away from the bone and engaged with a fragment of the bone. The apparatus may include an adjustment boom that connects the platform to the tool bracket.

The support assembly may be configured to support the tool bracket outside the bone, near the site. The support assembly may provide to the tool bracket translation along, and rotational about, one or more of the three axes.

The adjustment boom may include a housing. The adjustment boom may include a first rod that extends from the housing to a first ball joint in the tool bracket. The adjustment boom may include a second rod that extends from a second ball joint in the housing to a bore in the platform.

The housing may be translatable and rotatable, relative to the platform, via the second rod.

The apparatus may include a radiopaque target that is configured to attach to the tool bracket for registering the tool bracket to the site using medical imaging.

The apparatus may include a guide tube. The guide tube may include a fixture that is configured to be attached to the tool bracket in an orientation. The guide tube may include a cannula. The cannula may be aligned with an axis of the site, based on the orientation. The guide tube may be configured to guide a rotary surgical tool to the site.

The apparatus may include a bone penetrating member guide. The bone penetrating member guide may include a fixture that is configured to be attached to the tool bracket in an orientation. The bone penetrating member guide may include a guide passageway that is aligned with an axis of the site based on the orientation. When the bone fragment is a first bone fragment, the guide passageway may be configured to direct a bone penetrating member through a second bone fragment into the implant to anchor the second bone fragment to the implant.

In some embodiments, the apparatus and methods may be used in conjunction with a bone penetrating member that includes a vertical spacer. The vertical spacer may be used set a height from a bone to apparatus shown and described herein. For example, using two or more such spacers, a jig or frame could be supported at a desired uniform or non-uniform height above the bone.

The vertical spacer may provide structural stability to the bone penetrating member without increasing the overall diameter of the bone penetrating member.

In some embodiments, the apparatus and methods may be used in conjunction with a bone penetrating member that includes a penetration limiter. The penetration limiter may be used to prevent penetration of bone or other tissue that for which penetration is not desired.

In some embodiments, a distal end of a bone penetrating member may include a tissue engagement feature such as threads, one or more ridges, one or more ribs or one or more barbs to increase the strength of engagement between the bone penetrating member and the bone. This may increase the amount of force that can be imparted by the bone penetrating member to the bone.

Apparatus and methods in accordance with the invention will now be described in connection with the FIGS. The features are illustrated in the context of selected embodiments. It will be understood that features shown in connection with one of the embodiments may be practiced in accordance with the principles of the invention along with features shown in connection with others of the embodiments.

Apparatus and methods described herein are illustrative. Apparatus and methods of the invention may involve some or all of the features of the illustrative apparatus and/or some or all of the steps of the illustrative methods. The steps of the methods may be performed in an order other than the order shown and described herein. Some embodiments may omit steps shown and described in connection with the illustrative methods. Some embodiments may include steps that are not shown and described in connection with the illustrative methods.

The apparatus and methods of the invention will be described in connection with embodiments and features of an illustrative bone repair devices and associated hardware and instrumentation. The device and associated hardware and instruments will be described now with reference to the FIGS. It is to be understood that other embodiments may be utilized and structural, functional and procedural modifications may be made without departing from the scope and spirit of the present invention.

FIG. 1 shows illustrative skeleton S. Skeleton S includes illustrative bones Si in which apparatus and methods in accordance with the principles of the invention may be used. Table 1 includes a partial list of bones Si.

TABLE 1

Bones $S_i$.

| Bone | Reference numeral in FIG. 1 |
| --- | --- |
| Distal Radius | $S_0$ |
| Humerus | $S_1$ |
| Proximal Radius and Ulna (Elbow) | $S_2$ |
| Metacarpals | $S_3$ |
| Clavicle | $S_4$ |
| Ribs | $S_5$ |
| Vertebrae | $S_6$ |
| Ulna | $S_7$ |
| Hip | $S_8$ |
| Femur | $S_9$ |
| Tibia | $S_{10}$ |

TABLE 1-continued

Bones $S_i$.

| Bone | Reference numeral in FIG. 1 |
| --- | --- |
| Fibula | $S_{11}$ |
| Metatarsals | $S_{12}$ |

FIG. 2A schematically shows anatomy of bone B that may be a bone Si. Anatomical features of bone B are listed in Table 2. Apparatus and methods in accordance with the principles of the invention may involve one or more of the anatomical features shown in Table 3. Features of bone B may be described in reference to bone axis LB (in which B indicates bone) and radius RB (in which B indicates bone).

TABLE 2

Anatomical features of some of the bone types that may be treated by the apparatus and methods.

| Anatomical feature | Reference numeral in FIG. 2A |
| --- | --- |
| Articular surface | $B_0$ |
| Cancellous, spongy or trabecular bone | $B_1$ |
| Medullary cavity | $B_2$ |
| Cortical or dense bone | $B_3$ |
| Periosteum | $B_4$ |
| Proximal articular surface | $B_5$ |
| Diaphysis or midshaft | $B_6$ |
| Metaphysis or end region | $B_7$ |
| Epiphysis | $B_8$ |
| Articular surface | $B_9$ |

The terms "end-bone" and "end-bone fracture" may be used to refer to fractures that occur in the epiphyseal or metaphyseal region of long bones. Such fractures include peri-articular and intra-articular fractures.

Figure 2B:
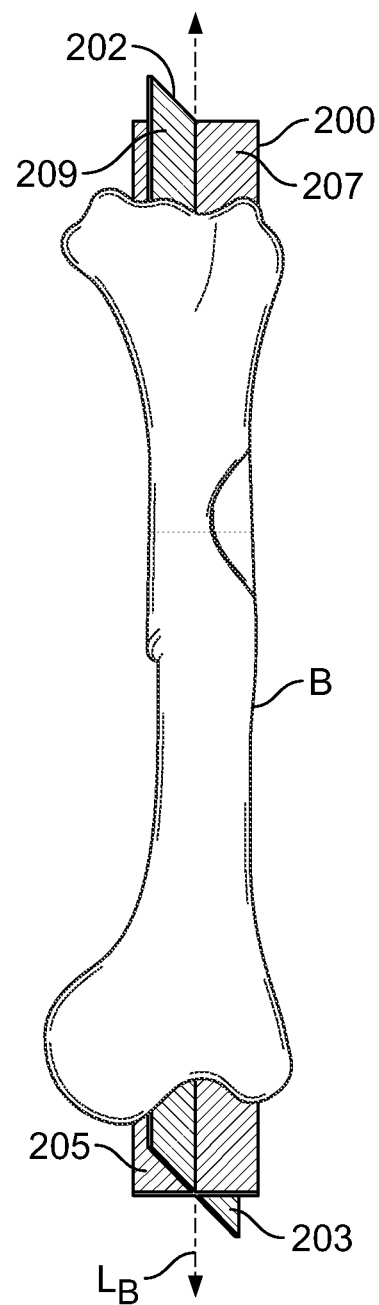
FIG. 2B shows the anatomy shown in FIG. 2A along with descriptive information.

FIG. 2B illustrates anatomical features of bone B. Bone B may be substantially bisected by plane 200. Plane 200 may include half-spaces 205 and 207. Bone B may be substantially bisected by plane 202. Plane 202 may include half-spaces 203 and 209. Half-spaces 203, 205, 207 or 209 may correspond to a dorsal, anterior, posterior, volar, medial or lateral half space. A designation of half-spaces 203, 205, 207 or 209 may be based on an orientation of bone B in skeleton S (shown in FIG. 1).

Figure 3A:
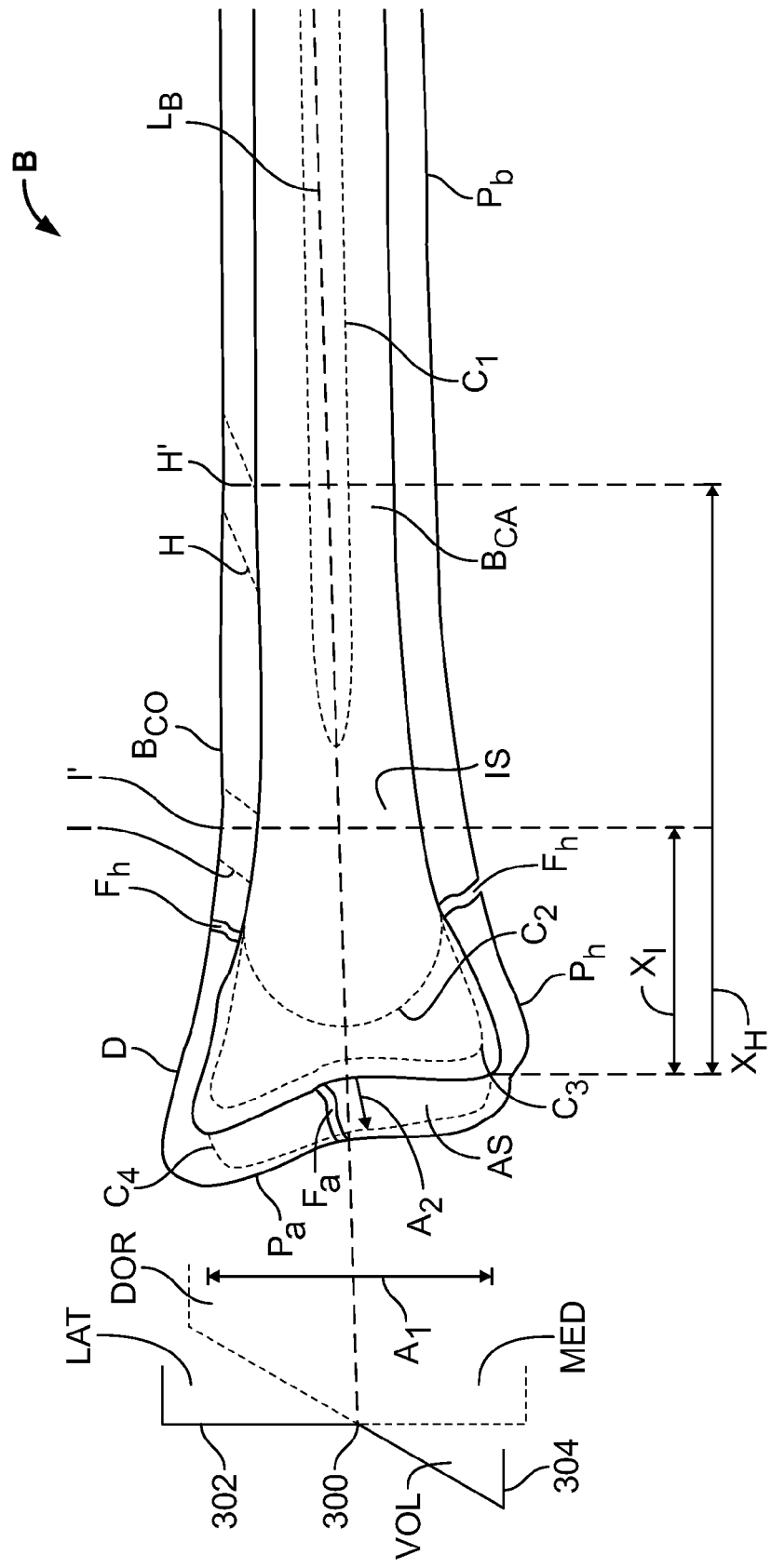
FIG. 3A shows a partial cross-sectional view of the anatomy shown in FIG. 2A.

FIG. 3A illustrates anatomical features of a fractured bone B. Reference frame 300 shows that the view of bone B is substantially in anterior/posterior plane 302. Anterior/posterior plane 302 includes a medial half-space MED and a lateral half-space LAT. Medial/lateral plane 304 includes volar half-space VOL and dorsal half-space DOR.

Bone B is illustrated as a radius that is fractured at fractures Fh and Fa. Bone B includes bone segments Pb, Ph and Pa in distal end D. Bone segment Pb is the largest portion of bone B. Bone segment Ph is a head portion of bone B. Bone segments Ph and Pa include articular surface AS. Bone segment Pa includes a portion of articular surface AS. Bone portions Pb, Ph and Pa are separated or partially separated along fractures Fa and Fh. Fracture Fa transects articular surface AS. Fracture Fh transects the head portion of bone B.

Bone B, shown in a cross section that includes approximate longitudinal axis LB, includes cortical bone BCO and cancellous bone BCA. Deployment of an implant into distal end D of bone B may require an access hole at site H'. Although H' is illustrated as being located on a radial aspect of bone B, H' may be located on other aspects of bone B, such as a volar, dorsal, lateral, medial or posterior aspect of bone B. Deployment of the implant may require displacement of cancellous bone BCA. Illustrative contours C1, C2 and C3 in cancellous bone BCA are different contours within which cancellous bone BCA may be displaced. Contour C4, which is a projection of contour C3 onto articular surface AS, shows that contour C4, for example, may be asymmetric. Contour C4 may have major axis A1 and minor axis A2 (shown in half). The other contours may also be asymmetric.

Apparatus and methods provided herein may indicate and provide an access hole H at site H'. An apparatus inserted at site H' through access hole H, may travel a distance XH through intramedullary space IS to reach the head portion of bone B. An apparatus inserted at site I' through access hole I may travel a distance XI through intramedullary space IS to reach a head portion of bone B. An apparatus inserted at H' may require a "bend" to travel through intramedullary space IS to reach a head portion of bone B. An apparatus inserted at I' may not require a "bend" to reach a head portion of bone B. Apparatus and methods provided herein may displace cancellous bone BCA within a contour such as C1, C2 or C3.

Figure 3B:
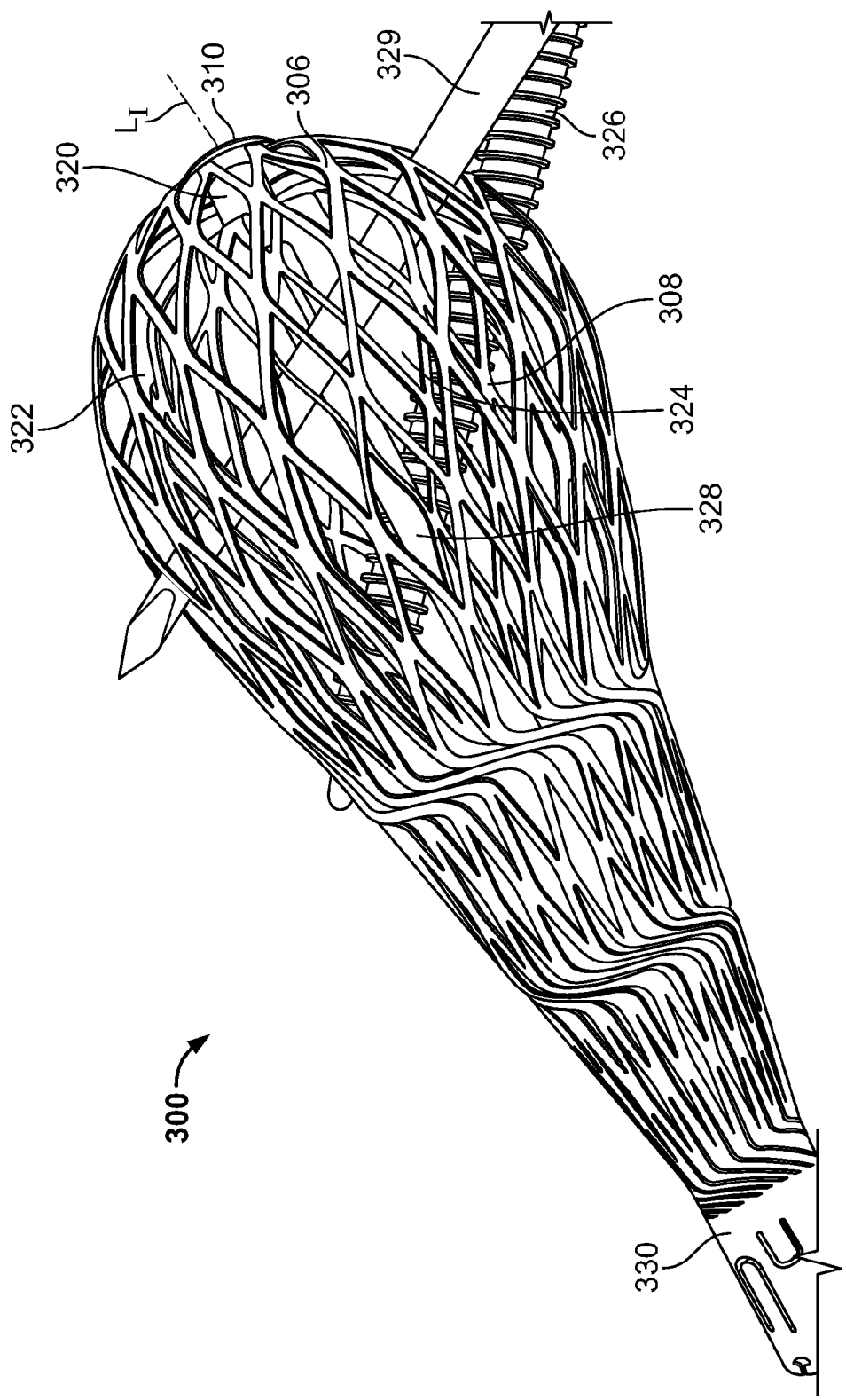
FIG. 3B shows apparatus in connection with which the invention may be practiced.

FIG. 3B shows illustrative implant 300. Implant 300 may be implanted in bone B. Implant 300 may be configured to maintain a reduction of fractures Fa and Fh.

Implant 300 may be positioned at a site interior to bone B. Implant 300 may be positioned within intramedullary space IS (shown in FIG. 3A). Implant 300 may be inserted through access hole I. Implant 300 may be inserted through access hole H.

Implant 300 may be implanted in a bone (not shown). Implant 300 is elongated along its longitudinal axis LI (in which I indicates implant). Implant 300 may include an outer expandable web 306. Implant 300 may include an inner expandable web 308. Expandable web 306 may be expanded to a radial distance from LI. Expandable web 308 may be expanded to a radial distance from LI.

Expandable web 306 may extend from proximal base 330 to distal hub 310. ("Distal," relative to "proximal," generally means the leading end of an apparatus that is inserted, or is to be inserted, in the body.) Expandable web 308 may extend from a proximal base (not shown) to distal hub 320.

Expandable web 306 may include an arrangement of cells 322. Expandable web 308 may include an arrangement of cells 324. An arrangement of cells 322 and/or cells 324 may be any suitable arrangement and may include an arrangement that provides different zones of flexibility.

Cell 322 may be configured to expand. Cell 324 may be configured to expand. Cell 322 may be expanded by expansion of expandable web 306. Cell 324 may be expanded by expansion of expandable web 308.

Cell 322 may be configured to receive any suitable anchor, such as anchor 326 or anchor 329. Cell 324 may be configured to receive any suitable anchor such as anchor 326 or anchor 329. Anchors 326 and 329 may be configured to penetrate expandable web 306 and/or expandable web 308. Anchors 326 and 329 may penetrate expandable web 306 and/or expandable web 308 at two or more locations.

Anchors 326 or 329 that may be configured to secure a bone segment to the expandable web when the expandable web is inside the bone.

Implant 300 may include component 328. Component 328 may extend longitudinally along axis LI. Component 328 may extend between distal hub 310 and proximal hub 330.

Figure 4:
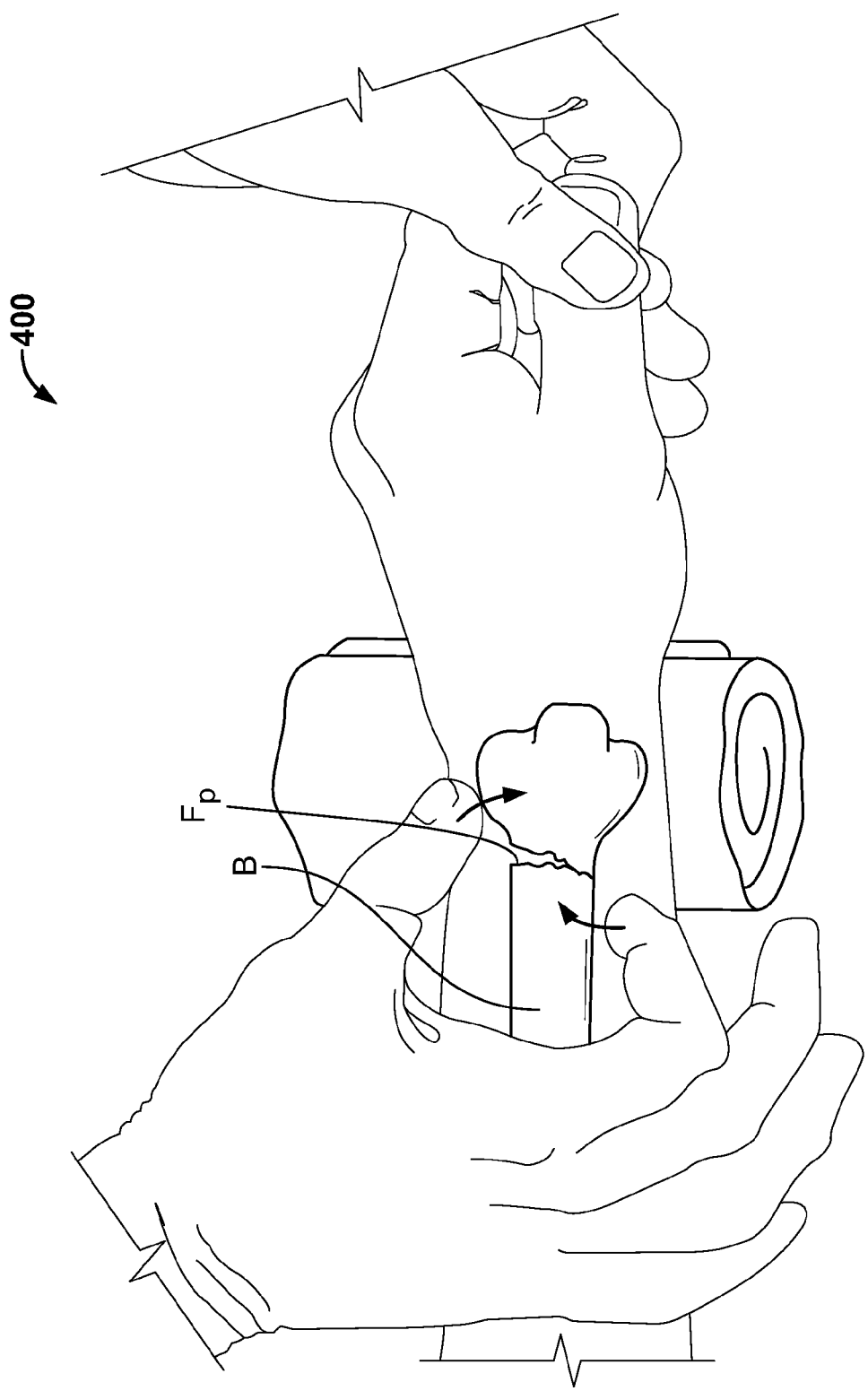
FIG. 4 shows a procedure in connection with which the invention may be practiced.

FIG. 4 shows illustrative therapeutic scenario 400. In scenario 400, manual traction techniques are applied to reestablish anatomic reduction in fracture Fp in bone B.

Provisional or temporary reduction is often undertaken in fracture repair to restore bone segments to their normal positions before they are anchored.

When the number of bone segments is small and/or the dislocation of the bone segments is modest, closed reduction techniques may be employed. Closed reduction does not include incisions and utilizes traction. The traction may utilize different tension, compression, and bending motions for reestablishing normal bone segment positioning.

For more displaced fracture patterns, a limited open reduction can be utilized. External probes, special clamps or bone penetrating members, such as wires, can be employed for the provisional reduction. Small incisions can be made allowing the probes and clamps to aid in repositioning the fracture segments. An open reduction may be performed in a surgical environment.

The wires may include metal, polymer, fiber or any other suitable material. The wires may be k-wires. The k-wires may range in diameter from about 1 mm to about 2 mm in diameter. The k-wires may have pointed faceted tips to facilitate insertion in a bone using a surgical drill. The k-wires may be driven across a fracture from bone fragment to bone fragment to retain the fragments in position relative to each other. The k-wires may be positioned and then removed strategically to facilitate the reduction procedure in a manner that reduces interference with bone cavity preparation or implant deployment.

A k-wire may be inserted into a bone segment without surgically opening the skin. A k-wire may be drilled directly through the skin and into the bone segment. A clinician may manipulate the bone segment via the k-wire. Once the bone segments are in position, k-wires may further be utilized to maintain the reduction.

Figure 5:
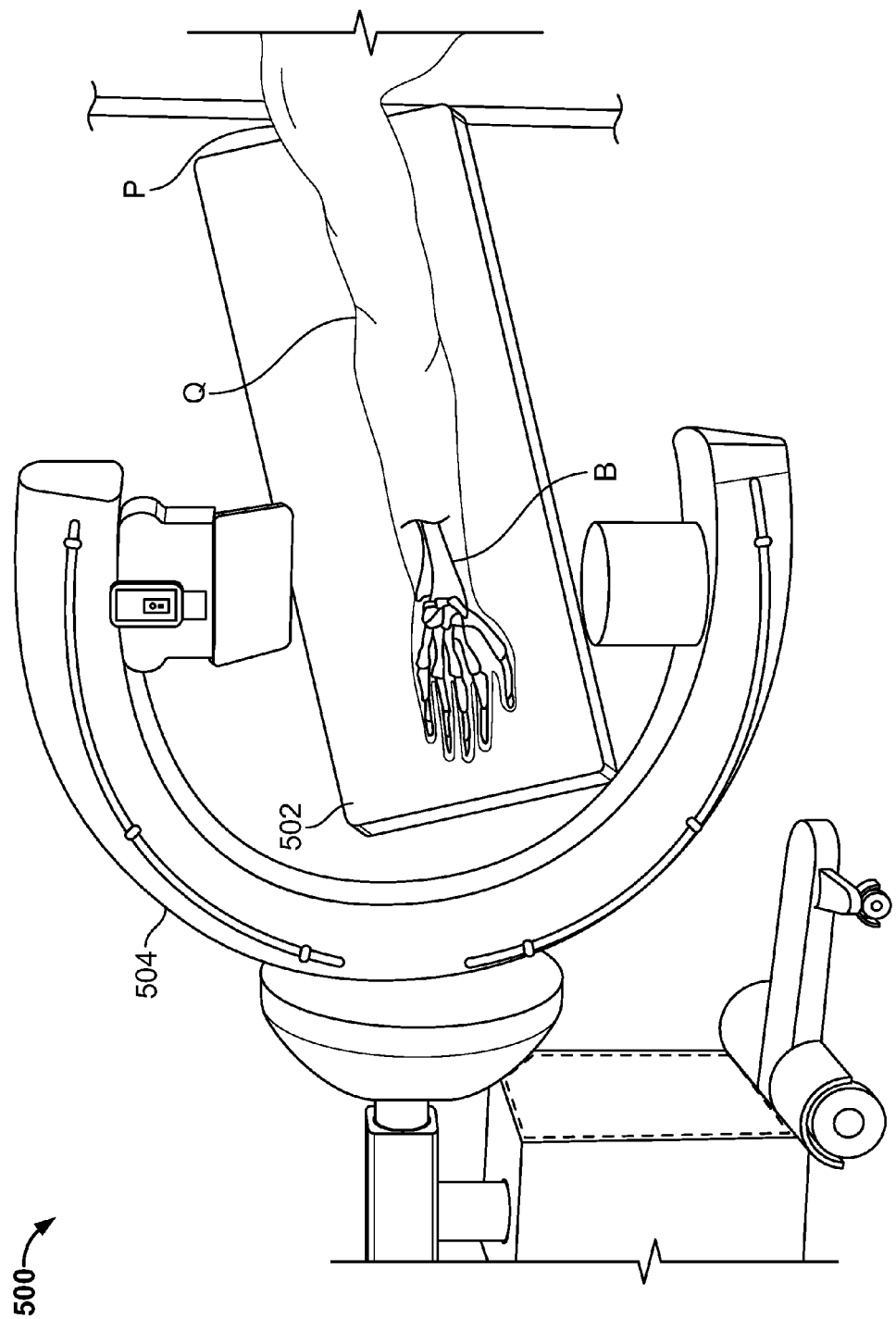
FIG. 5 shows another procedure, in connection with which the invention may be practiced, involving the anatomy shown in FIG. 2A and other anatomy.

FIG. 5 shows portion 500 of an illustrative surgical environment in which a fracture in bone B may be diagnosed and treated utilizing a therapeutic technique. Patient P may be sedated appropriately. A limb nerve block may be administered. A pressure cuff (not shown) may be used to maintain limb Q in a relatively blood-free state. Limb Q may be supported by procedure table 502 and any other appropriate supports to manage the position of bone B during surgery. Environment 500 may include imaging system 504. Imaging system 504 may be an electromagnetic imaging system. Apparatus and methods provided herein may allow obstruction-free imaging of the fracture in bone B. Imaging system 504 may show a position of one or more of a bone fragment, a jig, a target, a marker or any suitable radiopaque device.

Figure 6:
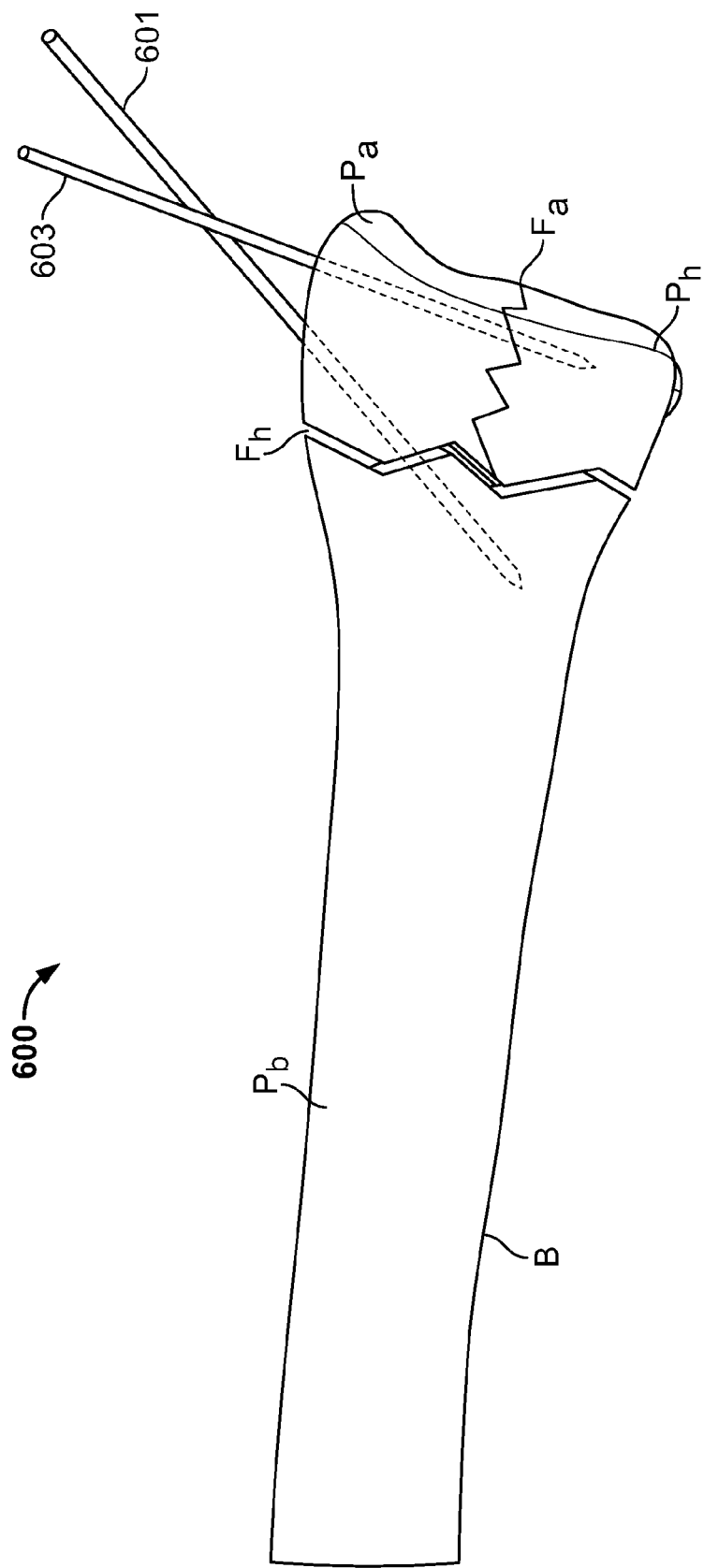
FIG. 6 shows anatomy similar to the anatomy shown in FIG. 2A, in a different condition from that shown in FIG. 2A, along with apparatus.

FIG. 6 shows illustrative therapeutic scenario 600. In scenario 600, a limited open reduction technique is utilized to reestablish anatomic reduction in fractures Fh and Fa in bone B. K-wire 601 may be drilled across fracture Fh. K-Wire 601 may maintain bone fragment Pa is a position relative to bone segment Pb. K-wire 603 may be drilled across fracture Fa. K-wire 603 may maintain bone segment Ph in a position relative to bone segment Pb. K-wire 603 may be drilled at an angle that substantially follows a subchrondral surface of bone B or any other suitable anatomical characteristic of bone B.

K-wires 601 and 603 may be drilled across fracture Fh and fracture Fa. K-wires 603 and 601 may maintain bone segments Pa and Ph in positions relative to bone segment Pb. Bone segment Pb may be a reference bone segment. Bone segment Pb may be a diaphysis or midshaft region of bone B. K-wires 601 and 603 may provisionally position bone segments Pa and Ph relative to bone segment Pb. K-wires may be manipulated to position bone segments Pb and Pa in a variety of therapeutic positions relative to bone segment Pb.

Figure 7:
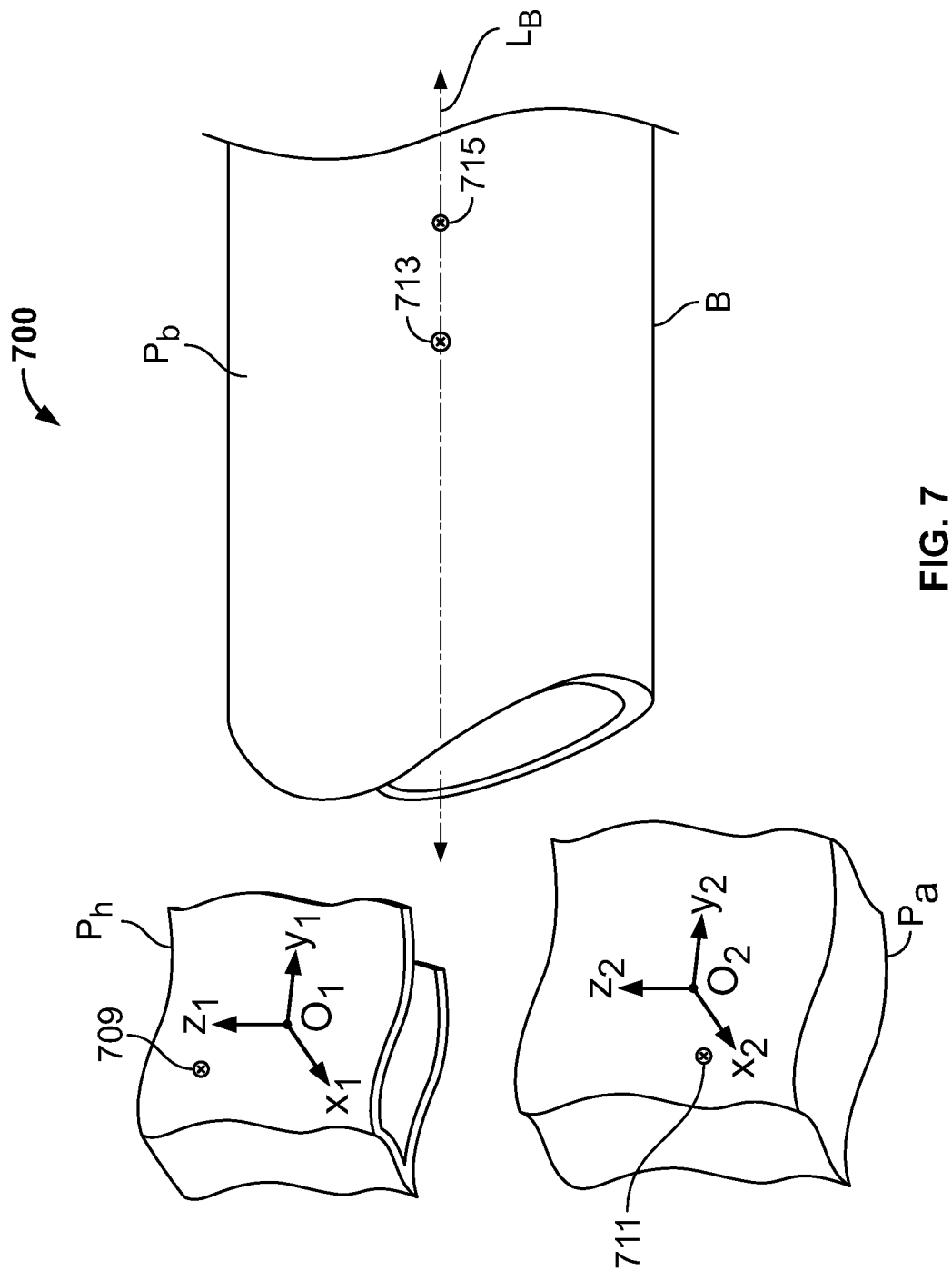
FIG. 7 shows schematic anatomy in connection with which the invention may be practiced.

FIG. 7 shows illustrative bone segments 700 of bone B. Bone segment Pb may be the largest bone segment. A fracture, such as fracture Fh or fracture Fa (shown in FIG. 3A), may allow bone segments Pa or Ph to shift out of anatomic alignment with respect to bone segment Pb. Bone segment Pb may serve as a reference bone segment, such that, for therapeutic treatment, one or more bone segments such as Pa and Ph may be positioned relative to the reference bone segment.

The fracture may allow bone segment Ph to be displaced along one or more of orthogonal axes x1, y1 and z1, centered at O1. The fracture may allow bone segment Ph to rotate about one or more of the axes centered at O1. The fracture may allow bone segment Pa to be displaced along one or more of orthogonal axes x2, y2, and z2, centered at O2. The fracture may allow bone segment Pa to rotate about one or more of the axes centered at O2.

A bone-penetrating member may be inserted into bone segment Ph at a site such as 709. The bone penetrating member may allow a clinician to move Ph along or about one or more of axes x1, y1, and z1. A bone penetrating member may be drilled into bone segment Pa at a site such as 711. The bone penetrating member may allow a clinician to move Pa along or about one or more of axes x2, y2, and z2.

Bone penetrating members may be inserted in Pb at one or more sites such as 713 and 715. The bone penetrating members may anchor a device to bone segment Pb. The device may hold a position of one or both of Pa and Ph relative to segment Pb. The device may move one or both of Pa and Ph relative to segment Pb.

Figure 8:
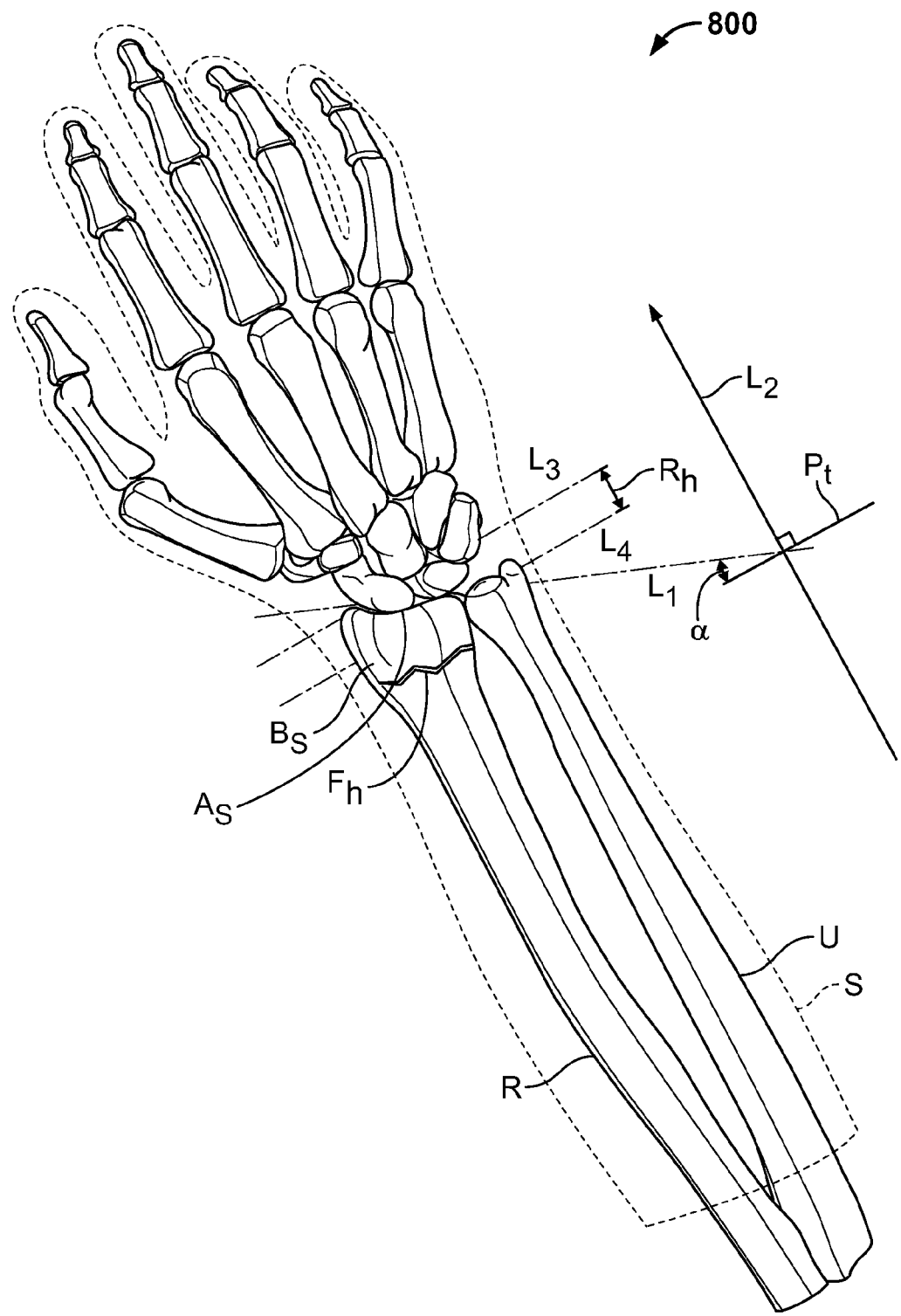
FIG. 8 shows a portion of the anatomy shown in FIG. 1 in a different state from that shown in FIG. 1.

FIG. 8 shows illustrative anatomy 800. Anatomy 800 includes a dorsal view of radius R and ulna U. Soft tissue S may be present around radius R and ulna U. Radius R and ulna U are shown in substantially volar/dorsal plane 304 (shown in FIG. 3A). Radius R includes fracture Fh. Fracture Fh may separate segment Bs from radius R. Radius R may include facture Fa (shown in FIG. 3A). Fracture Fa may separate segment Bs into segments Pa and Ph (shown in FIG. 3A). Displacement of Bs may include movement of Bs to an abnormal position relative to radius R or ulna U.

Segment Bs may normally be positioned at radial height Rh. Radial height Rh may be measured based on a distance between illustrative lines L3 and L4. Line L3 is drawn from a radial styloid and perpendicular to a longitudinal axis of radius R. Line L4 is drawn from an articular surface of radius R and perpendicular to a longitudinal axis of radius R. A normal radial height may range between 10-13 mm. Radial height Rh may be measured relative to an anatomical characteristic of ulna U. Bone segment Bs may be positioned at an abnormal radial height.

Radial inclination $\alpha$ may be an inclination, substantially in plane 302 (shown in FIG. 3A), between articular surface As and transverse plane Pt. Transverse plane Pt is normal to projection L2 of the longitudinal axis of radius R. $\alpha$ in a typical, unbroken bone may range from about 7° to about 37°. The apparatus and methods may be used to change $\alpha$ for one or more bone segments such as bone segments Pa and Ph (shown in FIG. 3A).

Figure 9:
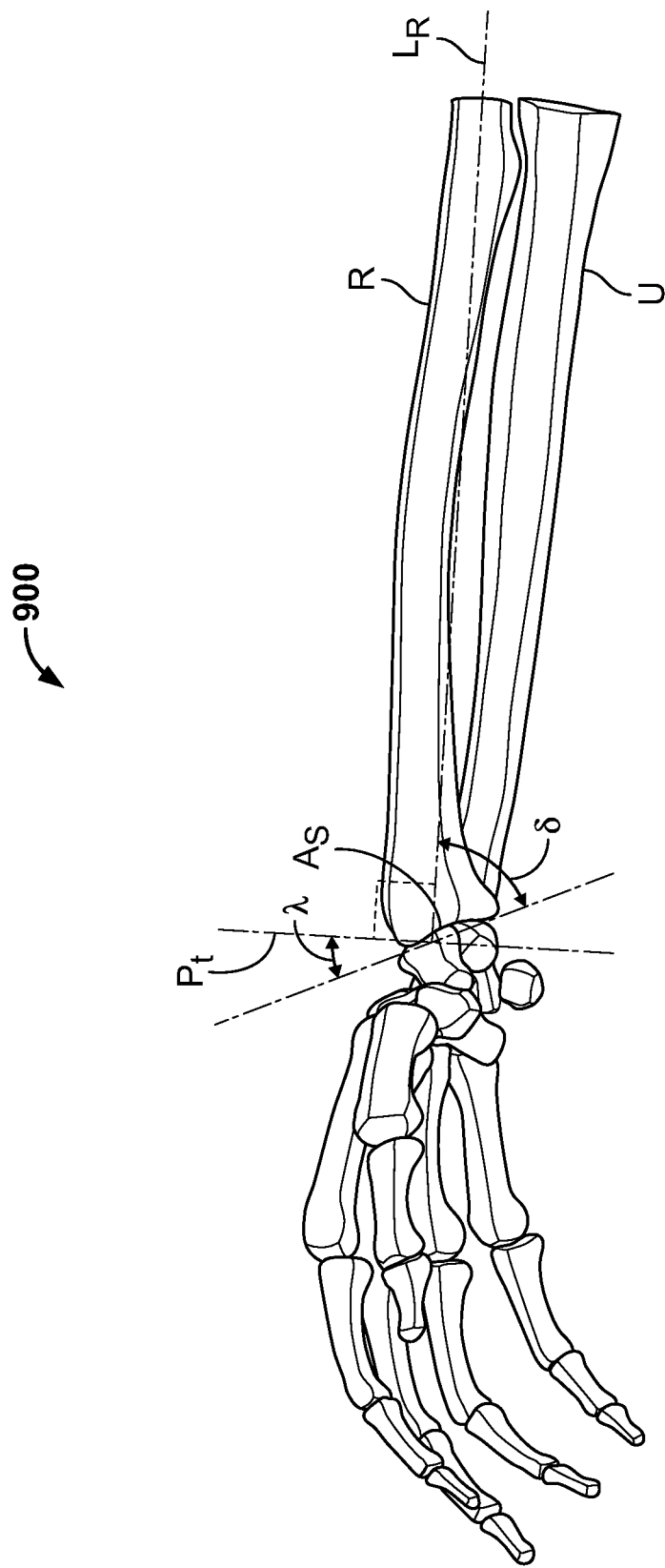
FIG. 9 shows the anatomy shown in FIG. 8 in a state that is different from that shown in FIG. 8.

FIG. 9 shows anatomy 900. Anatomy 900 shows a lateral view of radius R and ulna U. Radius R and ulna U are shown in substantially medial/lateral plane 302 (shown in FIG. 3A). Volar tilt $\lambda$ may be an inclination, substantially in plane 304 (shown in FIG. 3A), between articular surface As and transverse plane Pt (shown in a position that is different from the position shown in FIG. 8). (Volar tilt may be given by the complement of $\lambda$, represented in the FIG. by $\delta$, the angle between articular surface As and the longitudinal axis of the radius, LR.) The apparatus and methods may be used to change $\lambda$ for one or more bone segments such as bone segments Pa and Ph (shown in FIG. 3A).

Figure 10:
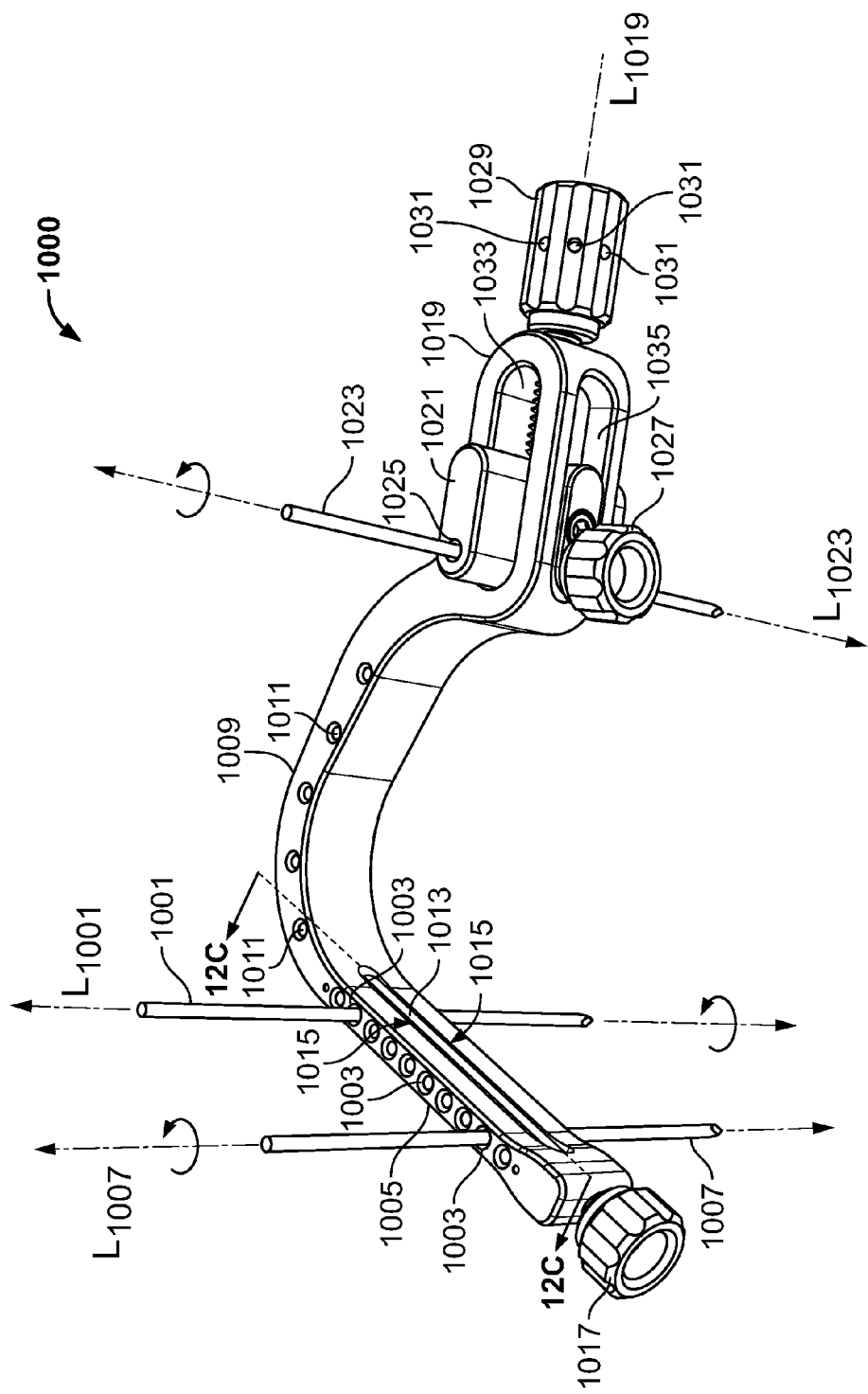
FIG. 10 shows illustrative apparatus in accordance with principles of the invention.

FIG. 10 shows illustrative jig 1000. Bone penetrating element 1001 may be drilled into bone B (shown in FIG. 2A). Bone penetrating element 1001 may be a k-wire. Bone penetrating element 1001 may be positioned in bone B relative to an anatomical landmark. Bone penetrating element 1001 may be inserted in a dorsal surface of bone B.

Jig 1000 may include bridging element 1005. Bridging element 1005 may include receptacles 1003. Receptacles 1003 may be configured to receive bone penetrating element 1001. Receptacles 1003 may be configured to receive bone penetrating element 1007. Bridging member 1005 may position bone penetrating element 1001 relative to bone penetrating element 1007.

Bone penetrating element 1001 may be inserted into a bone segment such as bone segment Ph (shown in FIG. 3A). Bone penetrating element 1003 may be inserted into a bone segment such as bone segment Pa (shown in FIG. 7). Bridging element 1005 may be moved to position bone segments Ph and Pa. For example, bridging element 1005 may be moved to change radial inclination $\alpha$ (shown in FIG. 8). A clinician may manipulate bone penetrating element 1001 to move bone segment Ph about origin O1 (shown in FIG. 7) whether or not site 709 (shown in FIG. 7) is coincident with origin O1. A clinician may manipulate bone penetrating element 1007 to move bone segment Pa about origin O2 (shown in FIG. 7) whether or not site 711 (shown in FIG. 7) is coincident with origin O2.

Bridging member 1005 may include pressure distribution member 1013. Pressure distribution member 1013 may slide in channel 1015. In a first position, pressure distribution member 1013 may allow a bone penetrating element positioned by bridging member 1005 to move within receptacle 1003. In the first position, bone penetrating element 1001 may move along axis L1001 and rotate about axis L1001. In the first position, bone penetrating element 1007 may move along axis L1007 and rotate about axis L1007. Movement of bone penetrating elements 1001 and 1007 may cause movement of bone segments Ph and Pa about axes O1 and O2, respectively.

In a second position, pressure distribution member 1013 may exert pressure on a bone penetrating element and substantially prevent movement of the bone penetrating element.

The pressure may be exerted on a bone penetrating element by narrowing, at least a portion, of receptacles 1003. In the second position, pressure distribution member 1013 may be configured to narrow a portion of receptacles 1003 that traverse pressure distribution member 1013.

In the second position, pressure distribution member 1013 may prevent movement, relative to bridging member 1005, of any bone penetrating element received by receptacles 1003 and of corresponding movements of bone segments Ph and Pa relative to origins O1 and O2, respectively.

Pressure distribution member 1013 may be set in the first position or the second position using set screw 1017. Rotation of set screw 1017 may slide pressure distribution member 1013 in channel 1015.

Jig 1000 may include base 1019. Movement of base 1019 may position bone penetrating element 1001 relative to bone penetrating element 1007. Movement of base 1019 may pivot bridging element 1005 about axis L1001. Movement of base 1019 may pivot bridging element 1005 about axis L1007. Movement of base 1019 may rotate bridging element 1005 a substantially posterior/anterior plane. Movement of base 1019 may change radial inclination α (shown in FIG. 8).

Base 1019 may include collar 1021. Collar 1021 may include receptacle 1025. Receptacle 1025 may be configured to receive bone penetrating element 1023. Bone penetrating element 1023 may be inserted in bone segment Pb (shown in FIG. 7).

Bone penetrating element 1023 may move within collar 1021. Bone penetrating element 1023 may translate along axis L1023. Bone penetrating element 1023 may rotate about axis L1023. Bone penetration element 1023 may be secured to collar 1021 using set screw 1027. In a first position set screw 1027 may allow bone penetrating element 1023 to move freely within collar 1021. In a second position, set screw 1027 may restrict movement of bone penetrating element 1023 within collar 1021. In the second position, set screw 1027 may distribute pressure to bone penetrating element 1023. The pressure may be distributed relative to collar 1021. Rotation of set screw 1027 may relieve or apply pressure to bone penetrating element 1023.

With appropriate use of set screw 1027, base 1019 may be moved up or down along bone penetrating member 1023, and locked in place, to rotate bridging member 1005 and thus adjust, and lock, volar tilt λ (shown in FIG. 9).

Collar 1021 may translate along axis L1019. Base 1019 may include channels 1033 and 1035 to allow movement of collar 1021. Rotation of set screw 1029 may translate collar 1021 along axis L1019. Set screw 1029 may restrict translation of collar 1021 along axis L1019. Set screw 1029 may include receptacles 1031. Receptacles 1031 may be configured to receive a bone penetrating element. The bone penetrating element received by receptacle 1031 may set a position of collar 1021 along axis L1019. A position of collar 1021 relative to bridging member 1005 may correspond to a radial height Rh (shown in FIG. 8).

Support 1009 may join base 1019 to bridging member 1005. Movement of base 1019 may position bone penetrating element 1023 relative to bone penetrating elements 1001 and 1007. Movement of base 1019 may move bone segments Ph or Pa (shown in FIG. 7) about origins O1 and O2 (shown in FIG. 7), respectively. Movement of base 1019 may position bone segments Ph and Pa relative to bone segment Pb (shown in FIG. 7).

Support 1009 may include receptacles 1011. Receptacles 1011 may receive a bone penetrating element. Receptacles 1011 may be configured to receive a bone penetrating element drilled into anatomy proximate to bone B (shown in FIG. 2A). For example, if bone B is a radius R (shown in FIG. 8), receptacles 1011 may receive a bone penetrating element drilled into ulna U (shown in FIG. 8).

Figure 11:
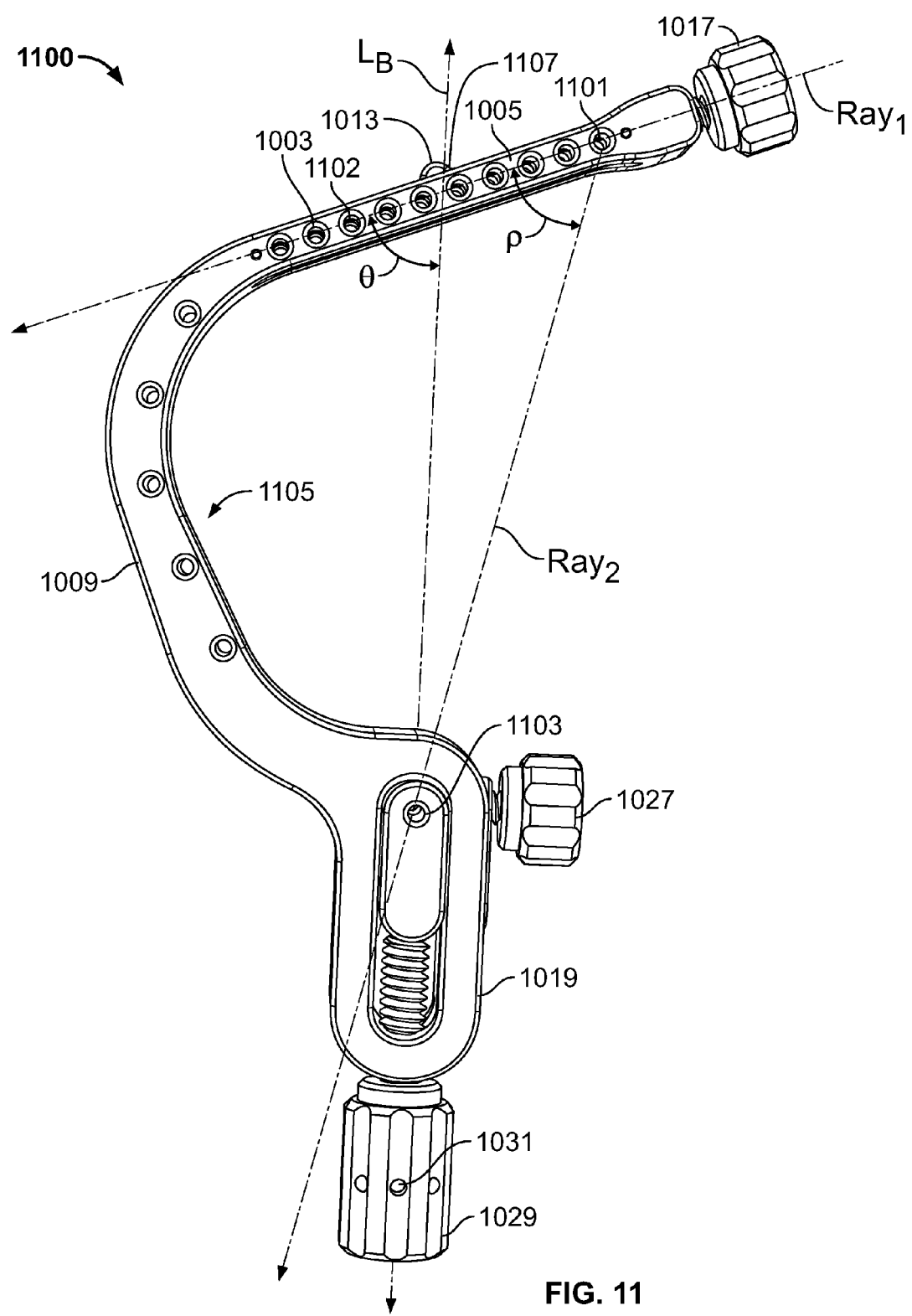
FIG. 11 shows other illustrative apparatus in accordance with principles of the invention.

FIG. 11 shows unitary frame 1100. Frame 1100 may have may have one or more features in common with jig 1000 (shown in FIG. 10). Frame 1100 may include bridging member 1005. Illustrative projection 1107 may be used to align bridging member 1005 with an anatomical landmark. Frame 1100 may include base 1019. Frame 1100 may include receptacles 1101 and 1102. Receptacles 1101 and 1102 may be configured to a receive bone penetrating elements 1001 and 1007 (shown in FIG. 10). Bone penetrating elements 1001 and 1007 may be inserted into bone segments Ph and Pa (shown in FIG. 3A).

Receptacles 1101 and 1102 may define Ray1. Receptacles 1101 and 1102 may be separated by a plane that includes axis LB (shown in FIG. 2B.) The plane may be plane 200 (shown in FIG. 2B). The plane may be plane 202 (shown in FIG. 2B). Receptacles 1101 and 1102 may receive a bone penetrating element that penetrates a half-space of bone B (shown in FIG. 2A). The half-space may be half-space 203, 205, 207 or 209 (shown in FIG. 2B).

A bone penetrating element received by receptacle 1101 may be inserted into a segment of bone B (shown in FIG. 2A). The bone segment may reside in the half-space including receptacle 1101. A bone penetrating element received by receptacle 1102 may be inserted into a segment of bone B. The bone segment may reside in the half-space including receptacle 1102.

Receptacle 1103 may be configured to receive bone penetrating element 1023 (shown in FIG. 10). Receptacle 1103 may be configured to direct bone penetrating element 1023 into bone B (shown in FIG. 2A). Bone penetrating element 1023 may be drilled into bone segment Pb (shown in FIG. 3A). Receptacle 1103 may direct bone penetrating element 1023 substantially into plane 200 (shown in FIG. 2B). Plane 200 may bisect bone B. Plane 200 may define half-spaces 207 and 205 (shown in FIG. 2B). Receptacle 1103 may direct bone penetrating element substantially along plane 202 (shown in FIG. 2B). Plane 202 may bisect bone B. Plane 202 may define half-spaces 203 and 209 (shown in FIG. 2B).

Receptacle 1103 and receptacle 1101 may define Ray2. Ray1 and Ray2 may form angle ρ. Angle ρ may be adjusted by rotating set screw 1029. Rotation of set screw 1029 may correspond to movement of receptacle 1103 along a projection of LB. Rotation of set screw 1029 may apply pressure to bone penetrating elements 1001, 1007 and 1023 (shown in FIG. 10). The pressure may move bone segments Ph and Pa relative to bone segment Pb (shown in FIG. 3A).

Angle ρ may be set by drilling a bone penetrating element though receptacle 1031. Angle ρ may correspond to a radial height Rh (shown in FIG. 8). Ray1 and Ray2 may be selected based on an anatomical characteristic of a bone.

Angle θ may be formed between Ray1 and a projection of axis LB. Angle θ may be selected to correspond to radial inclination α (shown in FIG. 8). Angle θ may be selected to correspond to volar tilt λ (shown in FIG. 9). Angle θ may be adjusted by rotating bridging member 1005. Angle θ may be set by drilling bone penetrating element 1023 through receptacle 1103 and a bone segment such as bone segment Pb (shown in FIG. 7).

Bridging member 1005, support 1009 and base 1019 may define recess 1105. Recess 1105 may provide unobstructed access to bone B (shown in FIG. 2A). Recess 1105 may facilitate imaging of bone segments Pb, Ph and Pa (shown in FIG. 3A) using imaging system 504 (shown in FIG. 5).

Figure 12A:
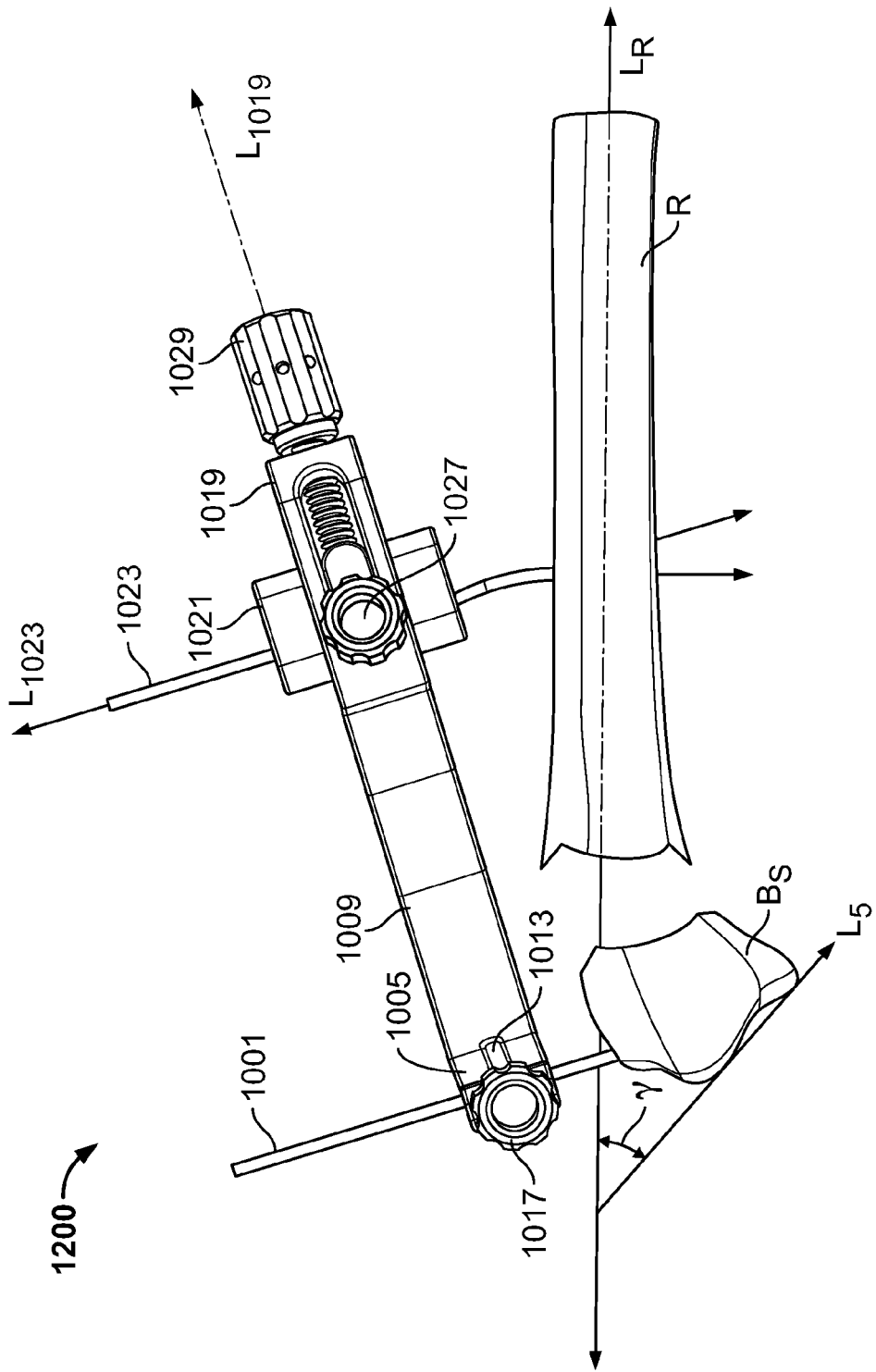
FIG. 12A shows the apparatus shown in FIG. 10 along with the anatomy shown in FIG. 8.

FIG. 12A shows illustrative therapeutic scenario 1200. Bone segment Bs is separated from radius R. The separation may be due to a fracture such as fracture Fh or fracture Fa (shown in FIG. 3A). A device such as jig 1000 (shown in FIG. 10) or unitary frame 1100 (shown in FIG. 11) may be used to position bone segment Bs relative to radius R. Radius R may have a longitudinal axis LR. A clinician may therapeutically position bone segment Bs relative to radius R. For example, the clinician may adjust volar tilt λ (shown in FIG. 9).

Bone penetrating element 1001 may be secured to bridging member 1005 by set screw 1017 and pressure distribution member 1013. Bone penetrating member 1001 may be drilled into bone segment Bs. Bone penetrating member

1001 may be used to manipulate a position of bone segment Bs about a center of bone segment Bs.

Bridging member 1005 may be secured to base 1019 via support 1009. Bone penetrating member 1023 may pass through base 1019 and collar 1021 via receptacle 1025 (shown in FIG. 10). Bone penetrating member 1023 may pass into radius R. Bridging member 1005 may be rotated by translating base 1019 along axis L1023. Base 1019 may be prevented from substantially translating along axis L1019 by collar 1021 and set screw 1029.

Translating base 1019 along axis L1023 and rotating bridging member 1005 may rotate bone segment Bs. Rotation of bone segment Bs may adjust angle γ. Angle γ may be adjusted to correspond to volar tilt lambda. Angle γ may be set using set screw 1027. Set screw 1027 may substantial prevent movement of base 1019 along axis L1023.

Figure 12B:
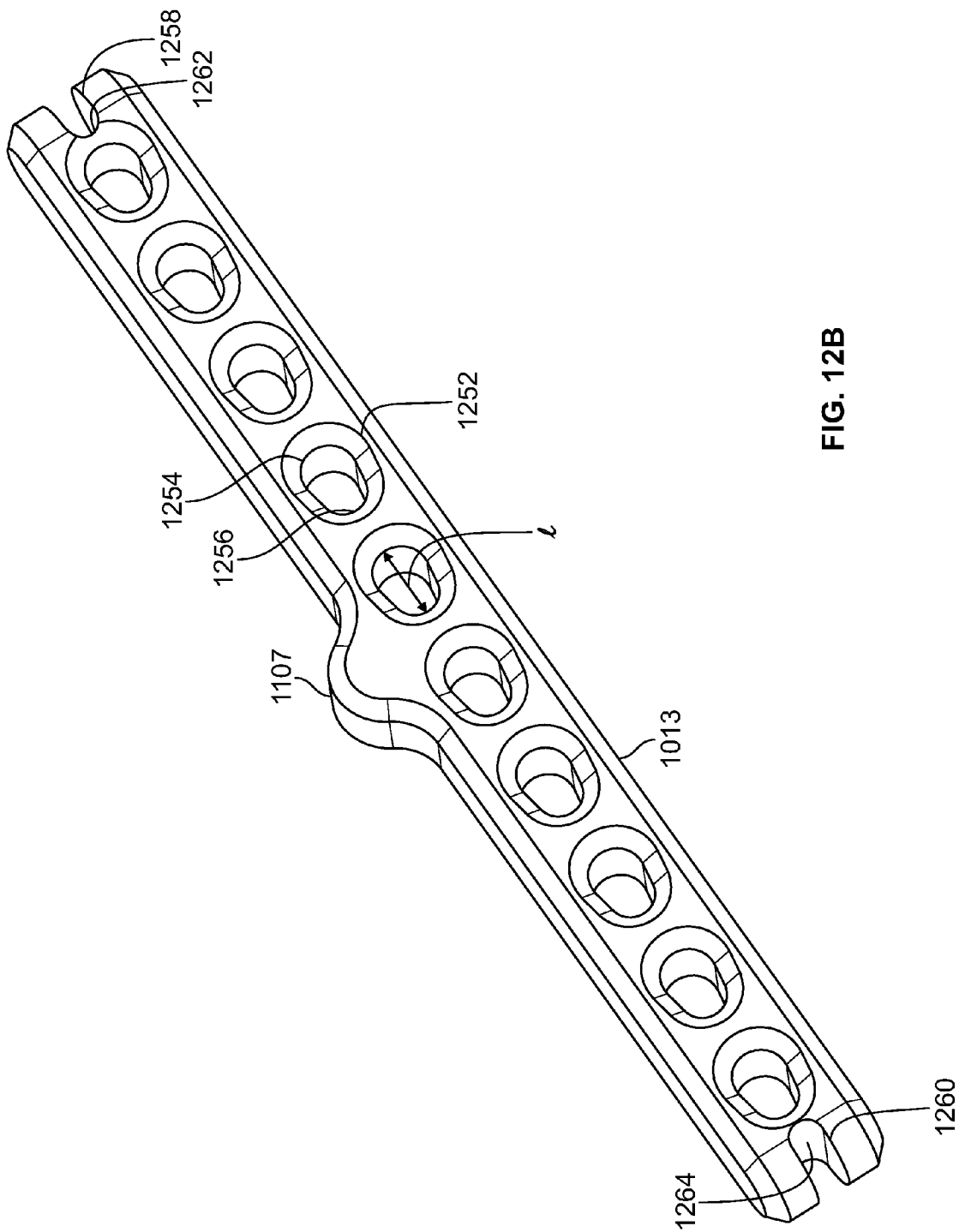
FIG. 12B shows a portion of the apparatus shown in FIG. 10.

FIG. 12B shows pressure distribution member 1013. Pressure distribution member 1013 may include one or more vias such as 1252. Each of the vias may correspond to one of receptacles 1003 (shown in FIGS. 10 and 11). Via 1252 is a pass-through for bone penetrating members such as 1001 and 1007 (shown in FIG. 10). Via 1252 may include wide end 1254 and narrow end 1256. Via 1252 may have length 1, which may be greater than the diameter of the corresponding receptacle. Pressure distribution member 1013 may, guided by channels 1258 and 1260, slide longitudinally. Detent surfaces 1262 and 1264 may limit the longitudinal motion by interference with detents (not shown) from bridging member 1005 that are positioned in the guide channels.

When a bone penetrating member is inserted or adjusted within a receptacle 1003, wide end 1254 is aligned with the receptacle. When the bone penetrating member is locked, pressure distribution member 1013 is shifted so that narrow end 1256 is aligned with the receptacle. Narrow end 1256 may be sufficiently narrow to apply pressure to the bone penetrating member to hold the bone penetrating member relative to bridging member 1005.

FIG. 12C shows pressure distribution member 1013 within bridging member 1005. Bone penetrating members 1001 and 1007 pass through vias in pressure distribution member 1013. Via 1252 is not occupied by a pressure distribution member. Detent surface 1264 abuts detent 2180. Detent surface 1262 is displaced from detent 2182. Pressure distribution member 1013 is therefore in an unlocked configuration. Set screw 1017 is affixed to pressure distribution member 1013 (out of the plane of the FIG.) such that set screw 1017 can displace pressure distribution member 1013 and generate pressure that is transmitted by pressure distribution member 1013 substantially simultaneously to any bone engaging members that may be present in bridging member 1005.

Illustrative projection 1107 may be used to align bridging member 1005 with an anatomical landmark.

FIG. 12B shows pressure distribution member 1013 within bridging member 1005. Bone penetrating members 1001 and 1007 pass through vias in pressure distribution member 1013. Via 1252 is not occupied by a pressure distribution member. Detent surface 1264 abuts detent 2180. Detent surface 1262 is displaced from detent 2182. Pressure distribution member 1013 is therefore in an unlocked configuration. Set screw 1017 is affixed to pressure distribution member 1013 (out of the plane of the FIG.) such that set screw 1017 can displace pressure distribution member 1013 and generate pressure that is transmitted by pressure distribution member 1013 substantially simultaneously to any bone engaging members that may be present in bridging member 1005.

Figure 13:
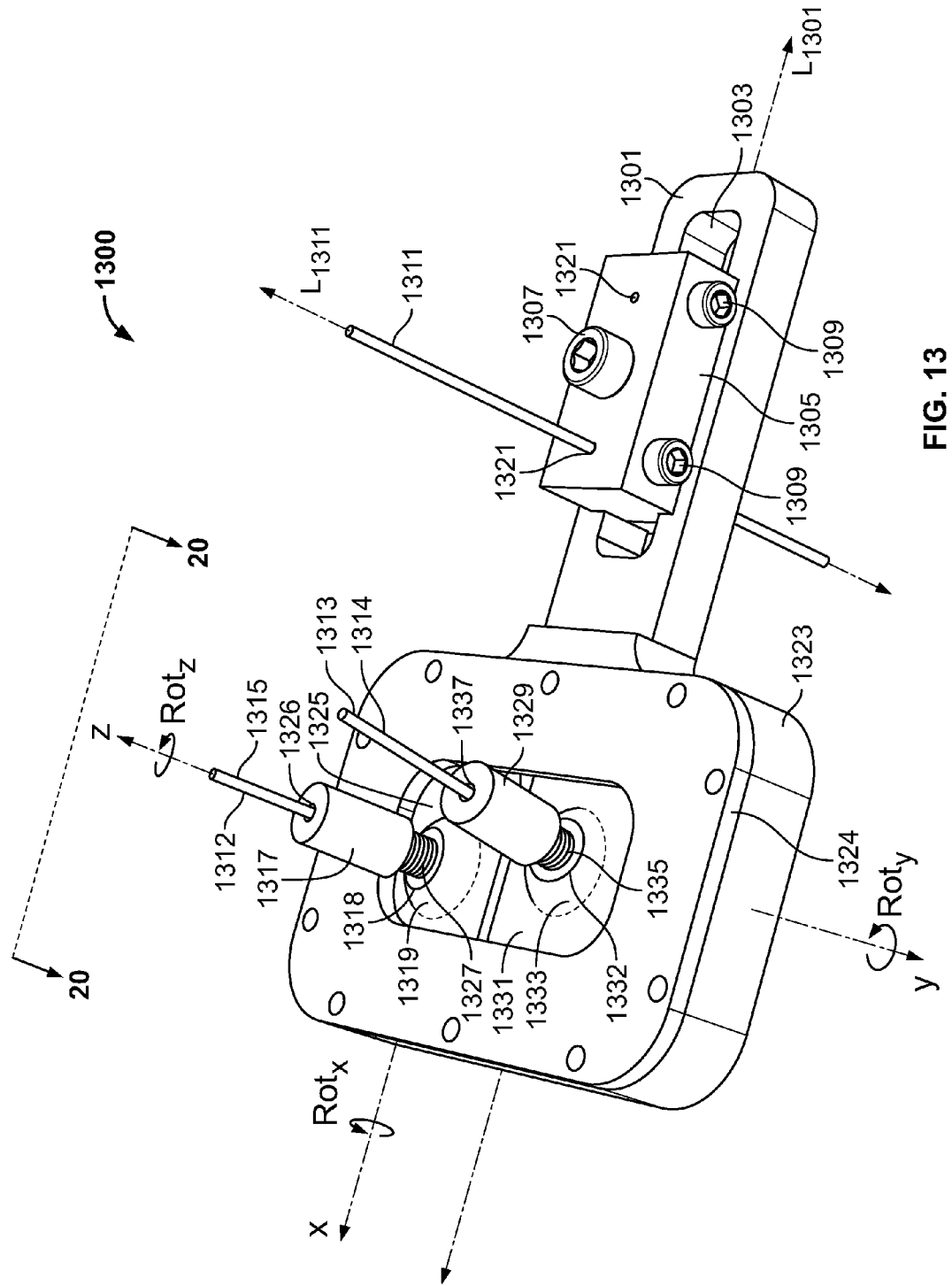
FIG. 13 shows still other apparatus in accordance with the principles of the invention.

FIG. 13 shows illustrative jig 1300. Jig 1300 may include a first bone fragment manipulator 1312. First bone fragment manipulator 1312 may include bone penetrating member 1315. Bone penetrating member 1315 may be secured to a bone segment such as bone segment Pa or bone segment Ph (shown in FIG. 3A). First bone fragment manipulator 1312 may include tube 1317. Tube 1317 may include receptacle 1326. Receptacle 1326 may receive bone penetrating member 1315.

Bone penetrating member 1315, when secured to a bone, may displace the bone segment along axes X, Y and Z. Bone penetrating member 1315, when secured to the bone segment may rotate the bone segment about axes X, Y and Z. Displacement or rotation of the bone segment may correspond to displacement or rotation of bone segment about an origin of the bone segment. Displacement or rotation of the bone segment may position the bone segment at an appropriate therapeutic position relative to a reference bone segment such as Pb (shown in FIG. 3A).

The first bone fragment manipulator 1312 may include collar support 1325. Collar support 1325 may be configured to translate in plane X-Y. Tube 1317 may include articulating surface 1319. Articulating surface 1319 may permit displacement and rotation of bone penetrating member 1315 about axes X, Y and Z. Articulating surface 1319 may articulate relative to collar support 1325.

Tube 1317 may rotate about axis Z. Tube 1317 may include outer threads 1327. Tube 1317 may threadedly engage female threaded member 1318. Female threaded member 1318 may include articulating surface 1319. Threaded engagement of tube 1317 and may displace tube 1317 relative to female threaded member 1318. Threaded engagement of tube 1317 and female threaded member 1318 may apply or relieve pressure on bone penetrating member 1315. Threaded engagement of tube 1317 and female threaded member 1318 may apply or relieve pressure on articulating surface 1319. Threaded engagement of tube 1317 and female threaded member 1318 may apply or relieve pressure on collar support 1325. Threaded engagement of tube 1317 and female threaded member 1318 may apply or relieve pressure on frame 1323. Frame 1323 may include frame cover 1324.

Pressure applied to bone penetrating member 1315, articulating surface 1319, collar support 1325 and frame 1323 may substantially fix a position of the bone segment secured to bone penetrating member 1315.

Jig 1300 may include second bone fragment manipulator 1314. Second bone fragment manipulator 1314 may have one or more features in common with first bone fragment manipulator 1312. For example, the second bone fragment manipulator may include bone penetrating member 1313, tube 1329, threads 1335, articulating surface 1333, collar support 1331 and female threaded member 1332.

Second bone fragment manipulator 1314 may displace or rotate a second bone segment such as bone segment Pa or Ph. Second bone fragment manipulator 1314 may substantially fix a position of the bone segment secured to bone penetrating member 1313. Second bone fragment manipulator 1314 may position the second bone segment relative to the first bone segment.

Jig 1300 may include base 1301. Base 1301 may include slider 1305. Slider 1305 may slide along axis L1301 in channel 1303. Set screw 1307 may set a position of slider 1305 along axis L1301. Slider 1305 may include receptacles 1321. Receptacles 1321 may receive bone penetrating member 1311. Bone penetrating member may have may have one or more features in common with bone penetrating members 1001, 1007 or 1023 (shown in FIG. 10).

Bone penetrating member 1311 may be secured to a reference bone segment such as segment Pb (shown in FIG. 3A). Slider 1305 and base 1301 may rotate about axis L1311. Rotation about axis L1311 may position the first and second bone segments relative to the reference bone segment. A position about axis L1311 may be substantially fixed by rotating set screw 1309. Rotation of set screw 1309 may apply or relieve pressure on bone penetrating member 1311.

Slider 1305 and base 1301 may translate along axis L1311. Translation along axis L1311 may position the first and second bone segments relative to the reference bone segment. For example, translation along axis L1311 may position the first and second bone segments at a volar tilt (shown in FIG. 9) or at a radial inclination (shown in FIG. 8). A position of slider 1305 relative to base 1301 along axis L1311 may be set by rotating set screw 1309. Rotation of set screw 1309 may apply or relieve pressure to base 1301.

Base 1301 may translate along axis L1301. Translation along axis L1301 may position the first and second bone segments relative to the reference bone segment. For example, translation along axis L1301 may position the first and second bone segments at a radial height (shown in FIG. 8). A position of base 1301 along axis L1301 may be set by rotating set screw 1307. Rotation of set screw 1307 may apply or relieve pressure on base 1301. A position of slider 1305 relative to base 1301 may be set by securing a bone penetrating member (not shown) to the reference bone via receptacle 1321.

Figure 14:
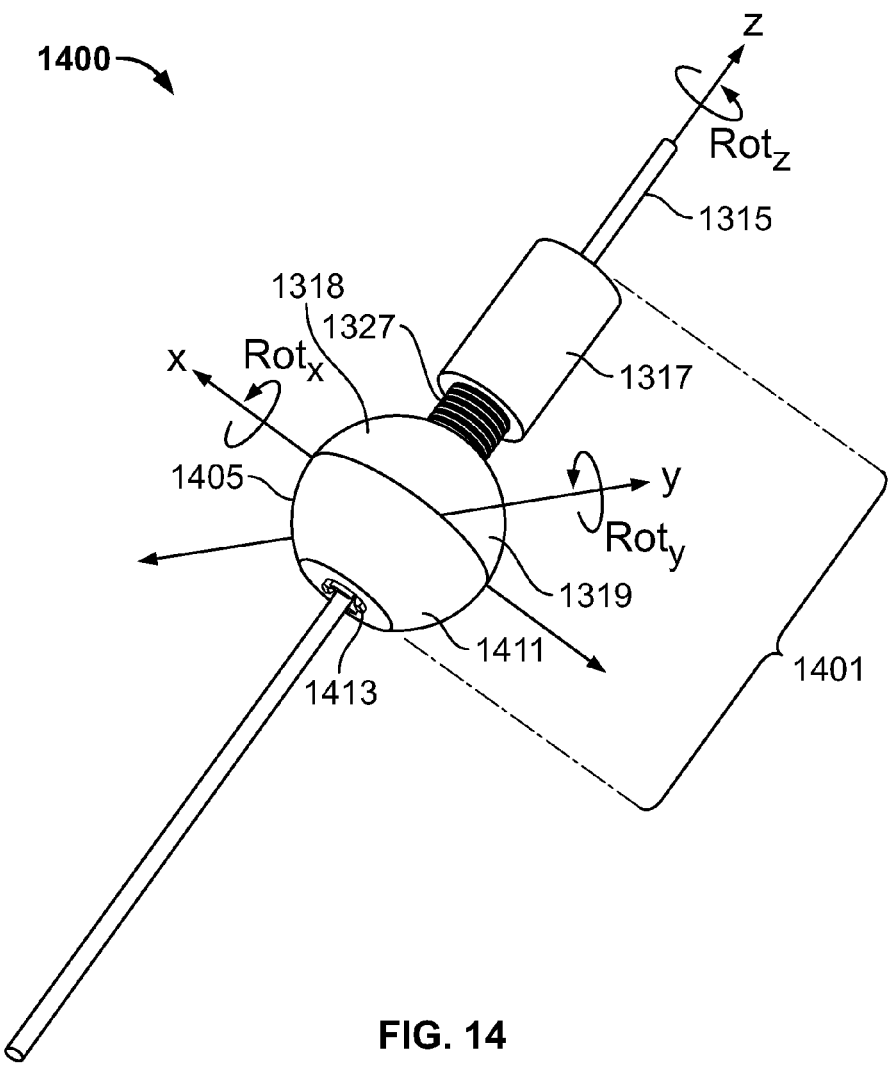
FIG. 14 shows a portion of the apparatus shown in FIG. 13.

FIG. 14 shows illustrative bone fragment manipulator 1400. Bone fragment manipulator 1312 or bone fragment manipulator 1314 may have one or more features in common with bone fragment manipulator 1400. Bone fragment manipulator includes collar 1401 and bone penetrating member 1315. Collar 1401 includes tube 1317. Tube 1317 may include a cannula for receiving bone penetrating member 1403. The cannula may have one or more features in common with receptacle 1326 (shown in FIG. 13). Tube 1317 includes outer threads 1327. Threads 1327 may engage female threaded member 1318. Female threaded member 1318 may include articulating surface 1319. Articulating surface 1319 may include a substantially spherically shaped portion.

Collar 1401 may include tapered form 1405. Tapered form 1405 may include articulating surface 1411. Articulating surface 1411 may include a substantially spherically shaped portion. Engagement of tube 1317 and tapered form 1405 may apply or relieve pressure on retention fingers 1413, for example, like a collet. Pressure applied to retention fingers 1413 may substantially fix a position of bone penetrating member 1315. Pressure applied to retention fingers 1413 may substantially fix a position of bone penetrating member 1315 along or about axis Z.

Articulating surfaces 1411 and 1319 may provide a freedom of movement to collar 1401 relative to collar support 1325. Articulating surfaces 1411 and 1319 may allow collar 1401 to freedom to translate and rotate about axes X, Y and Z. Articulating surfaces 1411 and 1319 may facilitate movement of a bone segment secured to bone fragment manipulator 1400 along and about three orthogonal axes.

Figure 15:
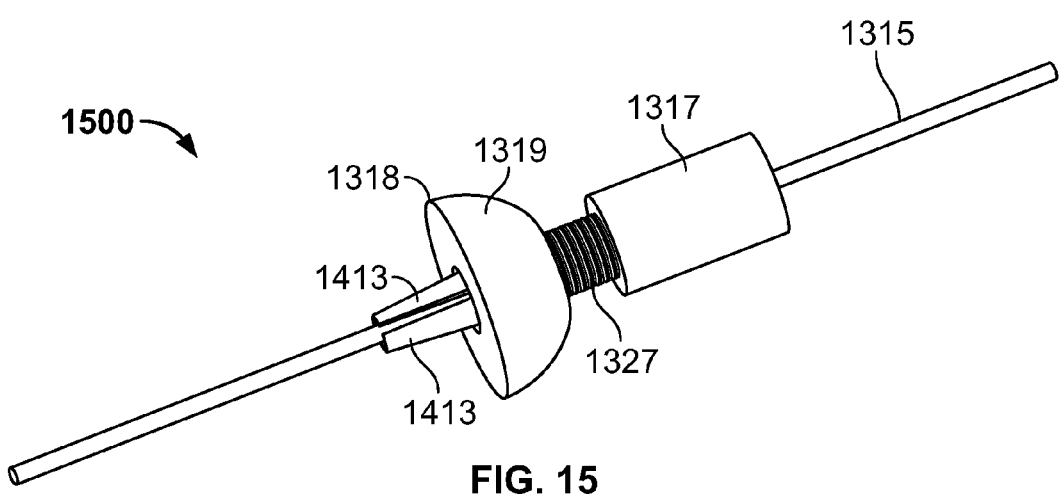
FIG. 15 shows a portion of the apparatus shown in FIG. 14.

FIG. 15 shows illustrative component 1500. Component 1500 may include tube 1317 threadedly engaged with female threaded member 1318. Component 1500 may include retention fingers 1413. Threaded engagement of tube 1317 and female threaded member 1318 may direct retention fingers 1413 into tapered form 1405 (shown in FIG. 14). Threaded engagement of tube 1317 and female threaded member 1318 may displace female threaded member 1318 relative to tapered form 1411.

Figure 16:
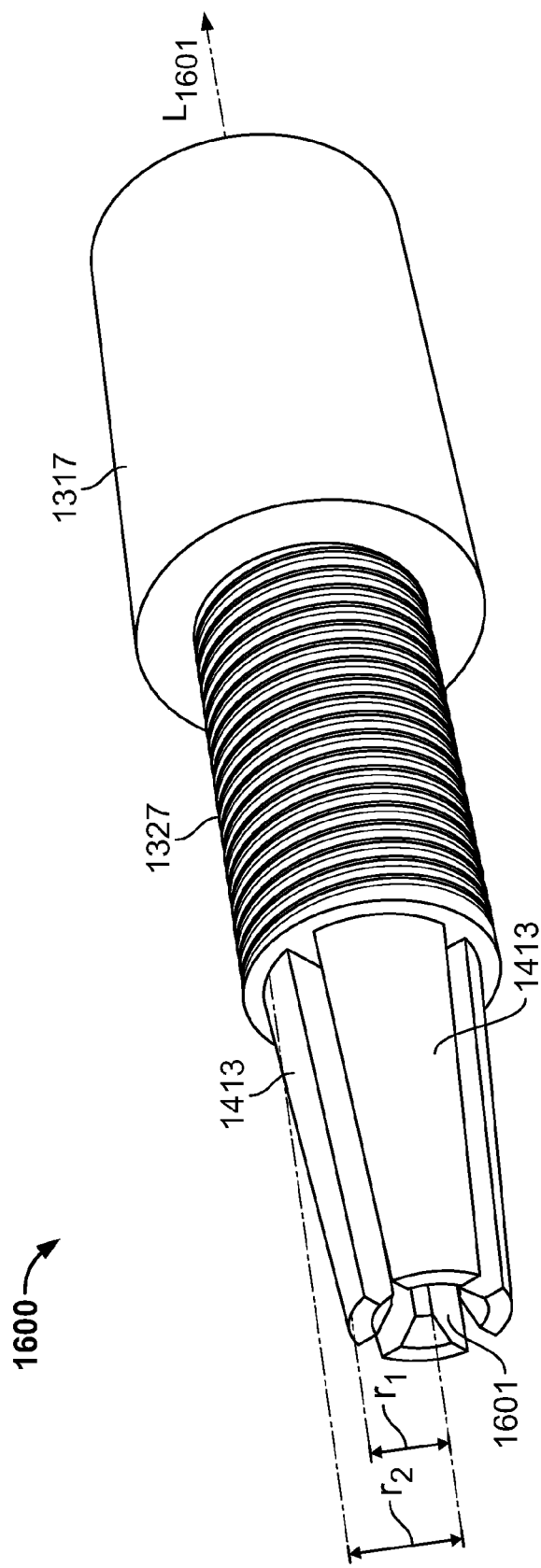
FIG. 16 shows a portion of the apparatus shown in FIG. 15.

FIG. 16 shows tube 1600. Tube 1600 may include one or more of the features of tube 1317. Tube 1600 may include cannula 1601. Cannula 1601 may be configured to receive bone penetrating member 1315.

Tube 1600 may include retention fingers 1413. Retention fingers 1413 may be associated with a first radius r1. Radius r1 may be measured with respect to a longitudinal axis L1601 that passes through a center of cannula 1601. Retention fingers 1413 may be associated with a second radius r2. Radius r2 may be measured with respect to a center of cannula 1601.

Radii r1 and r2 may define a taper associated with retention fingers 1413. Tapered form 1405 (shown in FIG. 14) may be configured to apply pressure to retention fingers 1413. The pressure may compress retention fingers 1413 against a bone penetration member inserted into cannula 1601.

Figure 17:
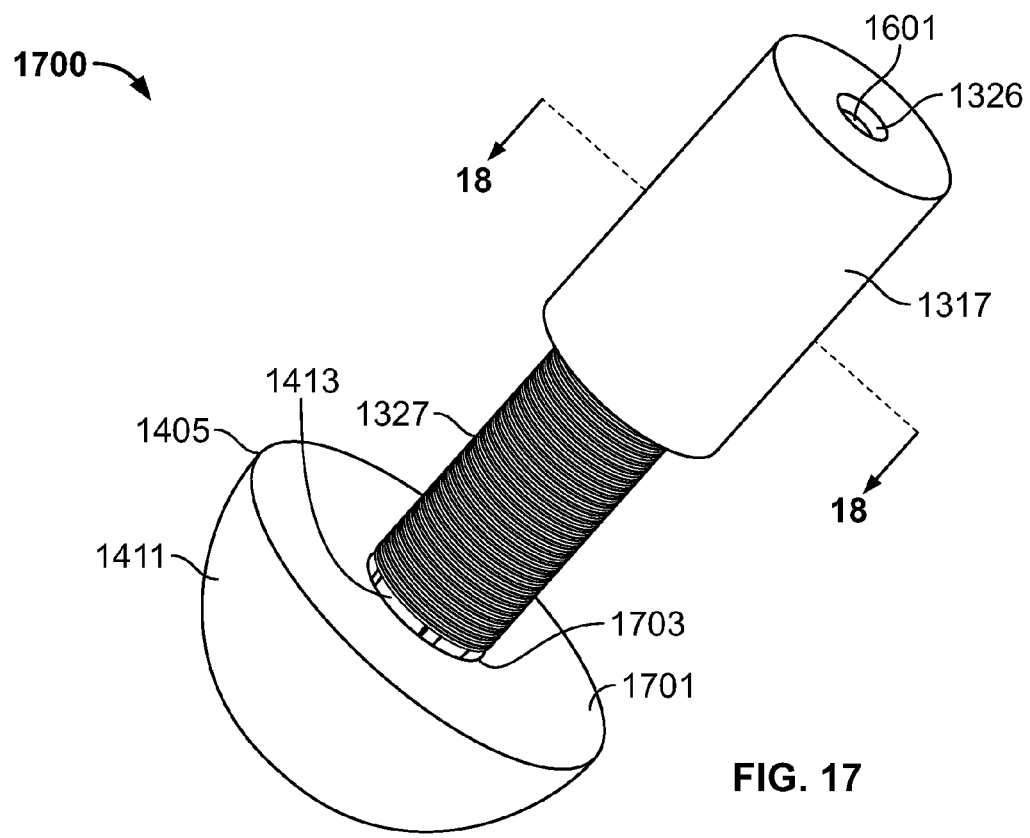
FIG. 17 shows a portion of the apparatus shown in FIG. 14.

FIG. 17 shows illustrative component 1700. Component 1700 may include tube 1317 and tapered form 1405. Tapered form 1405 may be configured to receive retention fingers 1413. Tapered form 1405 may include surface 1701.

Figure 18:
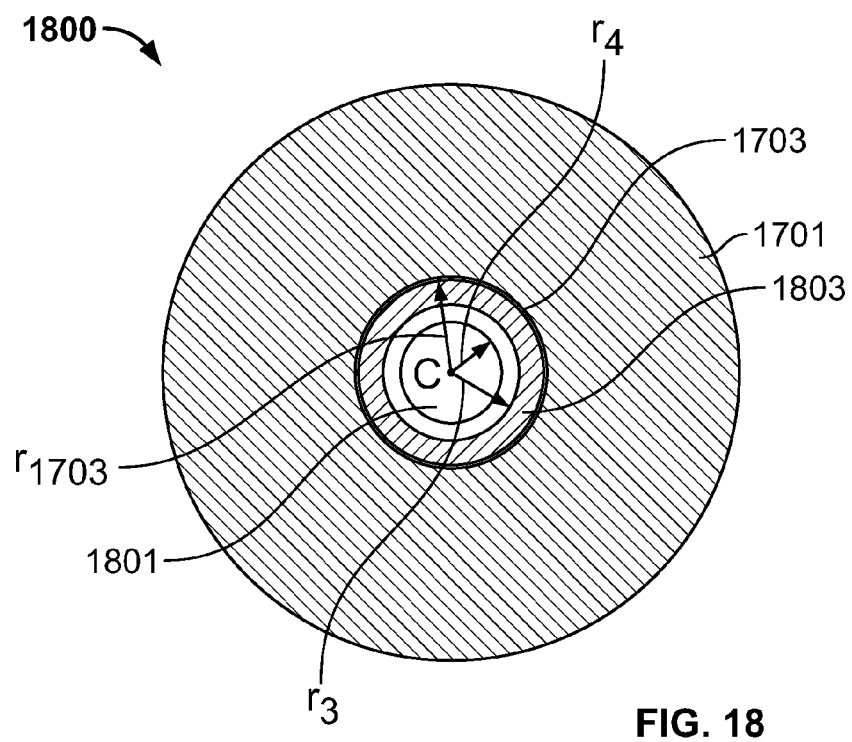
FIG. 18 shows a cross-sectional view, taken along lines 18-18 (shown in FIG. 17) of the apparatus shown in FIG. 17.

FIG. 18 is view of tapered form 1405 along lines 18-18 (shown in FIG. 17). Tapered form 1405 may include a cannula 1801. Cannula 1801 and cannula 1601 (shown in FIG. 16) may be concentric. Cannula 1801 may include a radius r3. Radius r3 may have a magnitude less than a magnitude of radius r2 (shown in FIG. 16). Radius r3 may form detent 1803. Detent 1803 may be configured to compress retention fingers 1413.

Radii r3 and r4 may define a taper. The taper defined by radii r3 and r4 may correspond to the taper defined by radii r1 and r2. The taper defined by radii r3 and r4 may be configured to compress retention fingers 1413.

Figure 19:
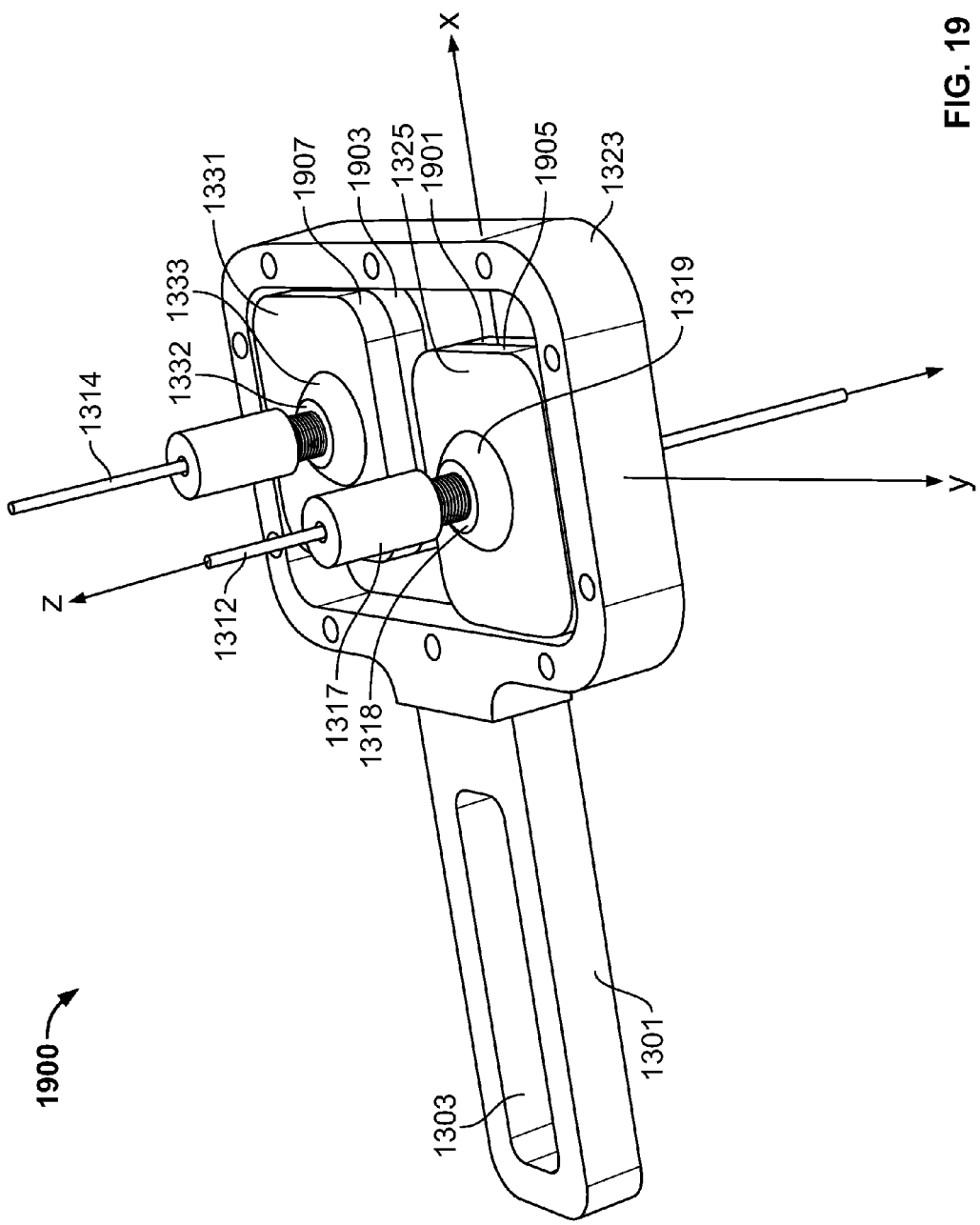
FIG. 19 shows another portion of the apparatus shown in FIG. 13.

FIG. 19 shows illustrative components 1900. Components 1900 may illustrate features of jig 1300 encapsulated by frame 1323.

Collar support 1325 may include upper plate 1905 and lower plate 1901. Articulating surface 1319 may be configured to articulate against upper plate 1905. Articulating surface 1411 (shown in FIG. 14) may be configured to articulate against lower plate 1901. Articulation against upper plate 1905 and lower plate 1901 may allow movement of bone fragment manipulator 1312 about and along axes X, Y and Z.

Upper plate 1905 may be displaced from lower plate 1901. Displacement of upper plate 1905 from lower plate 1901 may be constrained by frame 1323 (shown in FIG. 13). Displacement of upper plate 1905 from lower plate 1901 against frame 1323 may apply pressure to frame 1323.

Collar support 1331 may include upper plate 1907 and lower plate 1903. Upper plate 1907 and lower plate 1903 may have one or more features in common with upper plate 1905 and lower plate 1901, respectively. Bone fragment manipulator 1314 may have one or more features in common with bone fragment manipulator 1312.

Figure 20:
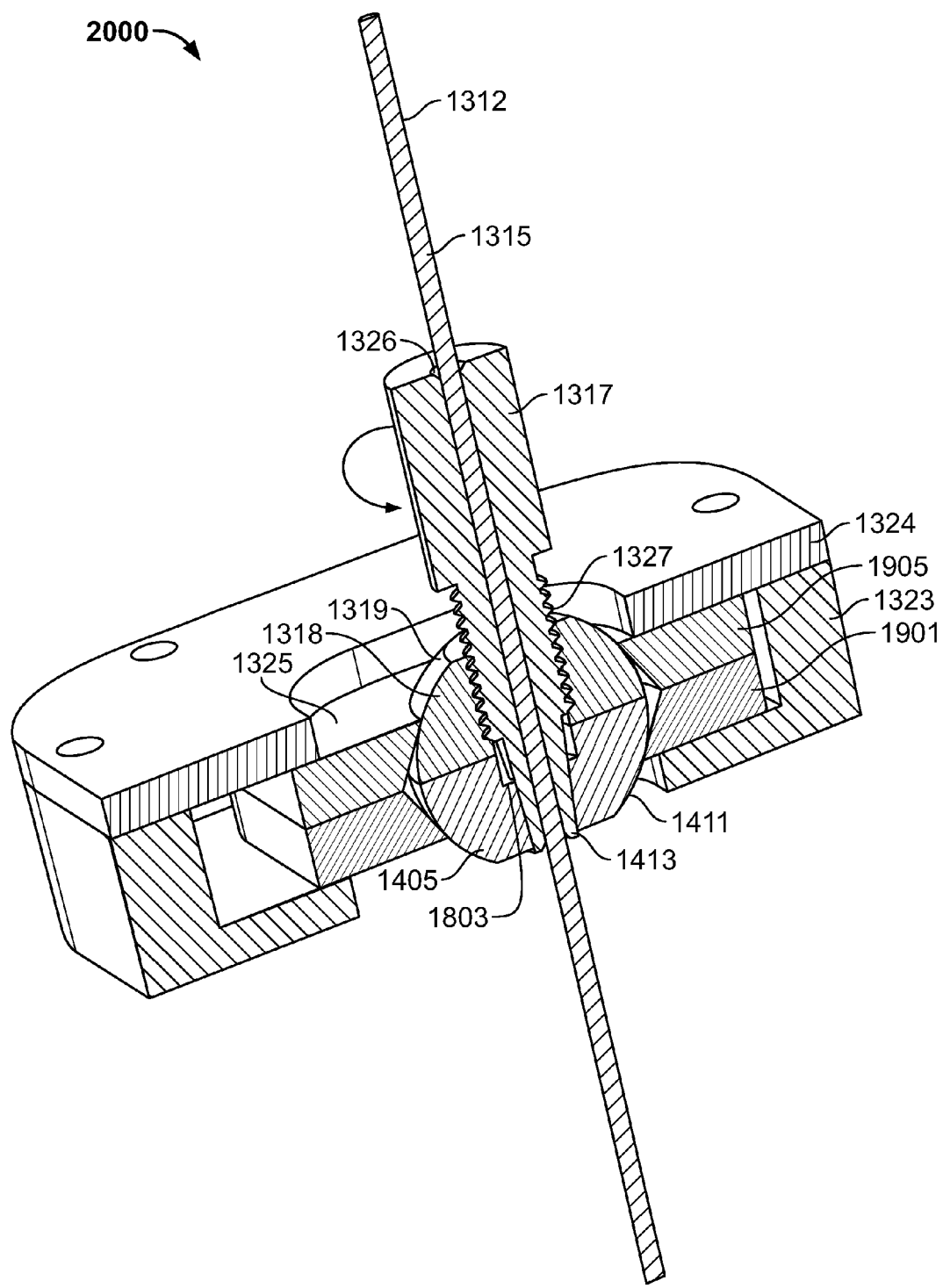
FIG. 20 shows a cross-sectional view, taken along lines 20-20 (shown in FIG. 13) of the apparatus shown in FIG. 13.

FIG. 20 shows illustrative cross-section 2000 taken along lines 20-20 (shown in FIG. 13). Outer threads 1327 may engage female threaded member 1318. Threaded engagement of tube 1317 and female threaded member 1318 may displace female threaded member 1318 from tapered form 1405. Threaded engagement of tube 1317 and female threaded member 1318 may displace tube 1317 relative to female threaded member 1318. Threaded engagement of tube 1317 and female threaded member 1318 may direct retention fingers 1413 into tapered form 1405.

In tapered form 1405, detent 1803 and cannula 1801 (shown in FIG. 18) may compress retention fingers 1413 against bone penetrating member 1315. Compression of retention fingers 1413 against bone penetrating member 1315 may substantially prevent movement of bone penetrating member 1315 within tube 1317.

Compression of retention fingers 1413 may be limited by bone penetrating member 1315. Expansion of retention fingers 1413 may be limited by detent 1803 and cannula 1801. Limits imposed by bone penetrating member 1315, detent 1803 and cannula 1801 may displace female threaded member 1318 from tapered form 1405. Displacement of female threaded member 1318 from tapered form 1405 may displace upper plate 1905 from lower plate 1901. Displacement of upper plate 1905 from lower plate 1901 may be limited by frame 1323.

Displacement of female threaded member 1318 from tapered form 1405 and displacement of upper plate 1905 from lower plate 1901 may generate pressure within frame 1323. Pressure within frame 1323 may fix a position of tube 1317 relative to collar support 1325. Pressure within frame 1323 may fix a position of collar support 1325 relative to frame 1323 (shown in FIG. 13). Pressure within frame 1323 may substantially prevent movement of bone manipulator 1312. Pressure within frame 1323 may fix a position of bone manipulator 1312. Pressure within frame 1323 may fix a position of a bone segment secured to bone manipulator 1312.

Figure 21:
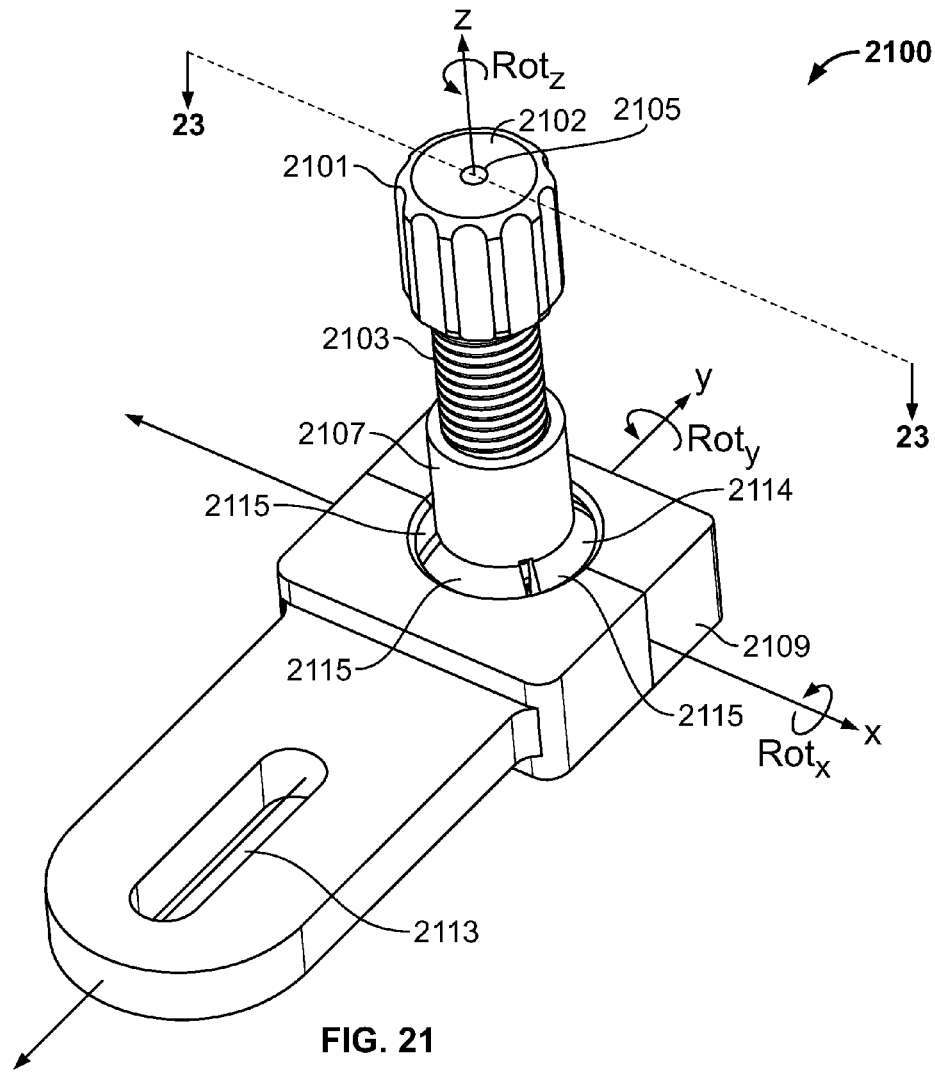
FIG. 21 shows yet other apparatus in accordance with the principles of the invention.

FIG. 21 shows illustrative component 2100. Component 2100 may include collar 2101. Collar 2101 may include tube 2102. Tube 2102 may include outer threads 2103. Collar 2101 may include female threaded member 2107. Collar 2101 may include receptacle 2105. Receptacle 2105 may be configured to receive a bone penetrating member such as bone penetrating member 1315 (shown in FIG. 13). The bone penetrating member may translate along axis Z. The bone penetrating member may rotate about axis Z. The bone penetrating member may be secured to a bone segment such as bone segments Pa or Ph (shown in FIG. 3A).

Collar 2101 may include tapered form 2114. Tapered form 2114 may include expansion members 2115. Expansion members may be configured to engage collar support 2109. Engagement of expansion members 2115 and collar support 2109 may fix a position of collar 2101 relative to collar support 2109. Engagement of expansion members 2115 and collar support 2109 may fix a position of a bone penetrating member relative to collar support 2109. Engagement of expansion members 2115 and collar support 2109 may fix a position of a bone segment relative to collar support 2109.

Expansion members 2115 may define a substantially spherically shape. Collar 2101 may be configured to translate along axes X, Y or Z. Collar 2101 may be configured to rotate about axes X, Y or Z.

Collar support 2109 may be configured to translate along axis Y. Collar support 2109 may be configured to translate along axis X. A set screw, such as set screw 1307 (shown in FIG. 13) may be inserted into channel 2113. Collar support 2109 may be configured to pivot about the set screw. The set screw may threadedly engage a base (not shown). The base may be secured to a reference bone segment, such as bone segment Pb (shown in FIG. 3A). The Threaded engagement of the set screw and the base may fix a position of collar support 2109 in plane X-Y.

Positioning collar support 2109 in plane X-Y may position a bone segment secured to collar support 2109 relative to the base. Positioning collar support 2109 in plane X-Y may position a bone segment secured to collar support 2109 relative to the reference bone segment secured to the base. Fixing a position of collar support 2109 relative to the base may reduce a fracture Fa or Fh (shown in FIG. 3A) in bone B.

Figure 22:
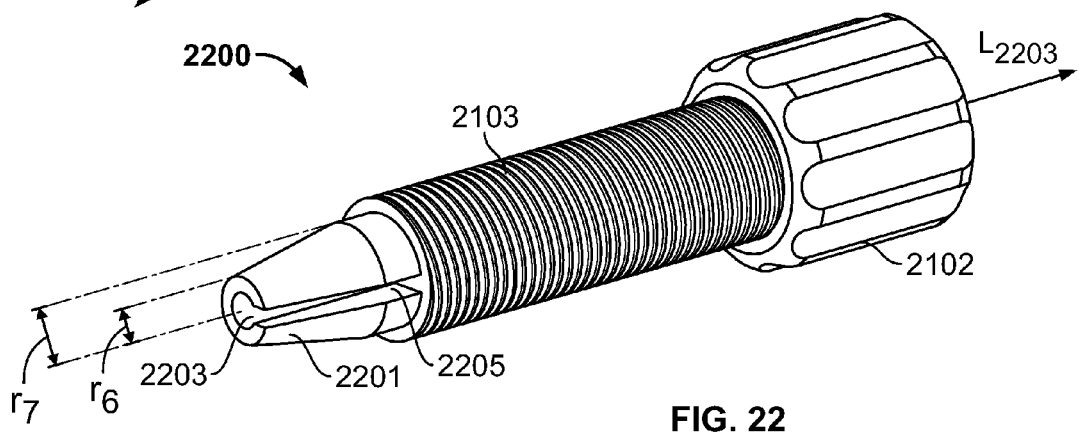
FIG. 22 shows a portion of the apparatus shown in FIG. 21.

FIG. 22 shows illustrative tube 2200. Tube 2200 may include outer threads 2103. Tube 2200 may include retention finger 2201. Retention finger 2101 may include radius r7. Radius r7 may be measured with respect to a longitudinal axis L2203 that passes through a center of cannula 2203. Retention finger 2201 may include radius r6. Radius r6 may be measured with respect to a center of cannula 2203. Radii r6 and r7 may define a taper associated with retention finger 2201.

Tube 2200 may include kerf cut 2205. Kerf cut 2205 may allow compression of expansion finger 2201 about axis L2203. Tapered form 2114 (shown in FIG. 21) may be configured to apply pressure to retention finger 2101 along the taper defined by r6 and r7. The pressure may compress retention finger 2101. The pressure may compress retention finger 2101 against a bone penetration member inserted into cannula 2203.

Figure 23:
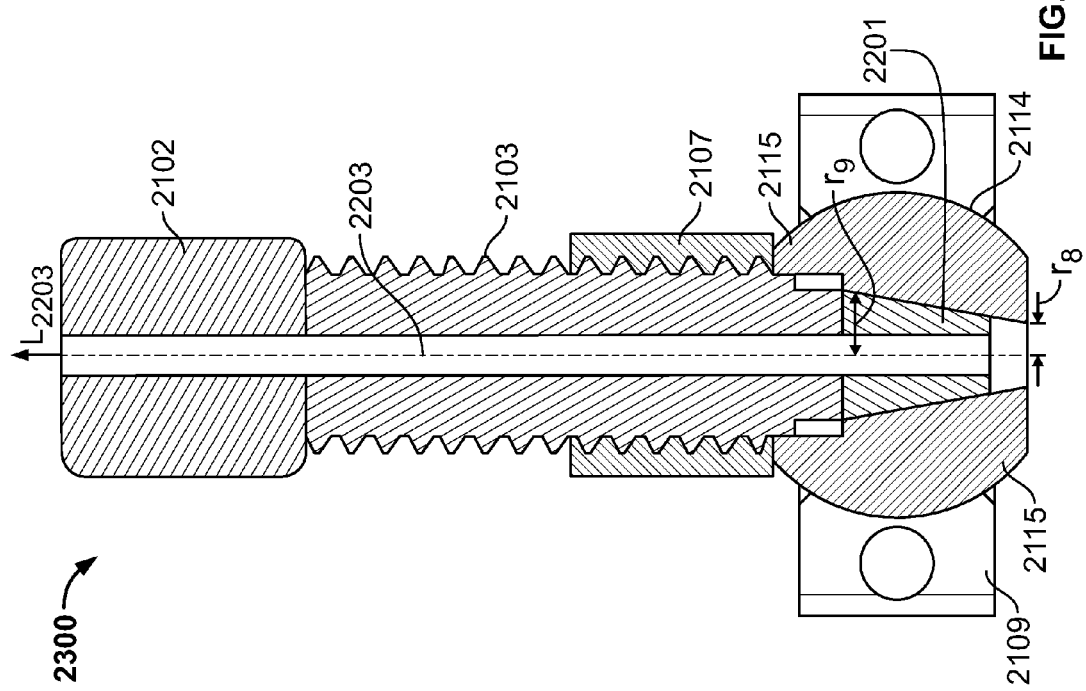
FIG. 23 shows a cross-sectional view, taken along lines 23-23 (shown in FIG. 21) of the apparatus shown in FIG. 21.

FIG. 23 shows a cross-section of component 2100 along lines 23-23 (shown in FIG. 21). Threaded engagement of outer threads 2103 and female threaded member 2107 may direct retention finger 2201 into tapered form 2114. Tapered form 2114 may include expansion members 2115. Tapered form may include radius r8. Tapered form may include radius r9. Radii r8 and r9 define a taper. The taper defined by radii r8 and r9 may be configured to compress retention finger 2201 about axis L2203 in response to threaded engagement of outer threads 2103 and female threaded member 2107.

Compression of retention finger 2201 about axis L2203 may apply pressure to a bone penetrating member inserted into cannula 2203. Compression of retention finger 2201 may be limited by the bone penetrating member.

Pressure applied by retention finger 2201 on the bone penetrating member and pressure applied by retention finger 2201 on taper form 2114 may expand expansion members 2115 against collar support 2109. Expansion of expansion members 2115 may be limited by collar support 2109. Pressure on the bone penetrating member and collar support 2109 may substantially fix a position of collar 2101. Pressure on the bone penetrating member and collar support 2101 may substantially fix a position of the bone penetrating member. Pressure on the bone penetrating member and collar support 2101 may substantially fix a position of a bone segment secured to the bone penetrating member.

Figure 24:
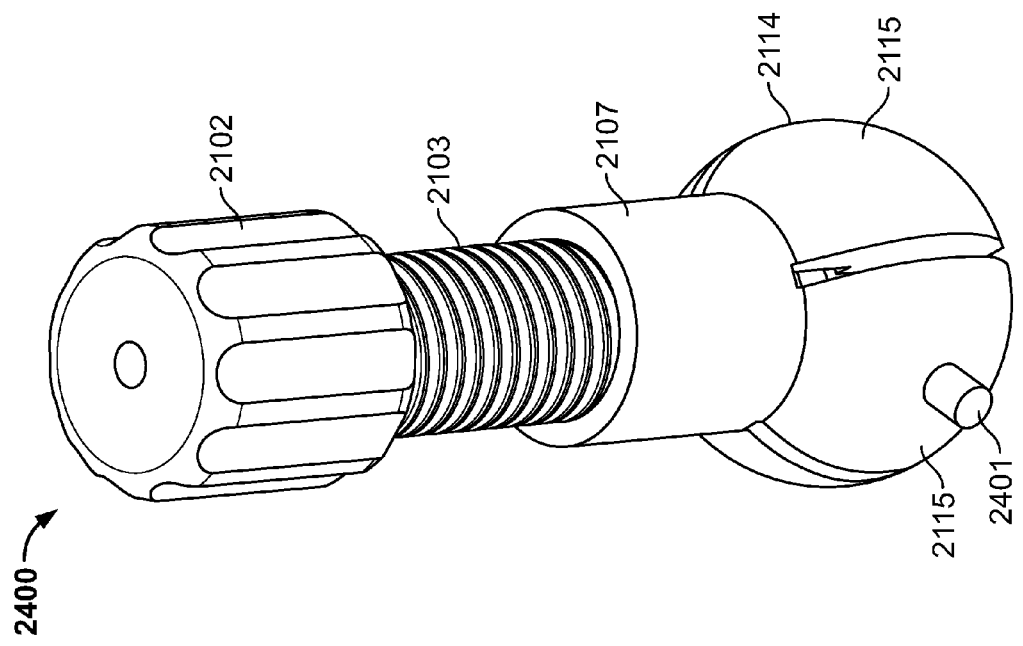
FIG. 24 shows a portion of the apparatus shown in FIG. 21.

FIG. 24 shows illustrative collar 2400. Collar 2400 may include one or more of the features of collar 2101 (shown in FIG. 21). Collar 2400 may include detent 2401. Detent 2401 may be affixed to expansion member 2115. Detent 2401 may be configured to resist movement of tapered form 2114.

Figure 25:
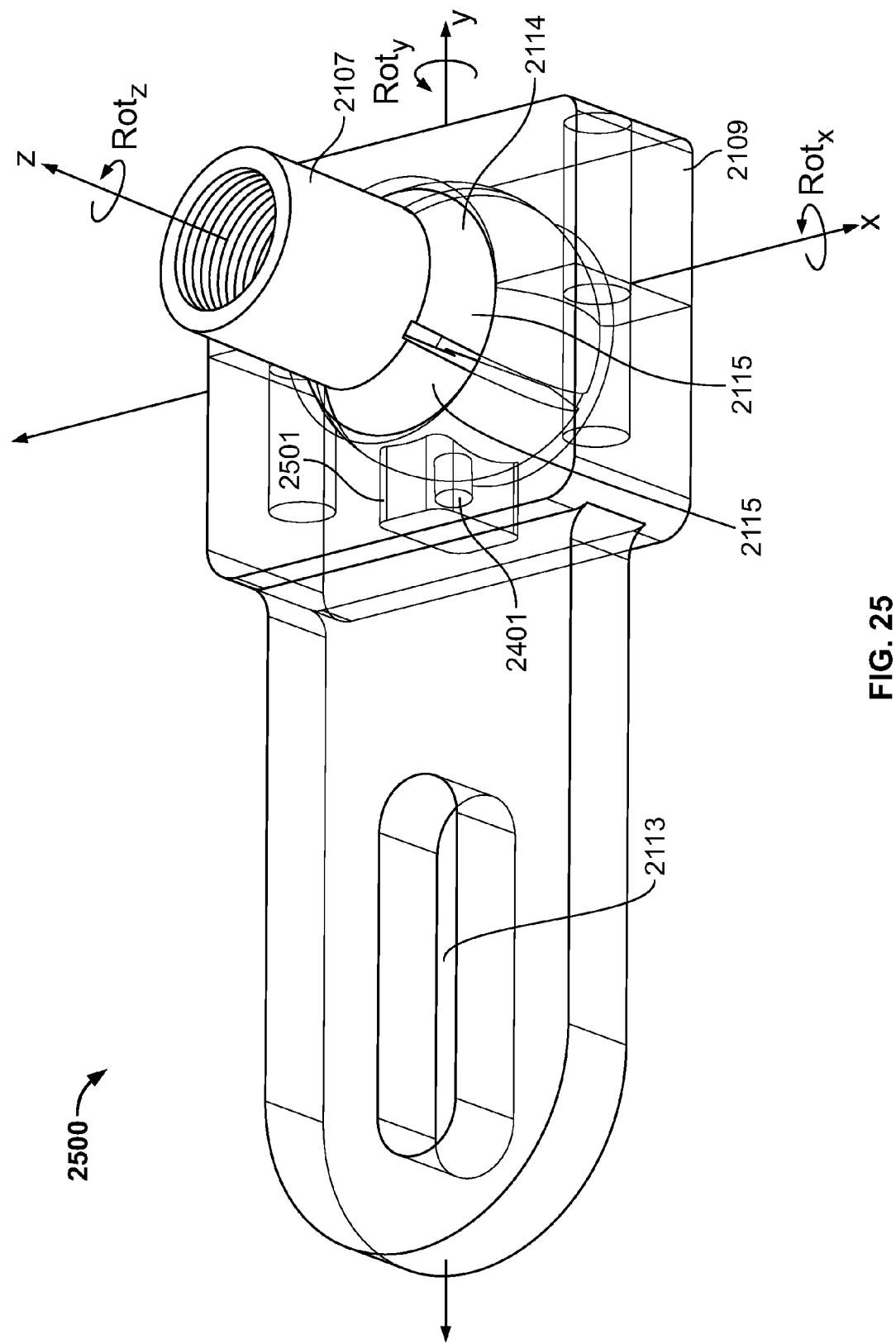
FIG. 25 shows a transparent view of a portion of the apparatus shown in FIG. 21.

FIG. 25 shows illustrative component 2500. Component 2500 may include female threaded member 2107, tapered form 2114, expansion member 2115 and collar support 2109. Expansion member 2115 may include detent 2401. Collar support 2109 may include enclosure 2501. Enclosure 2501 may be configured to limit movement of tapered form 2114 relative to collar support 2109.

Limited movement of tapered form 2114 may facilitate release of pressure within collar support 2109 in response to threaded engagement of tube 2102 and female threaded member 2107. Limited movement of tapered form 2114 may facilitate application of pressure within collar support 2109 in response to threaded engagement of tube 2102 and female threaded member 2107.

Figure 26:
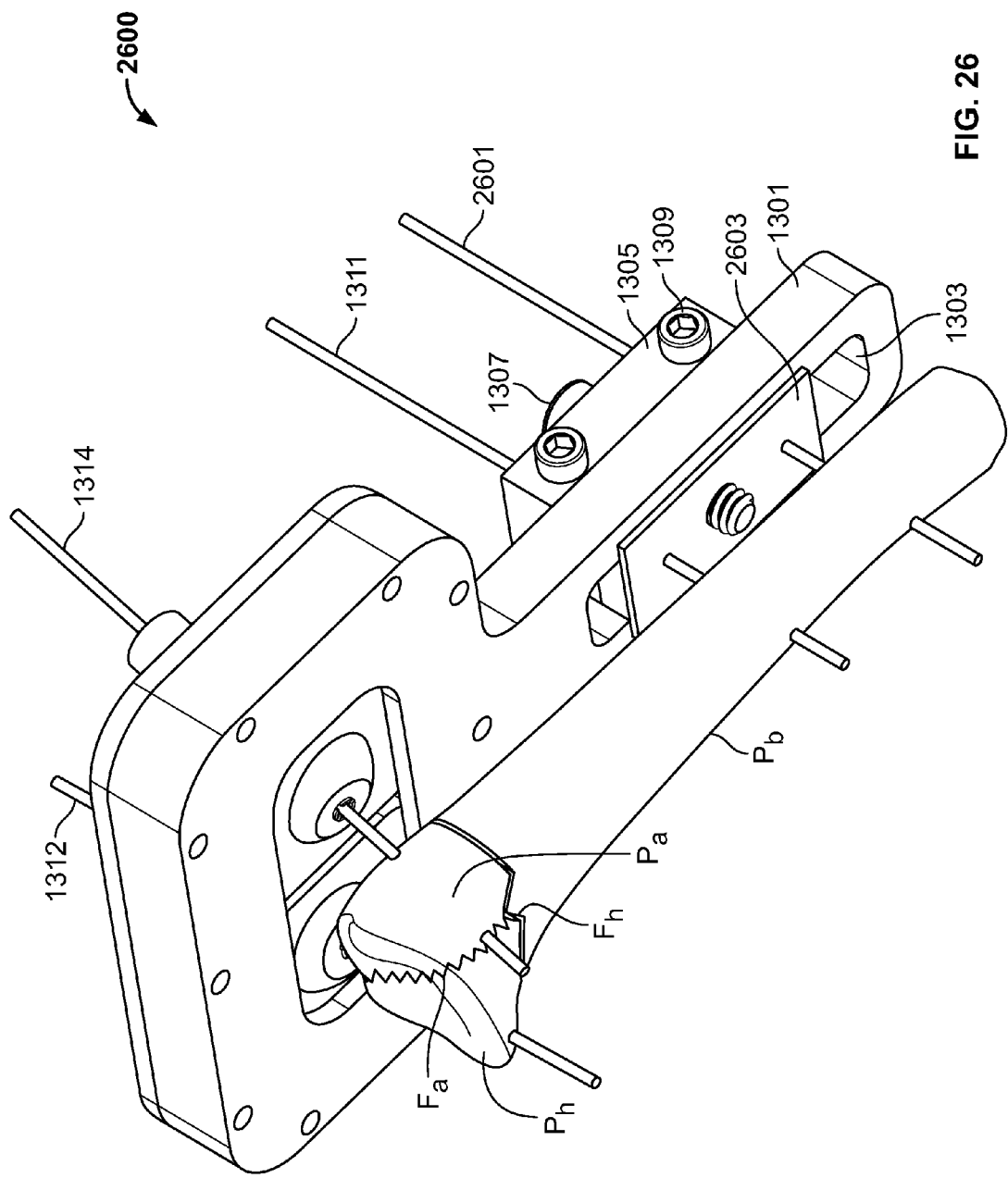
FIG. 26 shows the apparatus of FIG. 13 along with anatomy shown in FIG. 6.

FIG. 26 shows illustrative therapeutic scenario 2600. Bone fragment manipulator 1312 may be secured to bone segment Ph. Bone fragment manipulator may position bone segment Ph along three orthogonal axes. Bone fragment manipulator 1312 may position bone segment Ph by rotating bone segment Ph about three orthogonal axes. The three orthogonal axes may originate originating at an origin (shown in FIG. 7) of bone segment Ph. Bone segment Ph may be positioned relative to bone segment Pa. Bone segment Ph may be positioned relative to reference bone segment Pb. Bone fragment manipulator 1312 may lock a position of bone segment Ph relative to another bone segment.

Bone fragment manipulator 1314 may be secured to bone segment Pa. Bone fragment manipulator may position bone segment Pa along three orthogonal axes. Bone fragment manipulator 1314 may rotate bone segment Pa about three orthogonal axes. The three orthogonal axes may originate originating at an origin (shown in FIG. 7) of bone segment Pa. Bone segment Pa may be positioned relative to bone segment Ph. Bone segment may be positioned relative to reference bone segment Pb. Bone fragment manipulator 1314 may lock a position of bone segment Pa relative to another bone segment.

Slider 1305 may position bone segments Pa and Ph relative to reference bone segment Pb. Bone penetrating member 2601 may be inserted into receptacle 1321 (shown in FIG. 13) and secured to Pb. A position of slider 1305 along bone penetrating members 1311 and 2601 may be locked by rotating set screws 1309 and 1307.

Set screw 1307 may apply pressure to base 1301. Set screw 1307 may apply pressure by pressing slider 1305 and slider bottom 2603 against base 1301. The pressure may substantially fix a position of sider 1305 and slider bottom 2603. The pressure may substantially fix a position of base 1301 relative to Pb. The pressure may substantially fix a position of bone segments Pa and Ph relative to Pb.

Bone segments Pa, Ph and Pb may be locked at a therapeutic distances from each other. Locking a position of bone segments Ph, Pa and Pb may reduce fractures Fh and Fa.

Figure 27:
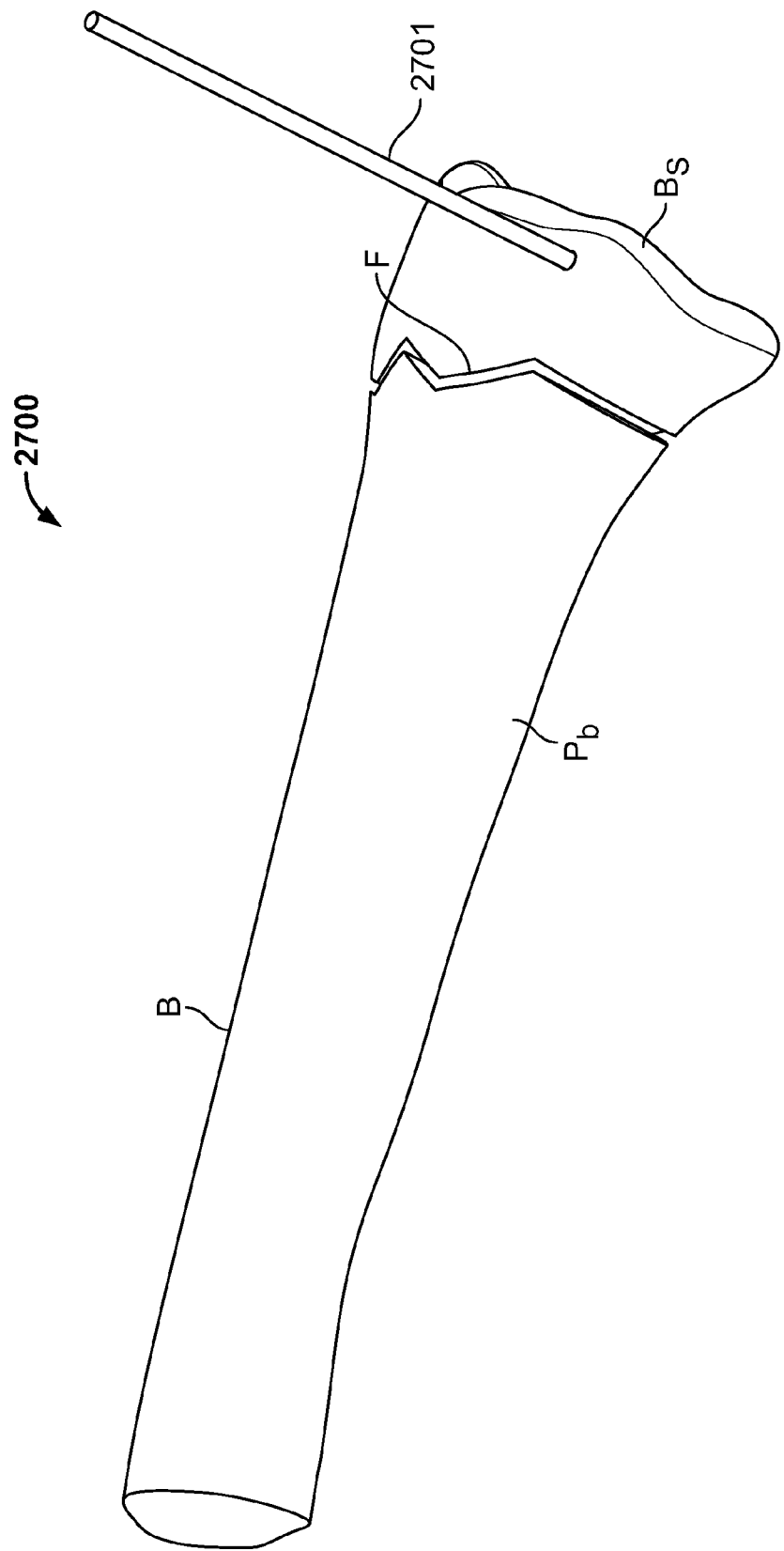
FIG. 27 shows yet other apparatus in accordance with the principles of the invention along with a portion of the anatomy shown in FIG. 8.

FIG. 27 shows illustrative clinical step 2700. Clinical step 2700 may include drilling bone penetrating member 2701 into bone segment Bs. Bone segment Bs may be separated from reference bone segment Pb by fracture F. Bone penetrating member 2701 may be drilled into a location on bone segment Bs. The location may be identified based on an anatomical feature of bone segment Bs. The location may be identified based on a target site interior to bone B. The target site may correspond to a target location of an implant inserted into bone B to repair fracture F. The location may be identified based on sites H' or I' on bone B.

Figure 28:
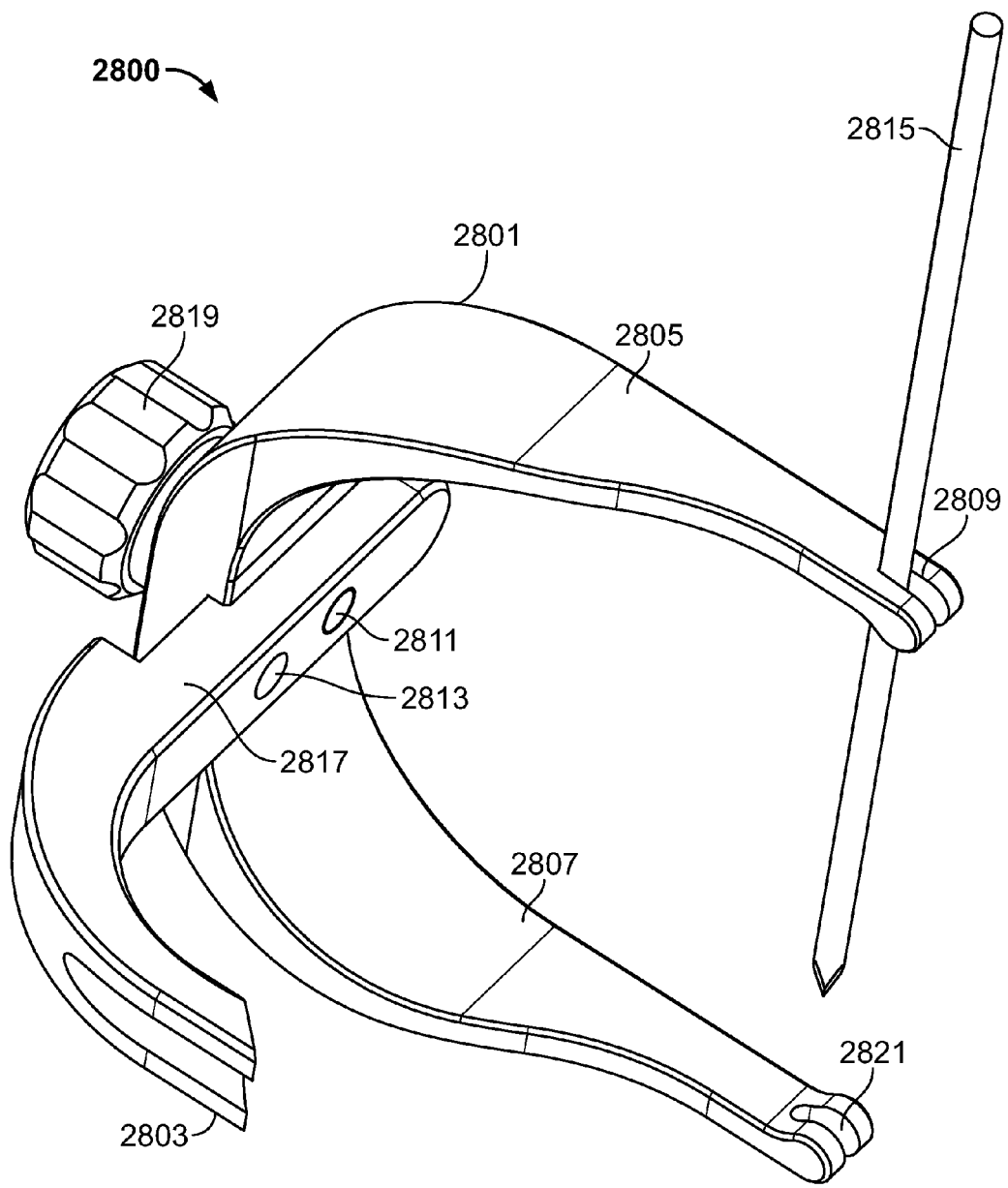
FIG. 28 shows yet other apparatus in accordance with the principles of the invention.

FIG. 28 shows illustrative apparatus 2800. Apparatus 2800 may include pin 2815. Pin 2815 may have one or more features in common with bone penetrating member 2701. Apparatus 2800 may include support 2801. Support 2801 may include extension 2805, extension 2817 and extension 2807. A configuration of extension 2817 relative to extensions 2805 and 2807 may be adjusted using set screw 2819 and receptacles 2811 and 2813.

Support 2801 may be configured to articulate relative to pin 2815. Support 2801 may include concave surface 2809. Support 2801 may include concave surface 2821. Concave surface 2809 may be configured to articulate against pin 2815. Concave surface 2821 may be configured to articulate against pin 2815.

Bone B (shown in FIG. 27) may be a radius. When bone B is a radius on a right side of skeleton S (shown in FIG. 1), concave surface 2809 may be configured to articulate against pin 2815. When bone B is a radius on a left side of skeleton S, concave surface 2821 may be configured to articulate against pin 2815.

Support 2801 may include indicator 2803. Support 2801 may span from a first anatomical aspect of bone B to a second anatomical aspect of bone B. The first anatomical aspect may correspond to a location of pin 2815 on bone B (see FIG. 27). Concave surface 2809 or 2821 may be positioned at the first anatomical aspect. Indicator 2803 may be positioned at the second anatomical aspect. When bone B is a radius, support 2801 may span from a dorsal aspect of bone B (shown in FIG. 3A) to a medial aspect of bone B (shown in FIG. 3A).

Articulation of concave surface 2809 or 2821 against pin 2815 may position indicator 2803 proximate to an anatomical aspect of bone B. In a position proximate to the anatomical aspect of bone B, indicator 2803 may point to an access point on bone B.

The access point may correspond to site H' or site I' (shown in FIG. 3A). The access point may be based on a target site interior to bone B. The target site may correspond to target location of an implant configured to repair fracture F.

Figure 29:
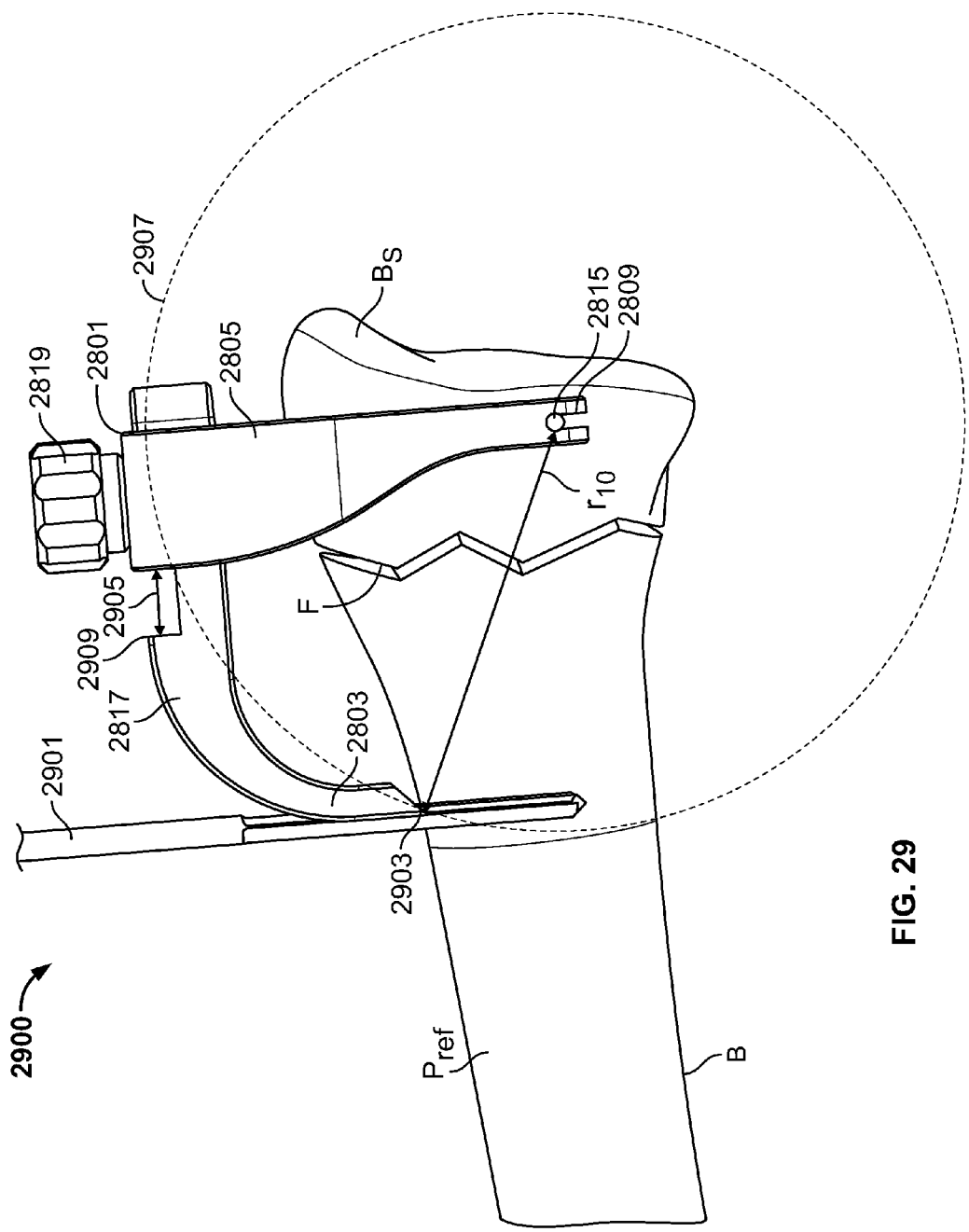
FIG. 29 shows the apparatus of FIG. 28, along with other apparatus and a portion of the anatomy shown in FIG. 8.

FIG. 29 shows illustrative therapeutic scenario 2900. In scenario 2900 support 2801 is mutually engaged with pin 2815. Support 2801 and pin 2815 when mutually engaged may define spherical surface 2907. Spherical surface 2907 may be centered at pin 2815 and include radius r10. Indicator 2803 may be configured to identify access point 2903. Access point 2903 may be positioned at an intersection of spherical surface 2907 and soft tissue (not shown) adjacent to bone B.

Support 2801 may be configured to identify an access point corresponding to an implant having a first length. Support 2801 may be configured to indicate an access point for an implant having a second length. The implant may be configured to repair fracture F in bone B.

For an implant having the first length, support 2801 may be configured to define a spherical surface characterized by radius r10. When support 2801 is configured to define a spherical surface characterized by radius r10, extension 2817 may be positioned a distance 2905 from detent 2909.

For an implant having the second length, support 2801 may be configured to define a spherical surface characterized by radius smaller in magnitude than radius r10. When support 2801 is configured to indicate an access point for an implant having the second length, extension 2817 may be positioned substantially adjacent to detent 2909.

Extension 2817 may be positioned relative to detent 2909 using set screw 2819. Set screw 2819 may be secured using receptacle 2811 (shown in FIG. 28) for an implant having the first length. Set screw 2819 may be secured using receptacle 2813 (shown in FIG. 28) for an implant having the second length.

Drill 2901 may be positioned adjacent to indicator 2803. Drill 2901 may penetrate bone B at access point 2903.

Figure 30:
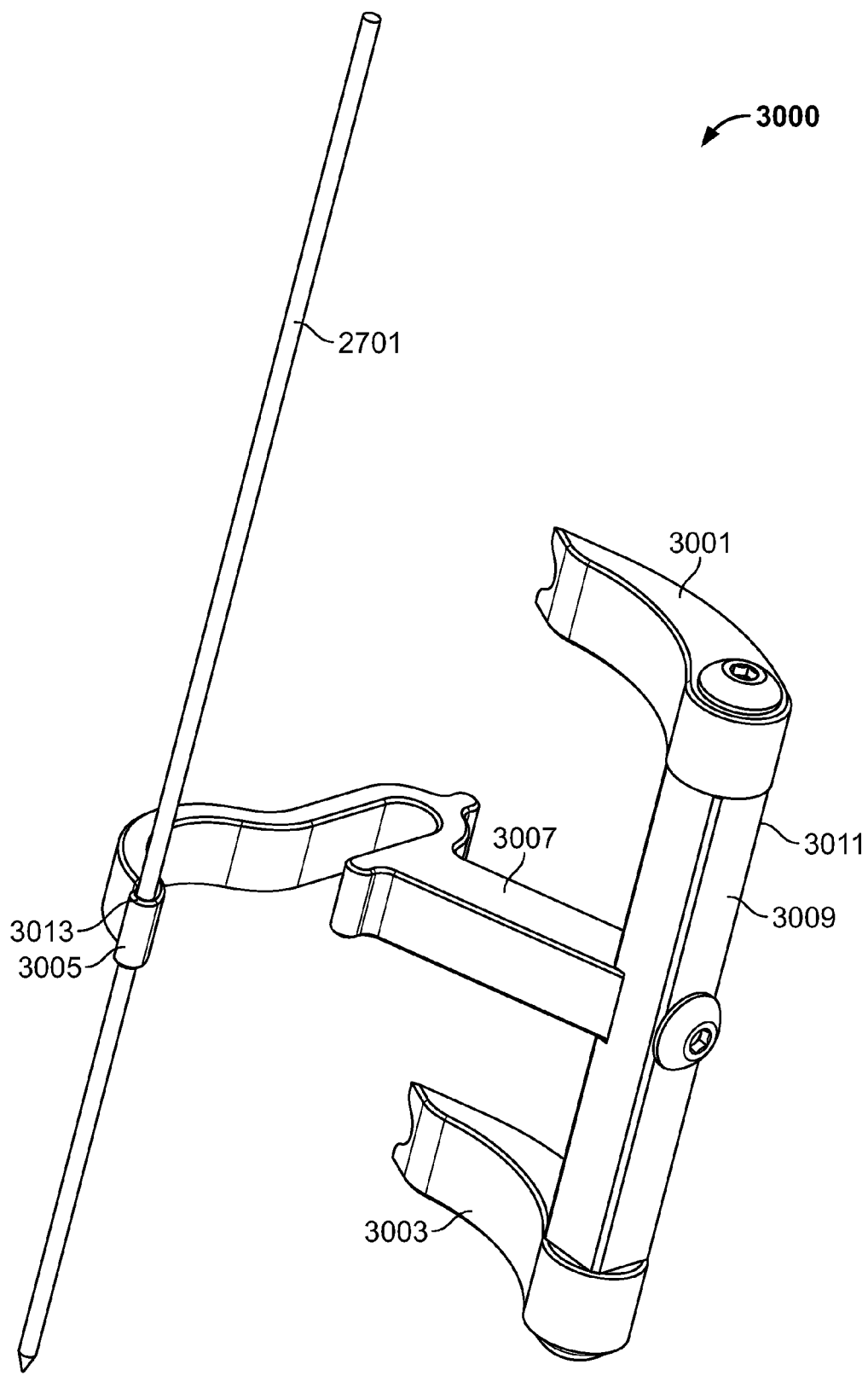
FIG. 30 shows yet other apparatus in accordance with the principles of the invention along with apparatus shown in FIG. 27.

FIG. 30 shows illustrative apparatus 3000. Apparatus 3000 may include one or more of the features of apparatus 2800. Apparatus 3000 may include support 3011. Support 3011 may include extensions 3001, 3009, 3003 and 3007.

Apparatus 3000 may include bushing 3005. Bushing 3005 may include cannula 3013. Cannula 3013 may receive pin 2701. Cannula 3013 may define a concave surface of bushing 3005. Pin 2701 may articulate against the concave surface of bushing 3005. Support 3011 may articulate relative to pin 2701. A support that includes bushing 3005 for receiving pin 2701 may limit movement of support relative to pin 2701. Limited movement of support relative to pin 2701 may reduce measurement error in determining an access point of a target site interior to bone B.

Figure 31:
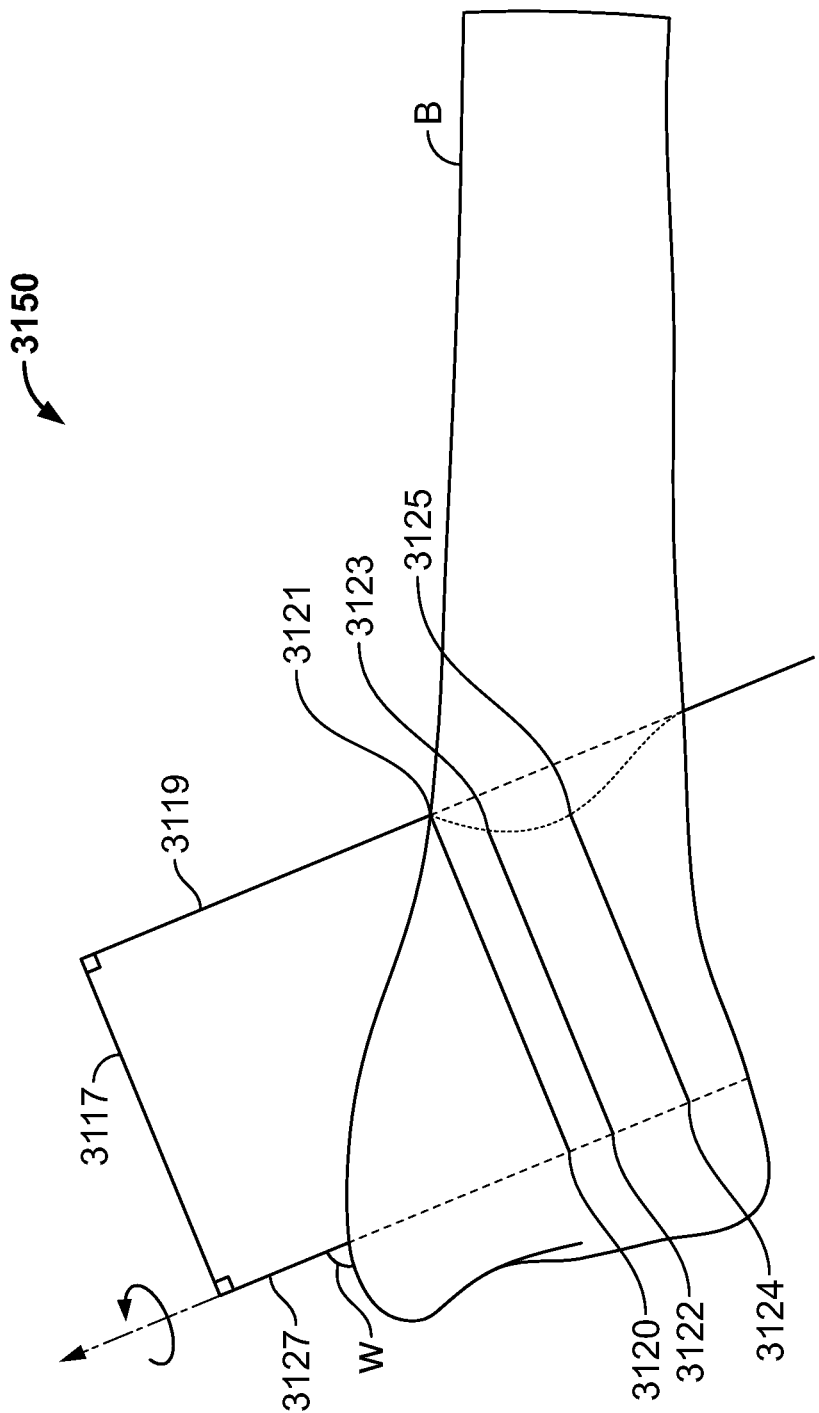
FIG. 31 shows information in accordance with the principles of the invention.

FIG. 31 shows schematic model 3150. Model 3150 illustrates principles that may embodied in apparatus 3000 (shown in FIG. 30). Model 3150 shows points 3120, 3122 and 3124. Points 3120, 3122 and 3124 may be interior to bone B. Each of points 3120, 3122 and 3124 may correspond to a location for a bone implant such as implant 300 (shown in FIG. 3B).

Each of points 3120, 3122 and 3124 may lie on line 3127. Line 3127 may correspond to a pin, such as pin 2701 (shown in FIG. 27), fixed at an angle w relative to bone B.

Line 3117 may represent a uniform distance. Line 3117 may represent a length of a bone implant, such as implant 300. Line 3117 may be fixed at an orientation orthogonal to line 3127. Line 3117 may represent a pointer fixed orthogonally to line 3127. Line 3117, when fixed orthogonally to line 3127 identifies points spaced apart from line 3127 by uniform distance 3117.

Line 3119 may be fixed orthogonally to line 3117. Rotation of line 3119 about line 3127 at a distance 3117 from line 3127 may identify sites on bone B spaced apart from line 3127 by distance 3117. Line 3119 may represent an engagement element that identifies points, such as points 3121, 3123 and 3125 on a convex surface of bone B a distance 3117 from line 3127. A point of intersection of line 3119 and bone B may represent an access point, such as H' or I' (shown in FIG. 3A) on bone B.

A change in angle w may cause line 3119 to identify points different from points 3121, 3123 or 3125, but the points will remain at distance 3117 from line 3119.

Figures 32, 33:
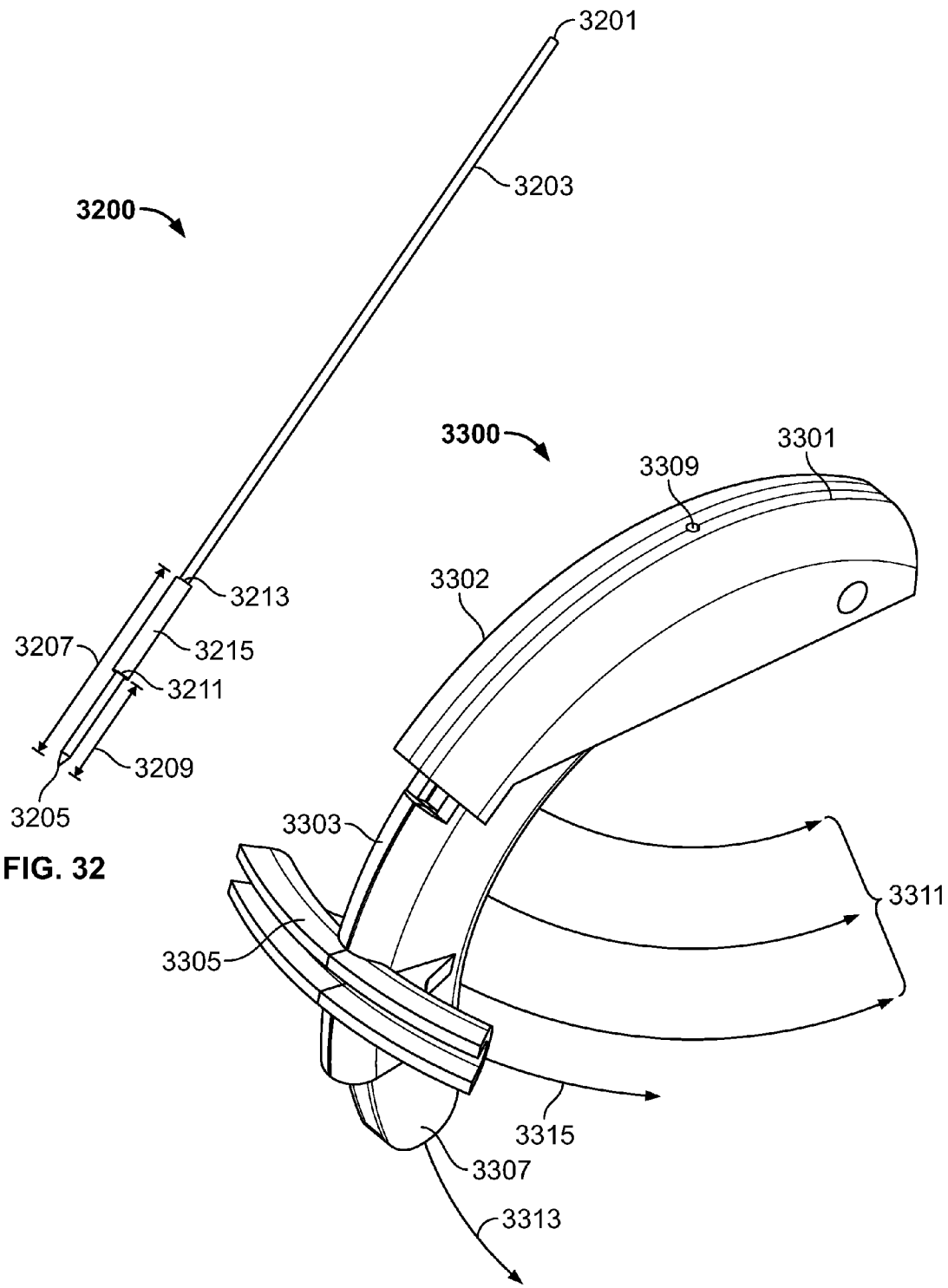
FIG. 32 shows yet other apparatus in accordance with the principles of the invention.
FIG. 33 shows yet other apparatus in accordance with the principles of the invention.

FIG. 32 shows illustrative pin 3200. Pin 3200 may include one or more of the features of pin 2701. Pin 3200 may include collar 3215. Collar 3215 may include detent 3211. Collar 3215 may include detent 3213.

Detent 3211 may define a maximum penetration of end 3205 into bone segment Bs (shown in FIG. 27). The maximum penetration may correspond to distance 3209. Detent 3213 may define a minimum elevation of support 3011 or support 2801 above bone segment Bs. The minimum elevation may correspond to distance 3207.

FIG. 33 shows illustrative apparatus 3300. Apparatus 3300 may include support 3302. Support 3302 may include fixture 3301. Fixture 3301 may include receptacle 3309. Receptacle 3309 may be configured to receive pin 3203 (shown in FIG. 32). Receptacle 3309 may be configured to receive pin 2701 (shown in FIG. 27). Support 3300 may articulate against the pin received by receptacle 3309. Support 3300 may pivot about the pin received by receptacle 3309. Support 3300 pivot about the pin and sweep out spherical surface 3311.

Support 3300 may include extension 3303. Extension 3302 may be configured to extend along spherical trajectory 3313. Extension 3303 may extend along rail 3307.

Extension 3303 may include indicator 3305. Indicator 3305 may be configured to indicate an access point. The access point may correspond to an intersection of spherical surface 3311 and soft tissue adjacent to bone B.

Indicator 3305 may extend away from extension 3303 along spherical trajectory 3315. Trajectory 3315 may be orthogonal to trajectory 3313. Extension 3303 may extend along trajectory 3313 until extension 3303 contacts soft tissue adjacent to bone B. Extension 3303 may extend along trajectory 3313 until indicator 3305 contacts soft tissue adjacent to bone B. Indicator 3305 may indicate an access point for inserting an implant into bone B at a target site.

Figure 34:
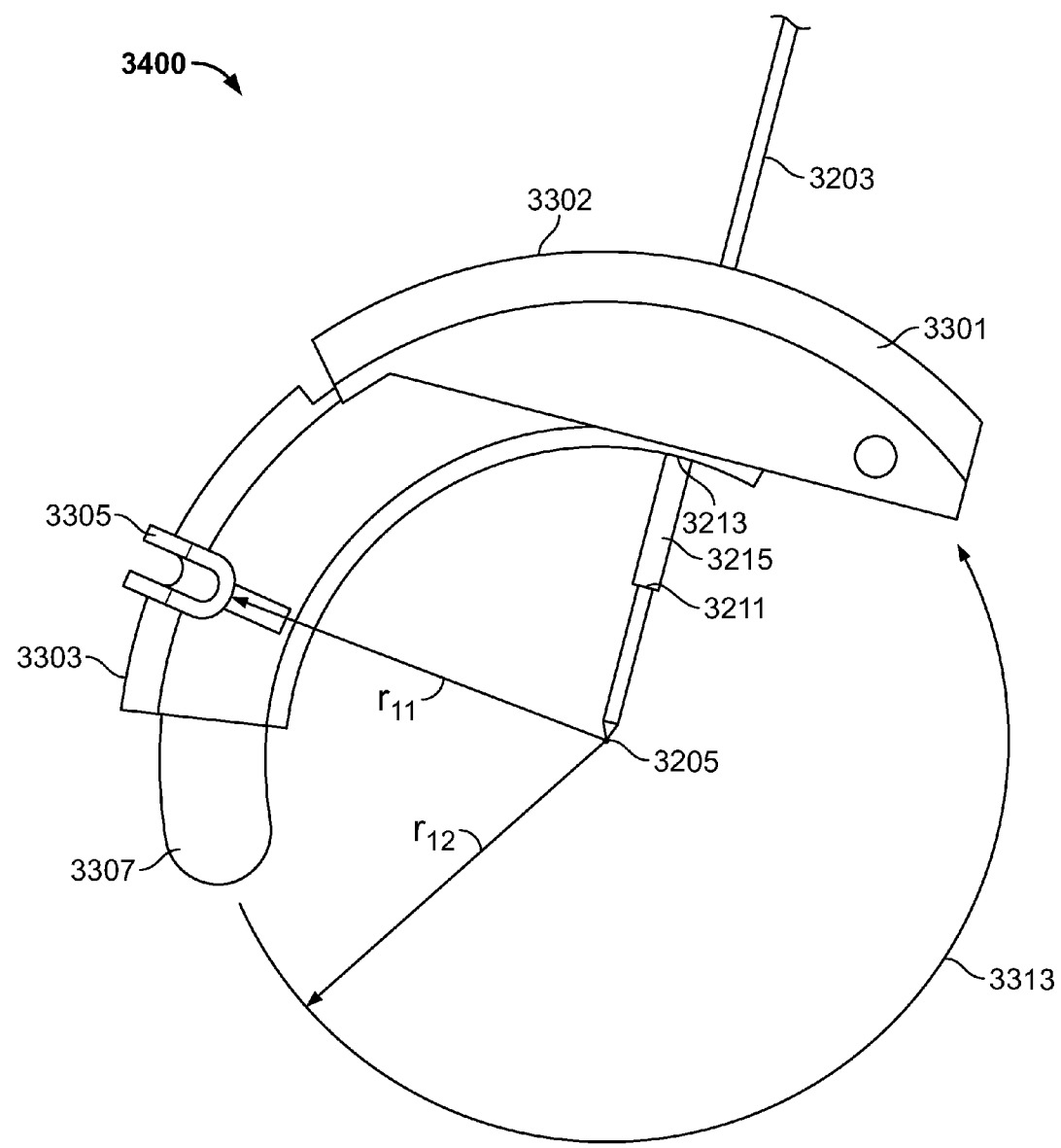
FIG. 34 shows the apparatus of FIGS. 32 and 33.

FIG. 34 shows illustrative apparatus 3400. Apparatus 3400 may have one or more features in common with apparatus 3300. Pin 3203 may be secured to a bone segment such as bone segment Pa, Ph, Pb (shown in FIG. 3A) or Bs (shown in FIG. 27). Detent 3211 may define a minimum elevation of fixture 3301 relative to the bone segment. Detent 3213 may define a maximum elevation 3207 of fixture 3301 above the bone segment.

Pin 3203 and support 3302 may be configured such that indicator 3305 points to an access point along spherical trajectory 3315 (shown in FIG. 33). Pin 3203 and support 3302 may be configured such that a target site for an implant may correspond to end 3205 of pin 3203. The access point along spherical trajectory 3315 may be substantially a first distance from end 3205. The distance may substantially correspond to a magnitude of radius r11. Spherical trajectory 3313 of extension 3303 may be a second distance from end 3205. The second distance may substantially correspond to a magnitude of radius r12.

The magnitude of radius r11 may substantially correspond to the magnitude of radius r12. Trajectory 3313 may be orthogonal to trajectory 3315. Radius r11 may be orthogonal to radius r12. The first distance may equal the second distance.

End 3205 may be a center of spherical trajectory 3313. End 3205 may be a center of spherical trajectory 3315 (shown in FIG. 33). End 3205 may correspond to a target site interior to bone B. Indicator 3305 may be associated with a known distance (r11) from the target site. Indicator 3305 may identify an access point on bone B a known distance from the target site. Indicator 3305 may identify the access point on bone B at a known distance from the target site independent of anatomical discrepancies associated with bone B. Indicator 3305 may consistently identify an access point on bone B a known distance from the target site.

Figure 35:
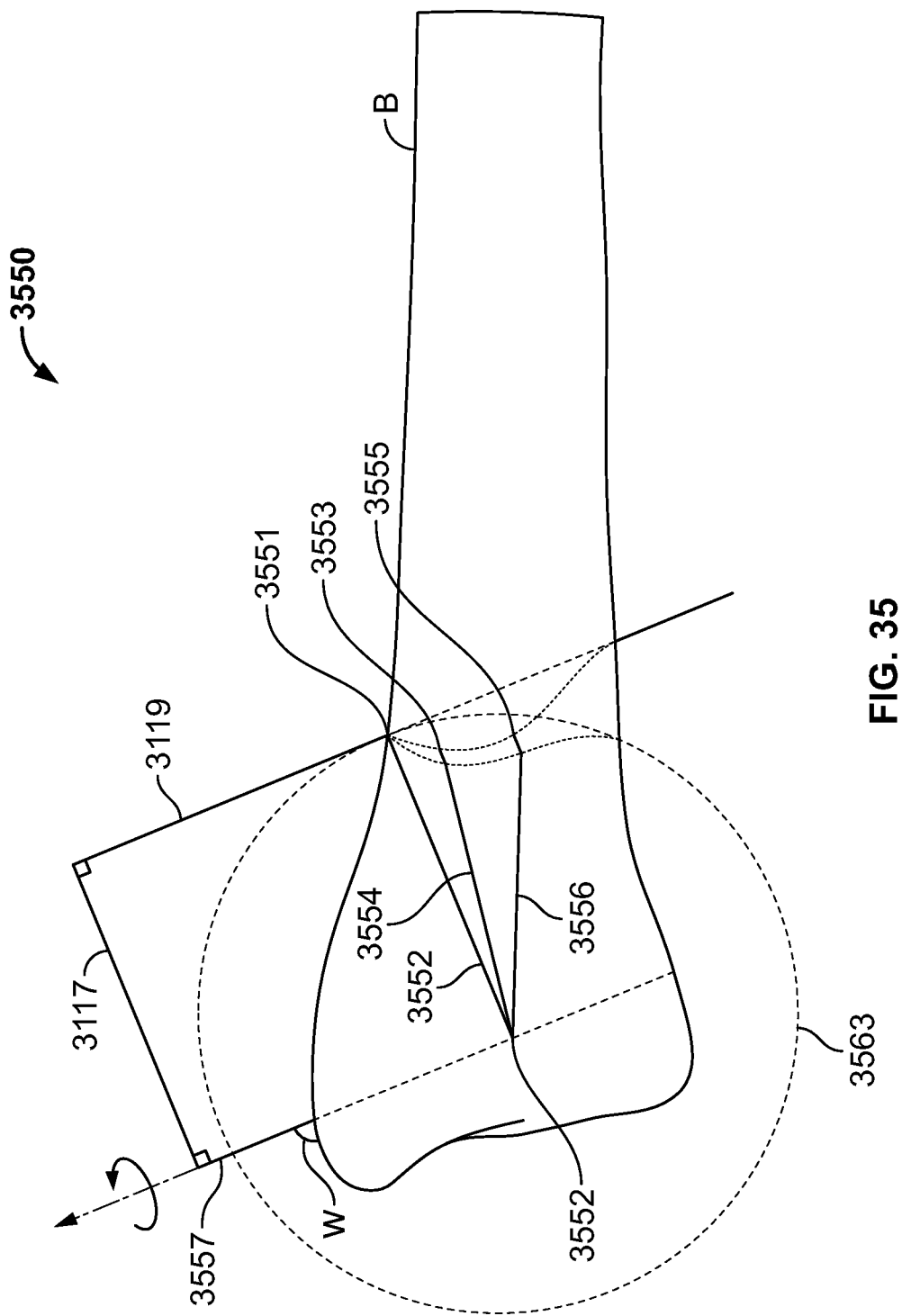
FIG. 35 shows information in accordance with the principles of the invention.

FIG. 35 shows illustrative schematic model 3550. Model 3550 illustrates principles that may be embodied in apparatus such as 3400 (shown in FIG. 34). Model 3550 shows point 3552. Point 3552 may be interior to a bone B. Point 3552 may correspond to a location for an end of a bone implant such as implant 300 (shown in FIG. 3B). The bone implant may have a length commensurate with line 3117.

Point 3552 may lie on line 3557. Line 3557 may correspond to a pin, such as pin 2701 (shown in FIG. 27), fixed at angle W relative to bone B. Point 3552 may be a center of spherical surface 3563 (shown in cross-section).

Each of lines 3552, 3554 and 3556 are radii of spherical surface 3563 and have corresponding endpoints 3551, 3553 and 3555 on a convex portion of the surface of bone B. Each of endpoints 3551, 3553 and 3555 is thus spaced apart a distance 3117 from point 3553 and is a suitable candidate for placing an access hole for the deployment of an implant having length 3117.

Figure 36:
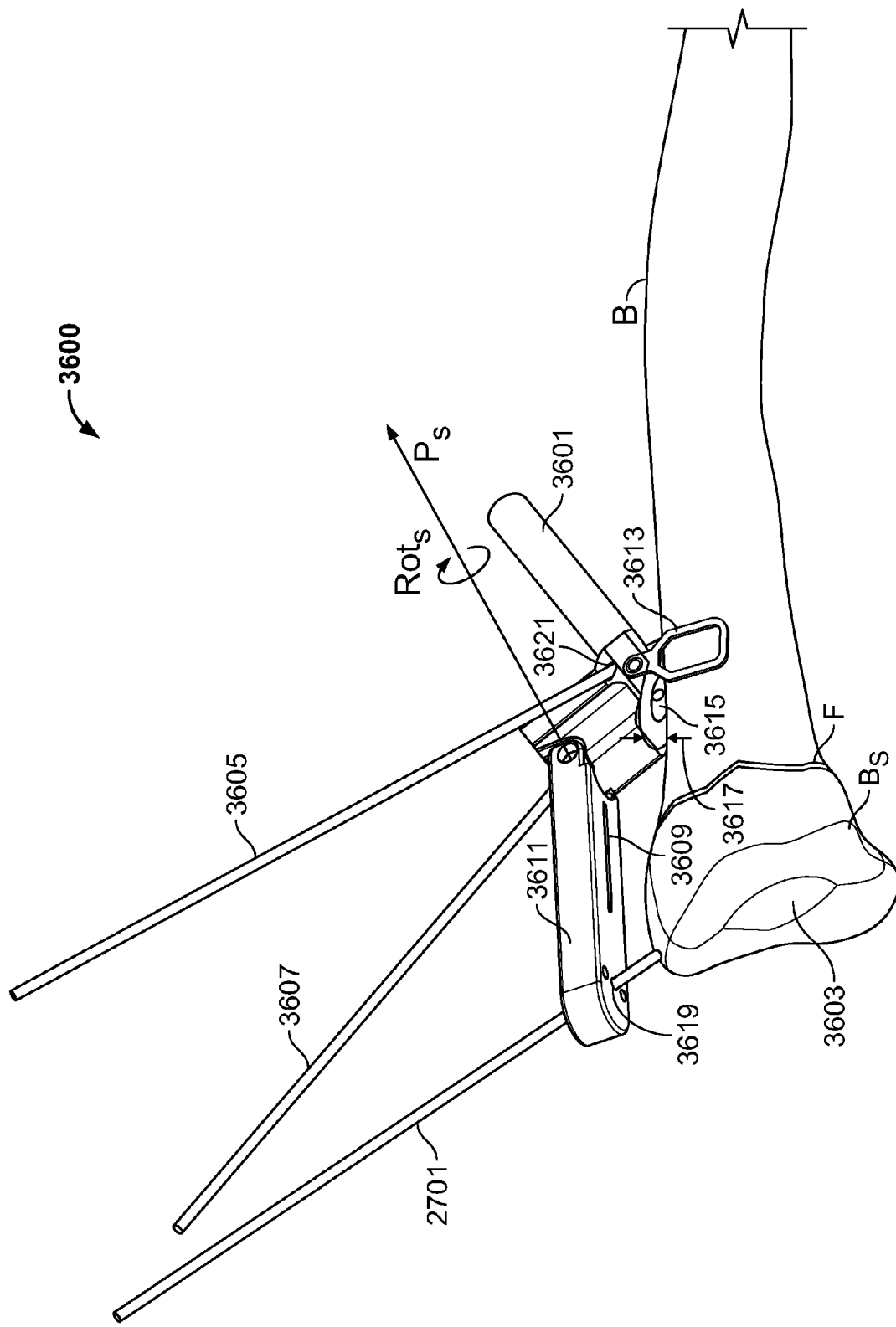
FIG. 36 shows yet other apparatus in accordance with the principles of the invention along with a portion of the anatomy shown in FIG. 8.

FIG. 36 shows illustrative apparatus 3600. Apparatus 3600 may include support 3611. Support 3611 may include receptacle 3619. Receptacle 3619 may guide pin 2701 into bone segment Bs. Support 3611 may include marker 3609. Marker 3609 may be visible under fluoroscopic imaging. Marker 3609 may position support 3611 relative to bone B.

Marker 3609 may position support 3611 along a center-line Lb of bone B (shown in FIG. 3A). Marker 3609 may be aligned based on a target site for an implant inserted into bone B.

Support 3611 may be positioned, such that pin 2701, when inserted through receptacle 3619 follows a subchondral surface 3603 of bone B. Support 3611 may pivot about axis Ps. Support 3611 may pivot about axis Ps to reduce a displacement indicated by arrows 3617. Displacement 3617 may correspond to a distance of guide 3601 from bone B.

Apparatus 3600 may include guide 3601. Guide 3601 may be positioned on bone B. Alignment member 3613 may align guide 3601 on bone B. Guide 3601 may include guide surface 3615. Guide surface 3615 may be positioned to direct a surgical tool, such as drill 2901 (shown in FIG. 29) to an access point on bone B. Guide 3601 may be positioned on a lateral side of bone B. Guide 3601 may be positioned on a medial side of bone B.

Apparatus 3600 may include bone penetrating members 3607 and 3605. Bone penetrating members 3607 and 3605 may be inserted into cortical bone BCO (shown in FIG. 3A) of bone B. Bone penetrating member 3605 may be inserted into bone B through receptacle 3621. Receptacle 3621 may be configured to direct bone penetrating member 3605 into bone B in a "toe-nail" position. Bone penetrating member 3607 may be inserted into radius R through a receptacle (not shown). Bone penetrating members 3607 and 3605 may stabilize guide 3601 on bone B.

Figure 37:
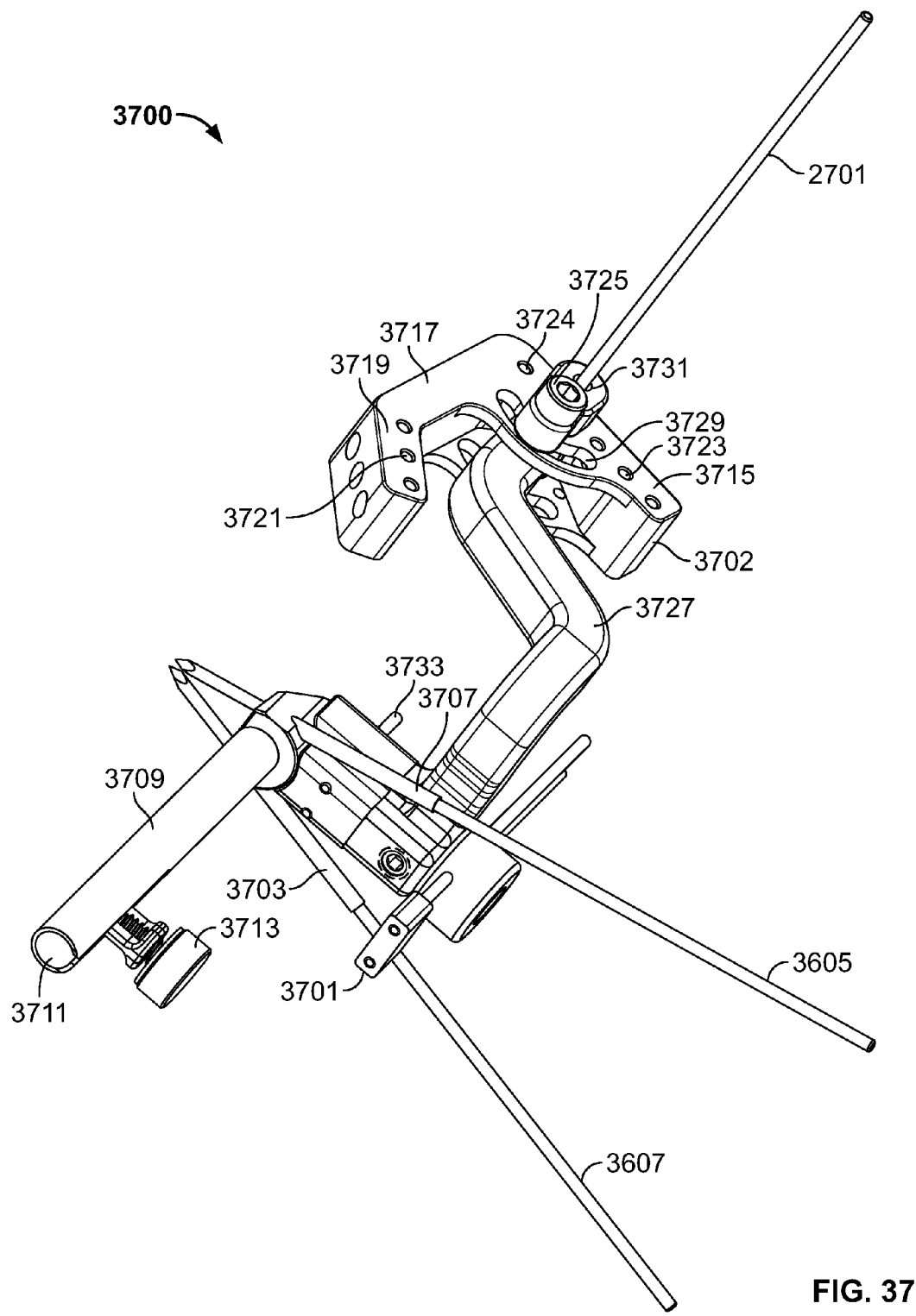
FIG. 37 shows yet other apparatus in accordance with the principles of the invention.

FIG. 37 shows illustrative apparatus 3700. Apparatus 3700 may include jig 3702. Jig 3702 may include one or more of the features of jig 1000 (shown in FIG. 10).

Apparatus 3700 may include bridging member 3715. Bridging member 3715 may include receptacles 3723 and 3724. Receptacle 3723 may be configured to receive a first bone penetrating member such as bone penetrating member 1007 (shown in FIG. 10). The first bone penetrating member may be secured to a first bone segment such as bone segments Pa or Ph (shown in FIG. 3A).

Receptacle 3724 may be configured to receive a second bone penetrating member such as bone penetrating member 1001 (shown in FIG. 10). The second bone penetrating member may be secured to a second bone segment such as bone segments Pa or Ph (shown in FIG. 3A). The first and second bone penetrating members may position the first bone segment relative to the second bone segment. The first and second bone penetrating members may be secured to a dorsal side (shown in FIG. 3A) of bone B.

Apparatus 3700 may include support 3717. Support 3717 may be joined to base 3719. Base 3719 may include receptacle 3721. Receptacle 3721 may be configured to receive a third bone penetrating member secured to a reference bone segment. The third bone penetrating member may position the first and the second bone segments relative to the reference bone segment.

Bridging member 3715 may fix a position of the first bone segment relative to the second bone segment. Bridging member 3715 and base 3719 may fix a position of the first and second bone segments relative to the reference bone segment. Apparatus 3700 may reduce fractures Fa and Fh (shown in FIG. 3A).

Receptacle 3731 may be configured to receive pin 2701. Support 3727 may articulate against pin 2701. A position of support 3727 relative to channel 3729 may be fixed by set screw 3725.

Apparatus 3700 may include guide 3709. Guide 3709 may be in mechanical coordination with support 3727. Support 3727 may position guide 3709 on a lateral side of bone B. Support 3727 may position guide 3709 relative to a site interior to a fractured bone. Guide 3709 may include guide surface 3711. Guide surface 3711 may align a surgical tool with the site.

Apparatus 3700 may include guide surface extender 3713. Guide surface extender 3713 may position a guide surface extension (not shown) relative to the reference bone segment. Rotation of guide surface extender 3713 may fix a position of the guide surface extension relative to the reference bone segment.

Apparatus 3700 may include channels 3703 and 3707. Bone penetrating members 3705 and 3707 may be inserted through channels 3707 and 3703, respectively, through cortical bone BCO (shown in FIG. 3A). Bone penetrating members 3705 and 3707 may stabilize guide 3709 on bone B. Bone penetrating members 3705 and 3707 may be K-wires. Bone penetrating members 3705 and 3707 may be inserted into bone B using a wire drill.

Apparatus 3700 may include alignment members 3733 and 3701. Alignment members 3733 and 3701 align guide 3709 along the reference bone. Alignment members 3733 and 3701 may align guide 3709 along a center-line LB of bone B (shown in FIG. 3A).

Figure 38:
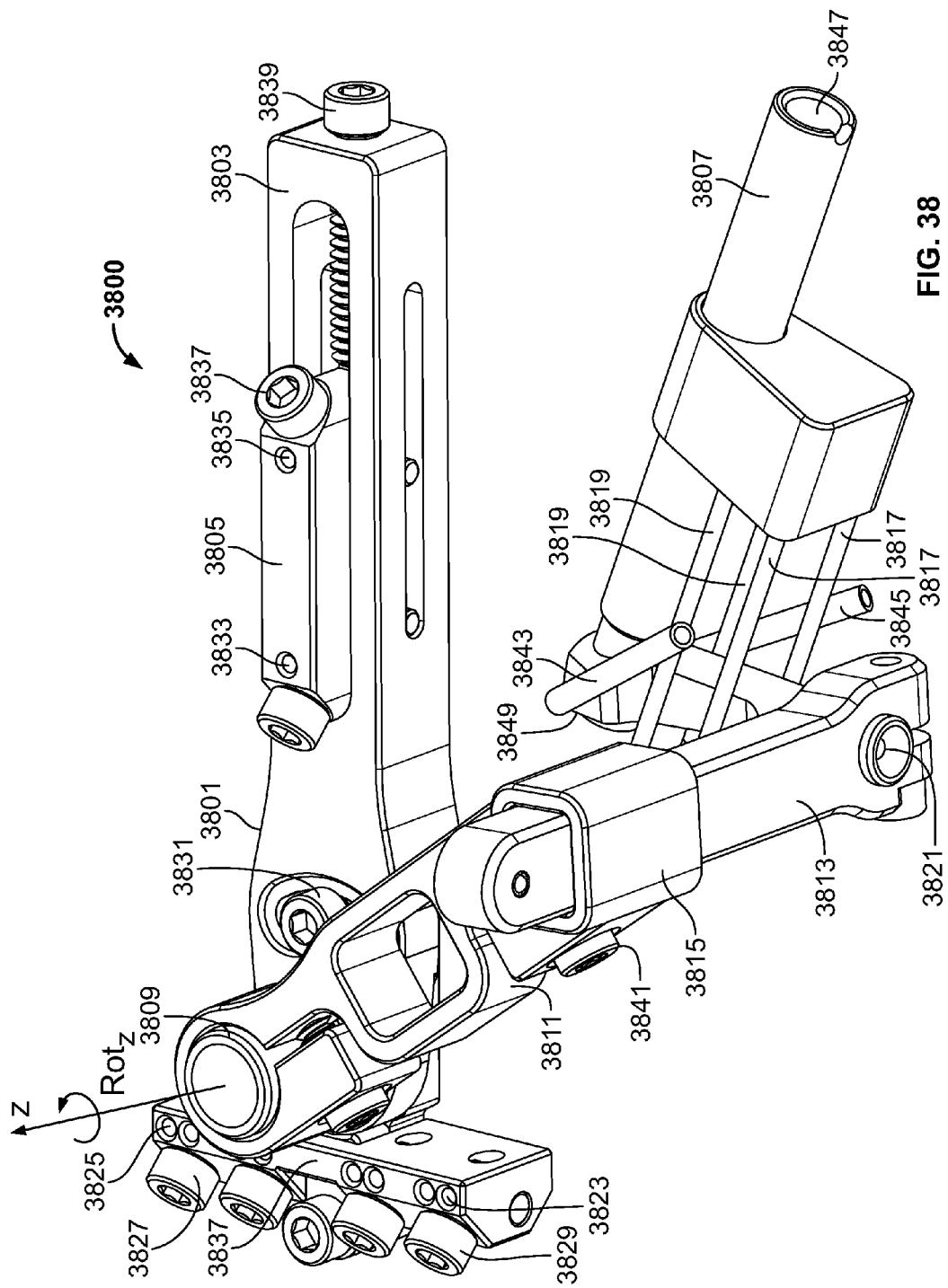
FIG. 38 shows yet other apparatus in accordance with the principles of the invention.

FIG. 38 shows illustrative apparatus 3800. Apparatus 3800 may include jig 3801. Jig 3801 may include one or more of the features of jig 1000 (shown in FIG. 10).

Apparatus 3800 may include bridging member 3837. Bridging member 3837 may include receptacles 3823 and 3825. Receptacles 3823 and 3825 may be configured to receive bone penetrating elements such as bone penetrating members 1312 and 1314 (shown in FIG. 13). Bone penetrating members 1312 and 1314 may each be secured to a bone segments such as Ph or Pa (shown in FIG. 3A). Set screws 3827 and 3829 may fix a position of bone penetrating elements 1312 and 1314 relative to bridging member 3837.

Bridging member 3837 may be configured to pivot about axis Z. Axis Z may be positioned relative to a site interior to bone B. Apparatus 3800 may include a marker (not shown) positioned about axis Z. The marker may include one or more of the features of marker 3609 (shown in FIG. 36). The marker may aid positioning of apparatus 3800 relative to the site interior to bone B. Rotation of bridging member 3837 about axis Z may position the bone segments secured to bone penetrating members 1312 and 1314. A position of bridging member 3837 about axis Z may be fixed by set screw 3831.

Apparatus 3800 may include base 3803. Apparatus 3800 may include collar 3805. Collar 3805 may include receptacles 3833 and 3835. Bone penetrating members such as 1311 and 2601 (shown in FIG. 26) may be received by receptacles 3833 and 3835. Bone penetrating members such as 1311 and 2601 may secure base 3803 to a reference bone segment such as bone segment Pb (shown in FIG. 3A). Set screw 3839 may position collar 3805 relative to base 3803.

Apparatus 3800 may be configured to position bone segment Pa relative to bone segment Ph. Apparatus 3800 may be configured to position bone segments Pa and Ph relative to bone segment Pb. Apparatus 3800 may be configured to lock a relative position of bone segments Pb, Pa and Ph.

Apparatus 3800 may include support 3811. Support 3811 may pivot about axis Z. Support 3811 may include extension 3813. Extension 3813 may translate relative to band 3815. Set screw 3841 may fix a position of extension 3813 relative to band 3815. Support 3811 and extension 3813 may be configured to position guide 3807 relative to bone B. Alignment members 3817 and 3819 may position guide 3807 relative to a center-line Lb (shown in FIG. 3A) of bone B. Guide end 3849 may indicate an access point on bone B. Guide surface 3847 may be oriented to align a surgical tool at the indicated access point.

Guide 3807 may include channels 3843 and 3845. Bone penetrating members 3805 and 3807 may be inserted through channels 3707 and 3703 into cortical bone BCO (shown in FIG. 3A) to stabilize guide 3807 on bone B. Extension 3813 may include receptacle 3821. A bone penetrating member may be inserted through receptacle 3821 into cortical bone BCO (shown in FIG. 3A) to stabilize apparatus 3800 on bone B. A bone penetrating member may be inserted through receptacle 3821 into cortical bone BCO to create a pilot hole in bone B.

Figure 39:
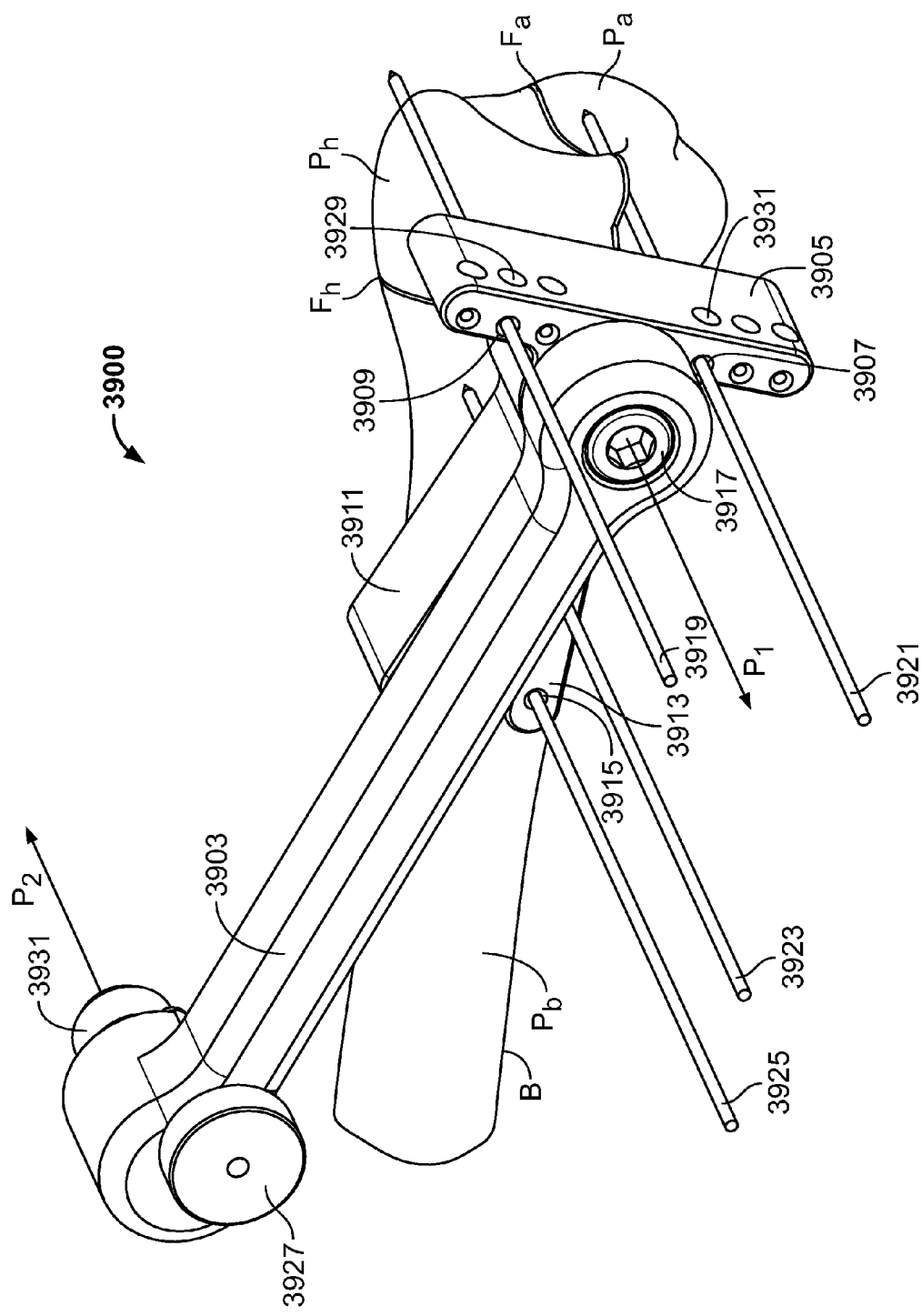
FIG. 39 shows yet other apparatus in accordance with the principles of the invention, along with anatomy.

FIG. 39 shows illustrative apparatus 3900. Apparatus 3900 may have one or more features in common with jig 1000 (shown in FIG. 10) or jig 1300 (shown in FIG. 13).

Apparatus 3900 may include bridging member 3905. Bridging member 3905 may include receptacles 3907 and 3909. Receptacles 3907 may be configured to receive bone penetrating members 3921 and 3919, respectively. Bone penetrating member 3921 may be secured to bone segment Pa. A position of bone penetrating member 3921 may be fixed relative to bridging member 3905 using a set screw (not shown) inserted into receptacle 3931.

Bone penetrating member 3919 may be secured to bone segment Ph. A position of bone penetrating member 3919 may be fixed relative to bridging member 3905 using a set screw (not shown) inserted into receptacle 3929. Apparatus 3900 may be configured to position bone segment Ph relative to bone segment Pa.

Apparatus 3900 may include base extensions 3911 and 3913. Base extension 3913 may include receptacle 3915. Receptacle 3915 may be configured to receive bone penetrating member 3925. Base extension 3913 may include a receptacle (not shown) configured to receive bone penetrating member 3923. Bone penetrating members 3925 and 3923 may be secured to bone segment Pb. Bone penetrating members 3925 and 3923 may be fixed relative to base extension 3913 by one or more set screws (not shown). Base extension 3911 may have one or more features in common with base extension 3913.

Apparatus 3900 may be configured to position bone segment Pa relative to a center of bone segment Pa. Apparatus 3900 may be configured to position bone segment Ph relative to a center of bone segment Ph. Apparatus 3900 may be configured to fix a position of bone segments Ph and Pa relative to bone segment Pb. Apparatus 3900 may be configured to reduce fractures Fh and Fa.

Apparatus 3900 may include guide support 3903. Guide support 3903 may be configured to rotate about axis P1. A position of guide support 3903 about axis P1 may be fixed by tightening set screw 3917. Guide support 3903 may be positioned about axis P1 relative to bone segment Pb. Guide support 3903 may include knobbed detent 3927. Guide support 3903 may include articulating surface 3931. Guide support 3903 may be affixed to a dorsal side of bone B.

Figure 40:
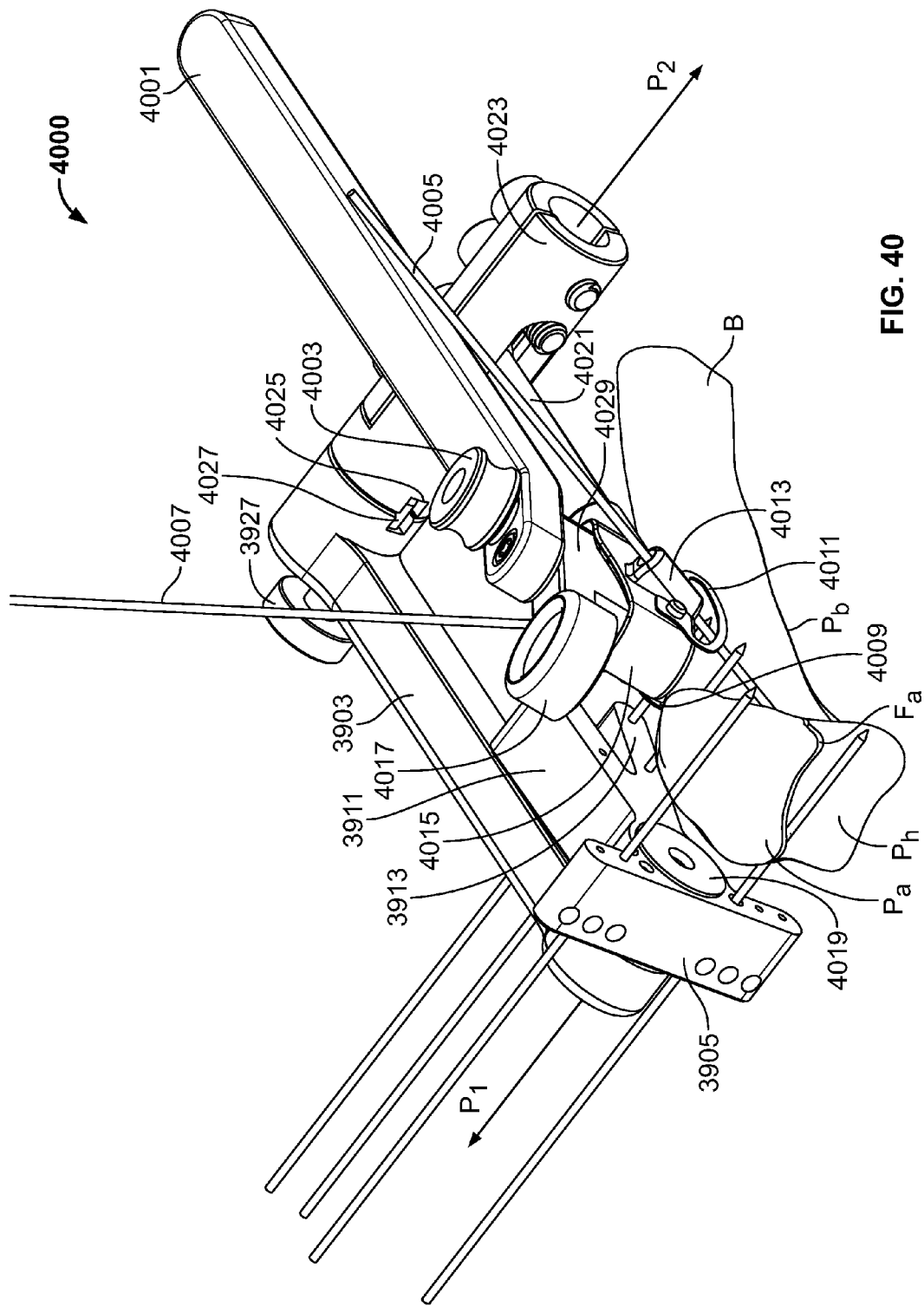
FIG. 40 shows the apparatus and anatomy of FIG. 39, along with other apparatus in accordance with the principles of the invention.

FIG. 40 shows illustrative apparatus 4000. Apparatus 4000 may have one or more features in common with the apparatus 3900. Apparatus 4000 may be positioned relative to a site interior to bone B. Marker 4019 may be visible under fluoroscopic imaging. Marker 4019 may be positioned relative to the site interior to bone B.

Apparatus 4000 may include guide extension 4023. Guide extensions 3903 and 4023 may be configured to position guide 4021 relative to bone B. Guide extension 3903 may pivot about axis P1. Articulating surface 3931 (shown in FIG. 39) may be positioned at a distance from bone B. A position of articulating surface 3931 may be fixed using set screw 3917 (shown in FIG. 39).

Guide extension 3903 may be configured to articulate against articulating surface 3931. Guide extension 4023 may pivot about axis P2. Guide extension 4023 may be configured to align guide 4021 and guide collar 4015 with bone B.

Guide 4021 and guide collar 4015 may be detached from guide support 3903. Guide 4021 and guide collar 4015 may be detached from guide support 3903 during reduction of fractures Fa and Fh (shown in FIG. 39). Detachment of guide 4021 and guide collar 4015 from bone B may provide a substantially unobstructed view of bone B during the reduction procedure.

Guide extension 4023 may include enclosure 4025. Guide extension 4023 may be fixed at a position about axis P2 by knobbed detent 3927. Knobbed detent 3927 may be maintained in a default position by a spring (not shown). Knobbed detent 3927 may include tip 4027. Tip 4027 may be configured to extend into enclosure 4025. Translating knobbed detent along axis P2 may release guide 4021 and guide collar 4015 from guide support 3903. Translating knobbed detent along axis P2 may release tip 4027 from enclosure 4025.

Guide collar 4015 may be configured to position guide 4021 on bone B. Guide collar 4015 may include alignment members 4009 and 4011. Alignment members 4009 and 4011 may position guide 4021 along a center-line LB (shown in FIG. 3A) of bone B. Receptacle 4013 may be configured to receive bone penetrating member 4005. A receptacle (not shown) may be configured to receive bone penetrating member 4007. The receptacle may have one or more features in common with receptacle 4013. Bone penetrating members 4005 and 4007 may be secured to bone B. Bone penetrating members 4005 and 4007 may be secured to bone B in a "toe-nail" configuration. Bone penetrating members 4005 and 4007 may fix a position of guide collar 4015 relative to bone B.

Insert 4029 may be configured to be position inside guide collar 4015. Insert 4029 may include indicator 4017. Indicator 4017 may indicate a site interior to bone B. The site may correspond to a target site of an implant configured to maintain a reduction of fractures Fa and Fh. Insert 4017 may be positioned or removed from guide collar 4015 using handle 4001. Inserted 4017 may be removed from guide collar 4015 after guide collar 4015 is secured to bone B.

Handle 4001 may include bushing 4003. Bushing 4003 may be configured to receive a bone penetrating member. The bone penetrating member may be secured to bone B. Bushing 4003 may be configured to indicate an access point (shown in FIG. 29). The access point may correspond to the site interior to bone B. Bushing 4003 may position a surgical tool such as drill 2901 (shown in FIG. 29) at the access point.

Figure 41:
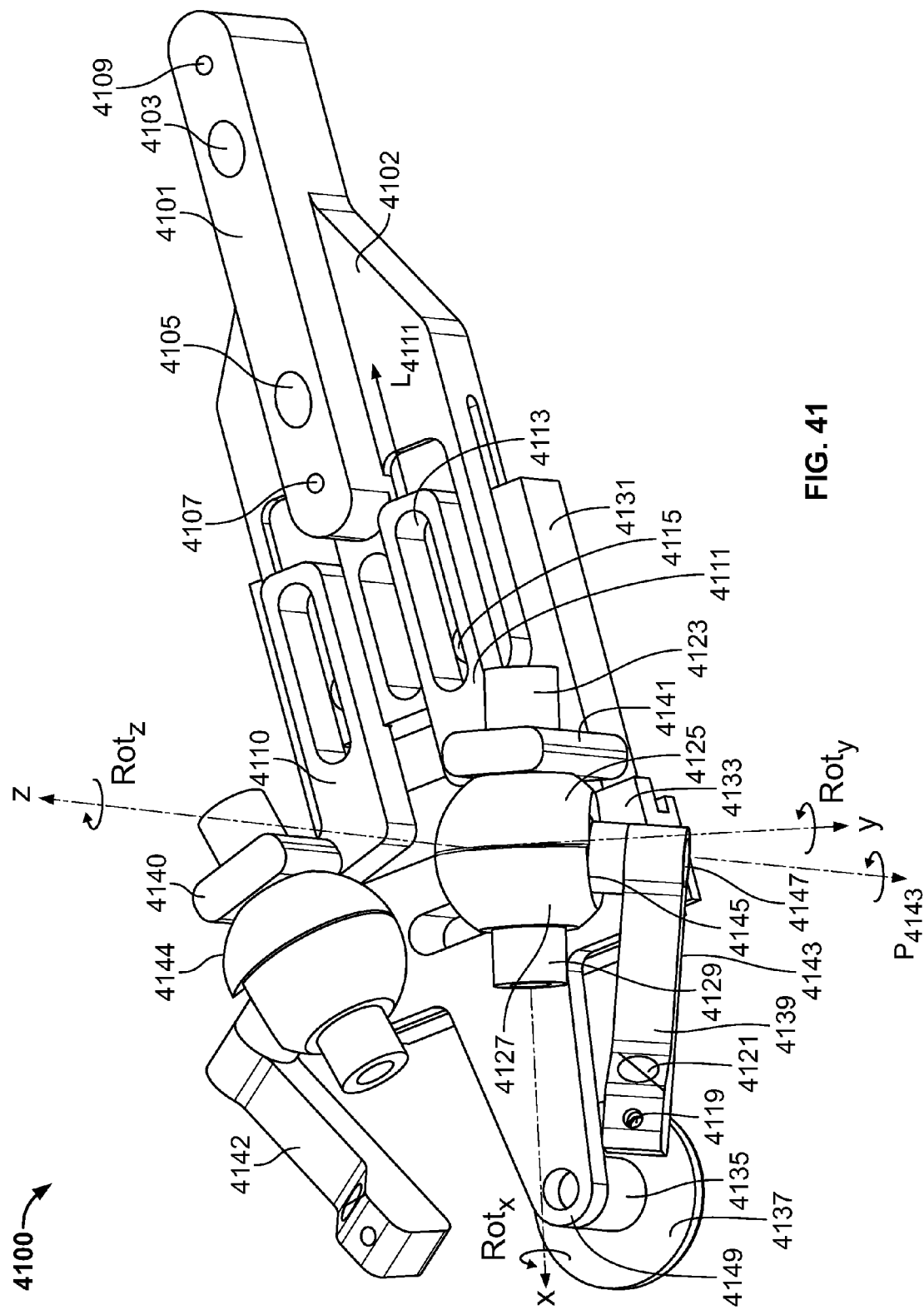
FIG. 41 shows yet other apparatus in accordance with the principles of the invention.

FIG. 41 shows illustrative apparatus 4100. Apparatus 4100 may include collar 4143. Collar 4143 may include offset member 4139. Offset member 4139 may include receptacle 4119. Receptacle 4119 may be configured to receive bone a penetrating member. The bone penetrating member may be secured to a bone segment, such as bone segment Pa or bone segment Ph (shown in FIG. 3A).

A position of the bone penetrating member may be fixed relative to offset member 4139. Offset member 4139 may include receptacle 4121. Receptacle 4121 may be configured to receive a set screw (not shown). The set screw may fix a position of the bone penetrating member relative to offset member 4139.

Collar 4143 may be configured to displace the bone segment secured to the bone penetrating member. Collar 4143 may be configured to displace the bone segment relative to a center of the bone segment. The center of the bone segment may correspond to origin O1 or O2 (shown in FIG. 7). Collar 4143 may be configured to displace the bone segment along three orthogonal axes. Collar 4143 may be configured to rotate the bone segment about three orthogonal axes.

Collar 4143 may be configured to rotate about axis P4143. Collar 4143 may be configured to rotate the bone segment about axis 4143. Offset member 4139 may include receptacle 4147. Receptacle 4147 may be configured to receive a set screw (not shown). The set screw may fix a position of offset member 4139 about axis P4143.

Collar 4143 may be configured to displace the bone segment along axes X, Y and Z. Collar 4143 may be configured to rotate the bone segment about axes X, Y and Z.

Apparatus 4100 may include collar support 4145. Collar support 4145 may include hemisphere 4125 and hemisphere 4127. Hemisphere 4125 may include receptacle 4123. Hemisphere 4127 may include female threaded member 4129. Receptacle 4123 may be configured to receive a set screw (not shown). The set screw may include outer threads configured to engage female threaded member 4129. Engagement of the set screw and female threaded member 4129 may fix a position of collar 4143 along axes X, Y and Z. Engagement of the set screw and female threaded member 4129 may fix a position of collar 4143 about axes X, Y and Z.

Apparatus 4100 may include central member 4101. Central member 4101 may include receptacles 4107 and 4109. Receptacles 4107 and 4109 may each be configured to receive a bone penetrating member. The bone penetrating member may be secured to a bone segment such as bone segment Pb (shown in FIG. 3A). Central member 4101 may be configured to secure apparatus 4100 to a reference bone segment. Central member 4101 may be positioned relative to a bone segment.

Central member 4101 may include receptacles 4105 and 4103. Receptacles 4105 and 4103 may each be configured to receive a set screw (not shown). The set screw may fix a position of the bone penetrating member received by receptacle 4107 or 4109. The set screw may fix a position of central member 4101 relative to the bone penetrating member. The set screw may fix a position of central member 4101 relative to the bone segment secured to the bone penetrating member.

Apparatus 4100 may include rail 4102 and base 4111. Rail 4102 may be rigidly secured to central member 4101. Rail 4102 may include receptacle 4115. Receptacle 4115 may be configured to receive a set screw (not shown). The set screw may secure base 4111 to rail 4102. Base 4111 may be configured to translate relative to rail 4102 along axis L4111. The set screw may fix a position of base 4111 relative to rail 4102.

Base 4111 may include bracket 4141. Bracket 4141 may be rigidly secured to base 4111. Bracket 4141 may include a receptacle (not shown). The receptacle may be configured to receive hemisphere 4125. Bracket 4141 may be secured to hemisphere 4125.

Apparatus 4100 may be configured to position bone segment Pa relative to bone segment Ph. Apparatus 4100 may be configured to fix a position bone segment Pa relative to bone segment Ph.

Apparatus 4100 may be configured to manipulate two or more bone segments relative to a reference bone segment. Apparatus 4100 may include collar 4142, collar support 4144, bracket 4140 and base 4110. Collar 4138 may have one or more features in common with collar 4143. Collar support 4144 may have one or more features in common with collar support 4145. Bracket 4140 may have one or more features in common with bracket 4141. Base 4110 may have one or more features in common with base 4111.

Apparatus 4100 may be configured to position bone segment Pa and bone segment Ph relative to bone segment Pb (shown in FIG. 3A). Apparatus 4100 may be configured to reduce fractures Fa or Fh (shown in FIG. 3A).

Apparatus 4100 may include slider 4131. Slider 4131 may be configured to translate relative to rail 4102. Apparatus 4100 may include targeting member 4133. Targeting member 4133 may be configured to translate relative to slider 4131. Targeting member 4133 may include nose 4149. Nose 4149 may include marker 4137. Marker 4137 may position apparatus 4100 relative to a sit interior to bone B. Maker 4137 may be visible during fluoroscopic imaging.

Figure 42:
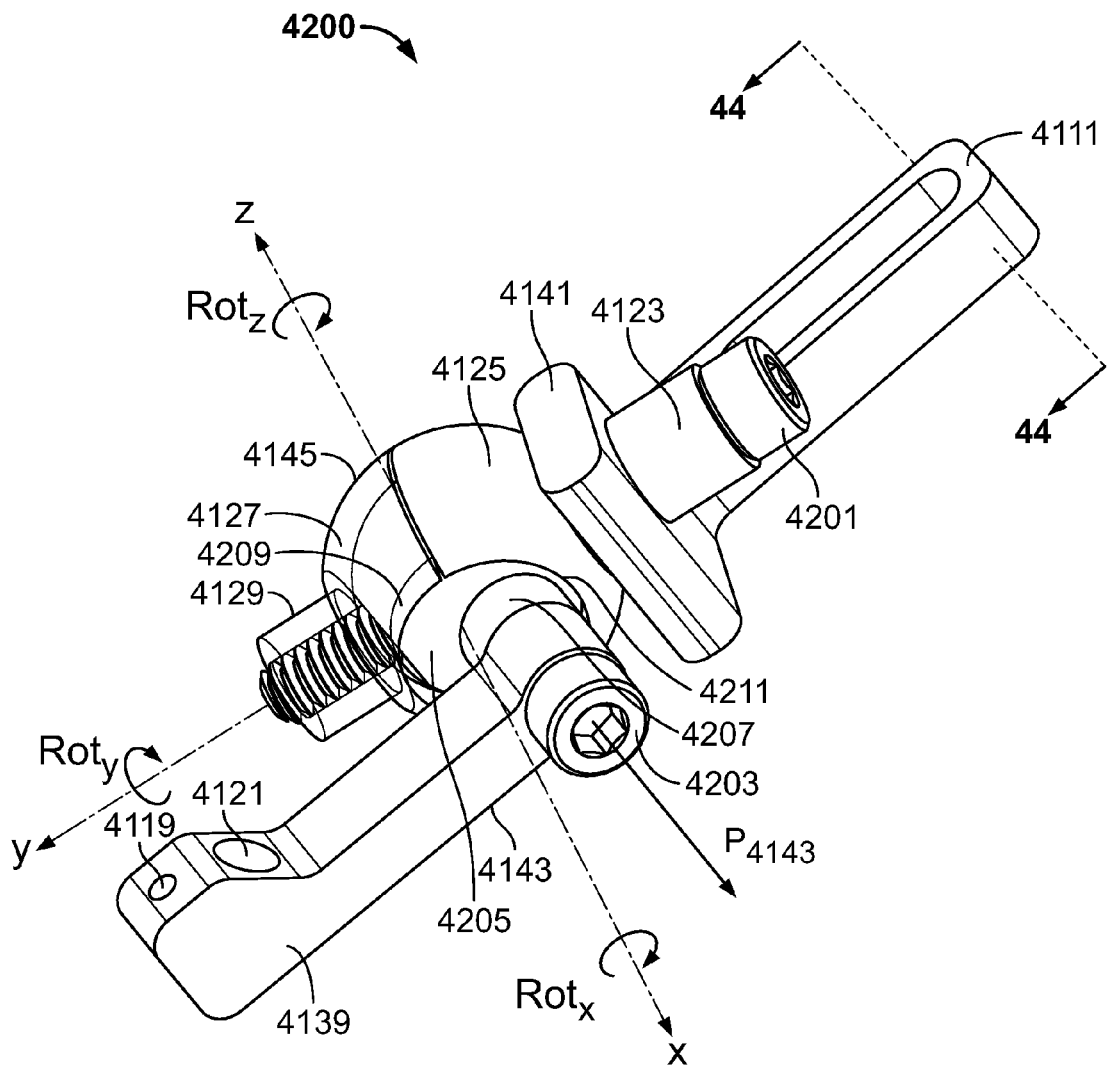
FIG. 42 shows a portion of the apparatus shown in FIG. 41.

FIG. 42 shows illustrative components 4200. Components 4200 may include collar 4143. Collar 4143 may include articulating surface 4205. Articulating surface 4205 may include a spherical curvature. Articulating surface 4205 may be configured to translate along axes X, Y or Z. Articulating surface 4205 may be configured to rotate about axes X, Y or Z.

Components 4200 may include collar support 4145. Collar support 4145 may include hemisphere 4145 and hemisphere 4127. Articulating surface 4205 may be configured to articulate against hemisphere 4125. Articulating surface 4205 may be configured to articulate against hemisphere 4127.

Hemisphere 4127 may include female threaded member 4129. Set screw 4201 may be configured to threadedly engage female threaded member 4129. Hemisphere 4125 may include receptacle 4123. Receptacle 4123 may be configured to receive set screw 4201. Threaded engagement of set screw 4201 and female threaded member 4129 may compress hemisphere 4125 and hemisphere 4127 against articulating surface 4205.

Compression of hemisphere 4125 and hemisphere 4127 against articulating surface 4205 may fix a position of collar 4143 along axes X, Y and Z. Compression of hemisphere 4125 and hemisphere 4127 against articulating surface 4205 may fix a position of collar 4143 about axes X, Y and Z. Compression of hemisphere 4125 and hemisphere 4127 against articulating surface 4205 may fix a position of a bone segment secured to collar 4143. The position of the bone segment may be fixed relative to center of the bone segment. The center may correspond to origin O1 or O2 (shown in FIG. 7). The position of the bone segment may be fixed relative to a reference bone segment.

Hemisphere 4125 may include edge 4211. Hemisphere 4209 may include edge 4209. Collar 4143 may include female threaded member 4207. Female threaded member 4207 may be configured to articulate against a portion of edge 4211. Female threaded member 4207 may be configured to articulate against a portion of edge 4209.

Female threaded member 4207 may be configured to threadedly engage set screw 4203. Threaded engagement of set screw 4203 and female threaded member 4207 may fix a position of offset arm 4139 about axis P4143. Threaded engagement of set screw 4203 and female threaded member 4207 may fix a position of a bone segment secured to collar 4143. The position of the bone segment may be fixed relative to axis P4143. The position of the bone segment may be fixed relative to a center of the bone segment. The center of the bone segment may correspond to origin O1 or O2.

Figure 43:
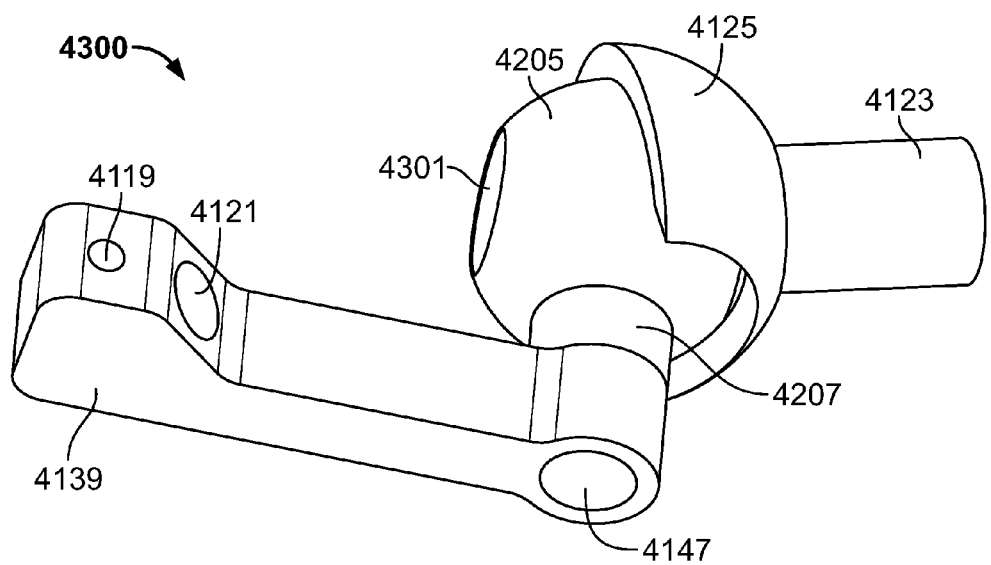
FIG. 43 shows a portion of the apparatus shown in FIG. 42.

FIG. 43 shows illustrative components 4300. Components 4300 may include articulating surface 4205. Articulating surface 4205 may include receptacle 4301. Receptacle 4301 may be configured to receive set screw 4201 (shown in FIG. 42).

Figure 44:
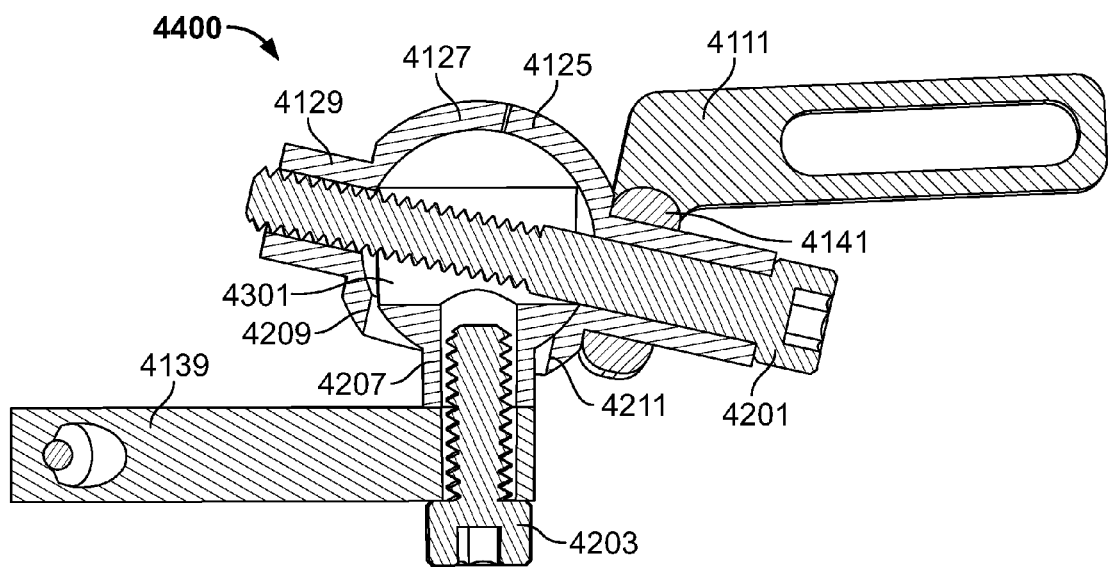
FIG. 44 shows a cross-sectional view, taken along lines 44-44 (shown in FIG. 42) of the apparatus shown in FIG. 42.

FIG. 44 shows cross-section 4400 along lines 44-44 (shown in FIG. 42). Cross-section 4200 shows set screw 4201 (shown in FIG. 42) passing through receptacle 4301 (shown in FIG. 43). Cross-section 4200 shows set screw 4201 threadedly engaged with female threaded member 4129 (shown in FIG. 41).

Cross-section 4400 shows set screw 4203 passing through receptacle 4147 (shown in FIG. 41). Cross-section 4400 shows set screw 4203 threadedly engaged with female threaded member 4207.

Figure 45:
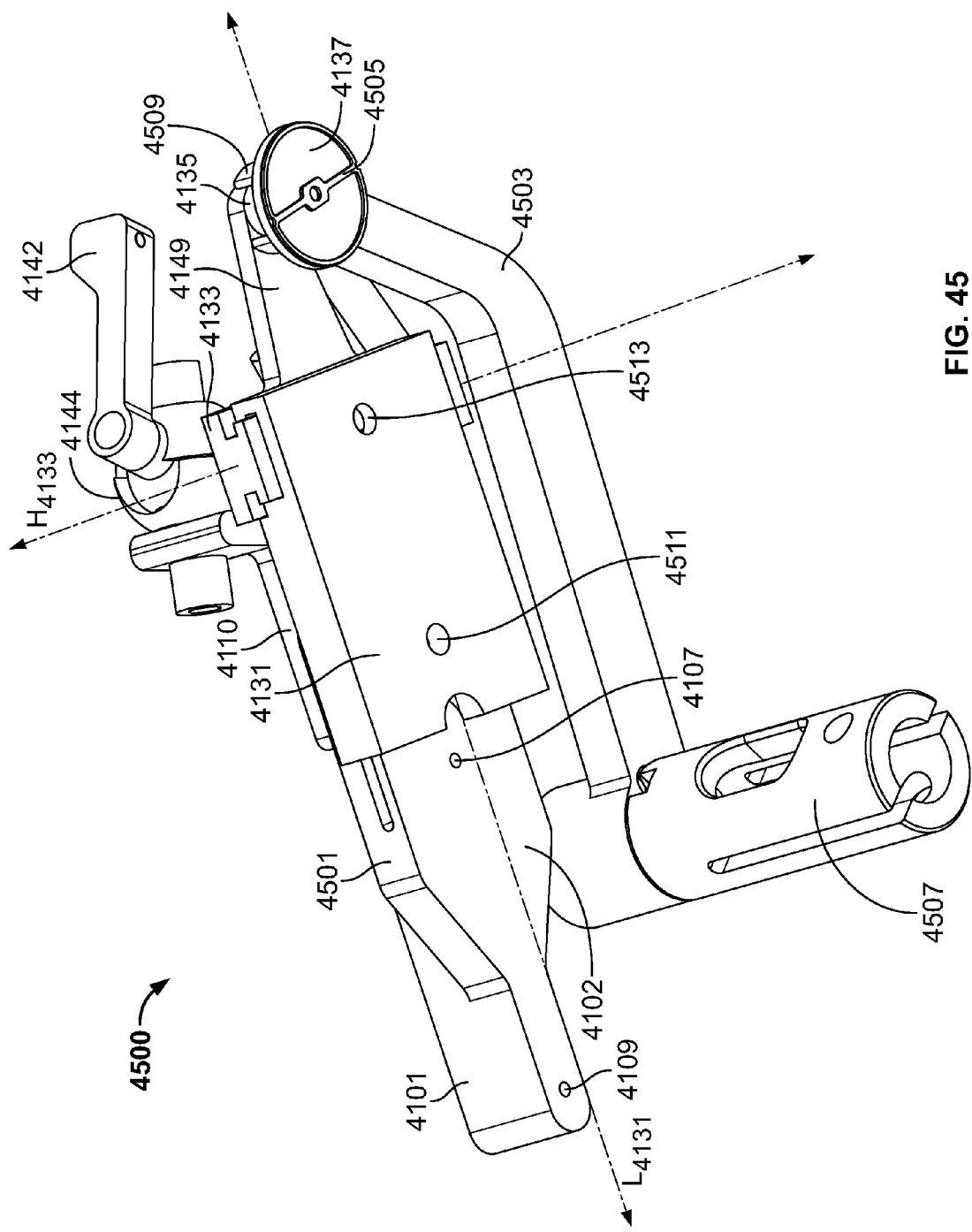
FIG. 45 shows the apparatus shown in FIG. 42 along with other apparatus in accordance with the principles of the invention.

FIG. 45 shows illustrative apparatus 4500. Apparatus may have one or more features in common with apparatus 4100. Apparatus 4500 may include slider 4131 (shown in FIG. 41). Slider 4131 may be configured to translate along axis L4131. Slider 4131 may be configured to translate relative to rails 4501 and 4102.

Apparatus 4500 may include central member 4101. Central member 4101 may be secured to a bone segment. Slider 4131 may be configured to translate relative to the bone segment.

Apparatus 4500 may include targeting member 4133. Targeting member 4133 may include nose 4149 and marker 4137. Marker 4137 may include template 4505. Template 4505 may be visible during fluoroscopic imaging. Targeting member 4133 may be configured to translate along axis H4149.

Translation of slider 4131 may position marker along axis L4131. Translation along axis L4131 may position marker 4137 relative to a site interior to bone B. Translation of targeting member 4133 may position marker 4137 along axis H4133. Translation along axis H4133 may position marker 4137 relative to a site interior to bone B.

Slider 4131 may include receptacle 4511. Threaded engagement of a set screw (not shown) and receptacle 4511 may fix a position of slider 4131 relative to rails 4501 and 4102. Targeting member 4133 may include receptacle 4513. Threaded engagement of a set screw (not shown) and receptacle 4513 may fix a position of targeting member 4133 relative to slider 4131.

Apparatus 4500 may include support 4503. Support 4503 may include clasp 4509. Clasp 4509 may be configured to articulate against cylindrical surface 4135. Support 4503 may be configured to articulate relative to targeting member 4133.

Support 4503 may include indicator 4507. Indicator 4507 may be configured to identify an access point on bone B. Support 4503 may be configured to identify the access point at an intersection of indicator 4507 and soft tissue adjacent bone B. Indicator 4507 may be configured to cooperate with a guide (not shown). The access point may correspond to a site interior to bone B. The access point may correspond to the site identified by marker 4137.

Figure 46:
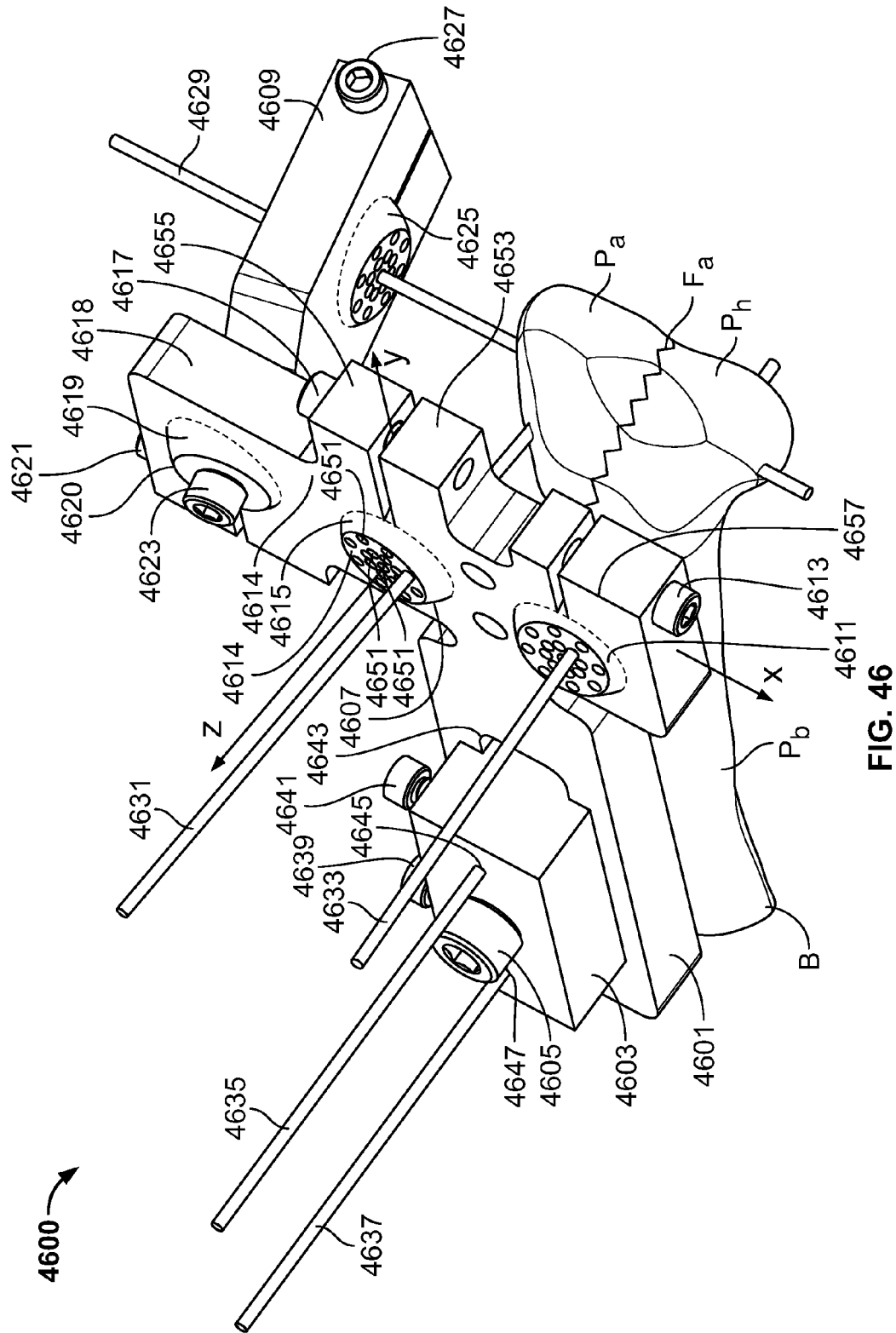
FIG. 46 shows yet other apparatus in accordance with the principles of the invention.

FIG. 46 shows illustrative apparatus 4600. Apparatus 4600 may include base 4601. Base 4601 may include channel 4643. Apparatus 4600 may include slider 4603. Slider may include receptacles 4647 and 4645. Receptacle 4643 may be configured to receive bone penetrating member 4637. Receptacle 4645 may be configured to receive bone penetrating member 4635. Bone penetrating members 4637 and 4635 may be secured to bone segment Pb. Bone penetrating members 4637 and 4635 may secured slider 4603 to bone segment Pb. Set screws 4639 and 4641 may fix an elevation of slider 4603 relative to bone segment Pb.

Within channel 4643, slider 4603 may be configured to translate relative to base 4601. Set screw 4605 may fix a position of slider 4603 relative to base 4601.

Apparatus 4600 may include collar 4607. Collar 4607 may include articulating surface 4615. Articulating surface 4615 may include a substantially spherically curvature. Collar 4607 may include planar surface 4614. Planar surface 4614 may include receptacles 4651. Receptacles 4651 may be configured to receive bone penetrating member 4631. Bone penetrating member 4633 may be secured to bone segment Pa.

Apparatus 4600 may be configured to position bone segment Pa along axes X, Y and Z. Apparatus 4600 may be configured to rotate bone segment Pa about axes X, Y and Z. Axis Z may be off-set from bone penetrating member 4631.

Apparatus 4600 may be configured to position bone segment Pa relative to a center of bone segment Pa. The center of bone segment Pa may correspond to origin O2 (shown in FIG. 7). Apparatus 4600 may be configured to position bone segment Pa relative to bone segment Pb. Apparatus 4600 may be configured to position bone segment Pa relative to bone segment Ph.

Apparatus 4600 may include collar support 4614. Articulating surface 4615 may articulate against collar support 4614. Collar support 4614 may include extensions 4653 and 4655. Set screw 4617 may be configured to compress extensions 4653 and 4655 about plane Z-Y. Compression of extensions 4653 and 4655 may apply pressure to articulating surface 4615. The pressure may fix a position of collar 4607 relative to collar support 4614. The pressure may fix a position of bone penetrating member 4631. The pressure may fix a position of bone segment Pa relative to origin O2.

Apparatus 4600 may include collar 4620. Collar 4620 may include articulating surface 4619. Articulating surface 4619 may have one or more features in common with articulating surface 4615. Collar 4620 may include extension 4609. Extension 4609 may have one or more features in common with collar support 4614. Extension 4609 may have one or more features in common with collar 4607. Extension 4609 may be configured to receive bone penetrating member 4629. Bone penetrating 4629 may be secured to bones segments Pa and Ph. Bone penetrating member 4629 may bridge fracture Fa.

Collar 4620 may be configured to fix a position of bone segments Pa and Ph relative to bone segment Pb. Set screw 4621 may fix a position of articulating surface 4619 relative to collar support 4618. Set screw 4627 may fix a position of articulating surface 4625 relative to extension 4609. Set screws 4621 and 4627 may fix a position of bone segments Pa and Ph relative to bone segment Pb.

Apparatus 4600 may include collar 4611. Collar 4611 may be configured to receive bone penetrating member 4633. Bone penetrating member 4633 may be secured to bone segment Ph. Collar 4611 may have one or more features in common with collar 4607. Collar 4611 may be configured to position bone segment Ph about origin O1 (shown in FIG. 7). Apparatus 4600 may include collar support 4657. Collar support 4657 may have one or more features in common with collar support 4614.

Set screw 4613 may be configured to fix a position of collar 4611 relative to collar support 4657. Set screw 4613 may be configured to fix a position of bone segment Ph relative to origin O1.

Figure 47:
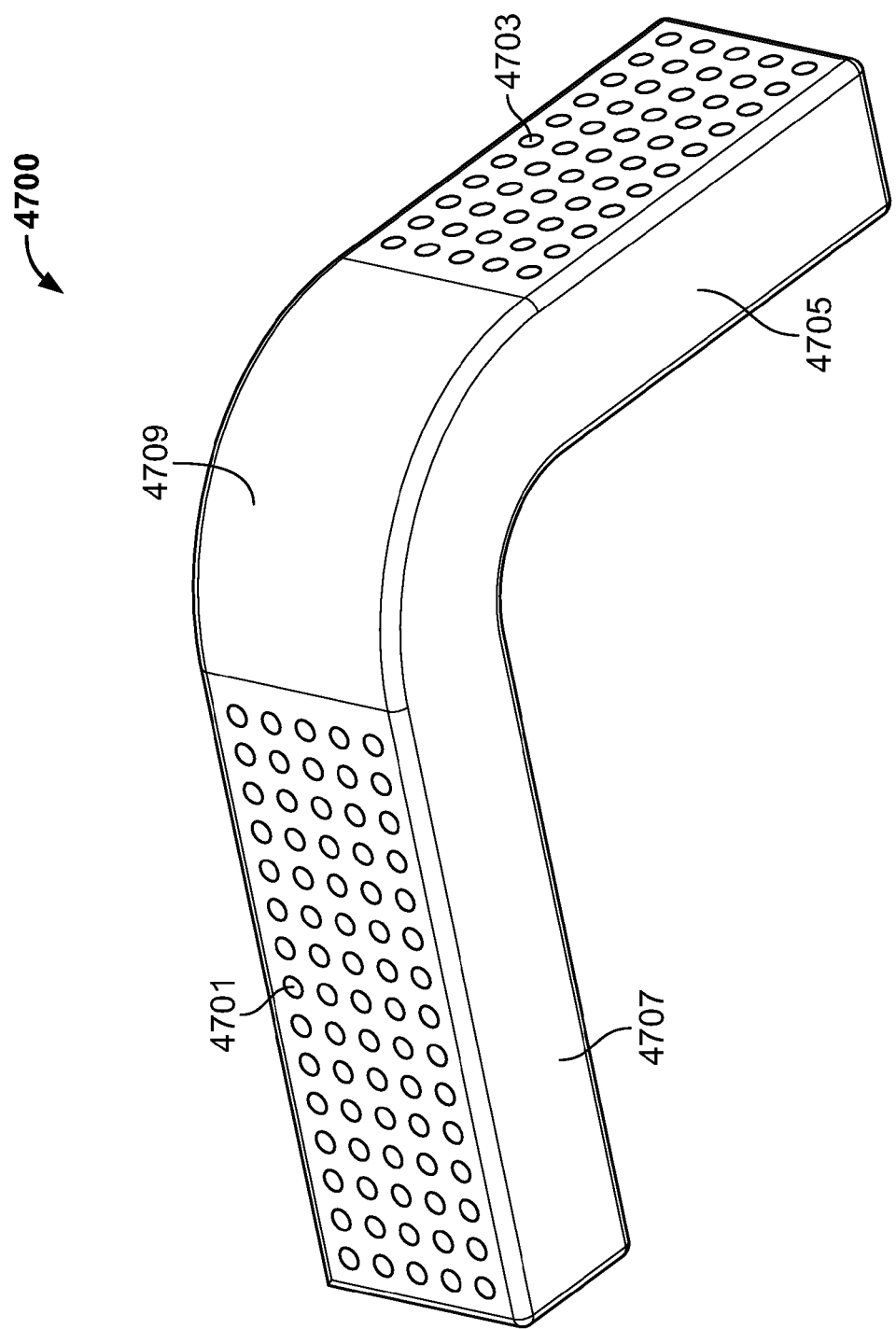
FIG. 47 shows yet other apparatus in accordance with the principles of the invention.

FIG. 47 shows illustrative apparatus 4700. Apparatus 4700 may include bridging member 4707. Bridging member 4707 may include receptacles 4701. Receptacles 4701 may be configured to receive a bone penetrating member. Receptacles 4701 may provide multiple positions for one or more bone penetrating members. Apparatus 4700 may include a pressure distribution member (see item 1013, FIG. 10). The pressure distribution member may be configured to fix a position of one or more bone penetrating members received by receptacles 4701.

Apparatus 4700 may include bridging member 4705. Bridging member 4705 may include receptacles 4703. Bridging member 4705 may have one or more features in common with bridging member 4707.

Support 4709 may join bridging member 4707 and bridging member 4705. Support 4709 may rigidly join bridging member 4707 and bridging member 4705. Support 4709 may include a hinge (not shown).

Figure 48A:
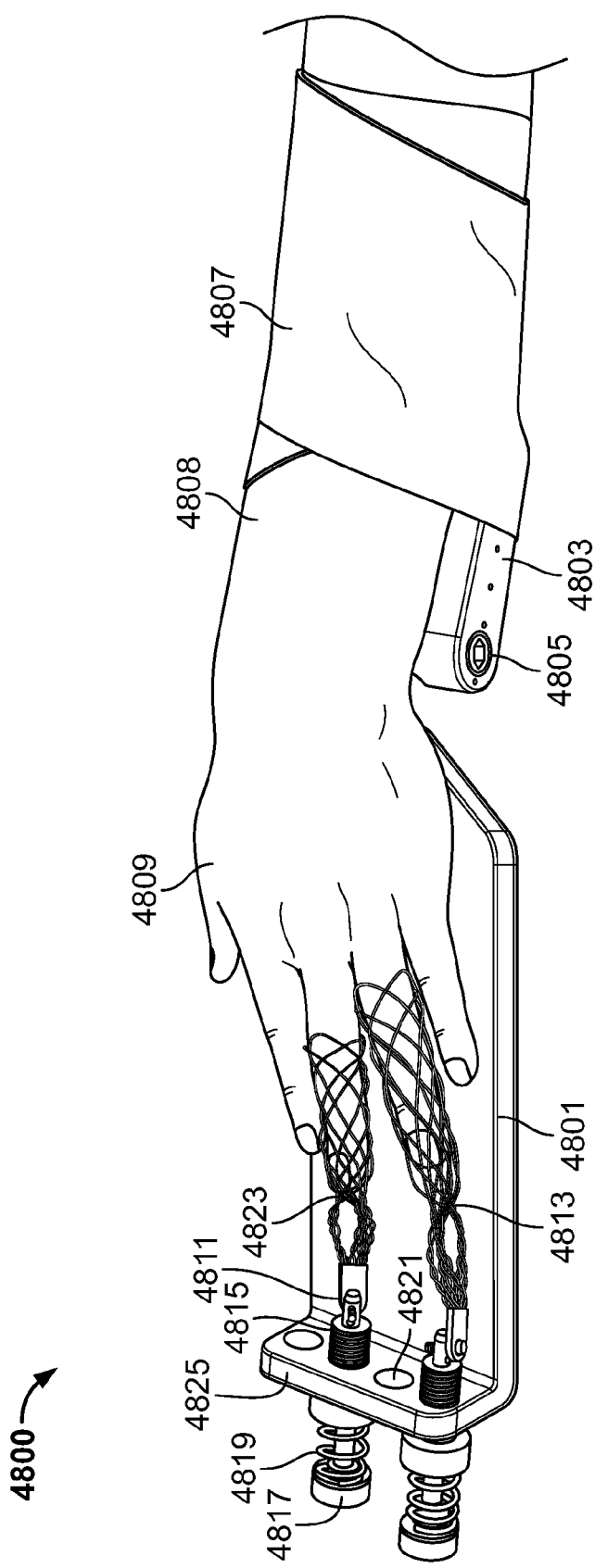
FIG. 48A shows yet other apparatus in accordance with the principles of the invention, along with anatomy.

FIG. 48A shows illustrative apparatus 4800. Apparatus 4800 may include support 4803. Support 4803 may be configured to support soft tissue 4808. Soft tissue 4808 may correspond to a first bone fragment (not shown).

Apparatus 4800 may include bracing element 4807. Bracing element 4807 may substantially fix a position of soft tissue 4808 relative to support 4803. Bracing element 4807 may substantially fix a position of the first bone segment relative to support 4803.

Apparatus 4800 may include support 4801. Support 4801 may be configured to support soft tissue 4809. Soft tissue 4809 may correspond to a second bone fragment (not shown).

Apparatus 4800 may include bracing element 4811. Bracing element 4811 may include soft tissue grasper 4823. Bracing element 4811 may include tensioning knob 4815. Bracing element 4811 may include spring 4819. Bracing element 4811 may include tensioner 4817.

Bracing element 4811 may be configured to apply tension to soft tissue 4809. The tension may displace the second bone fragment from the first bone fragment. Soft tissue grasper 4823 may be configured to apply increasing tension as displacement of the second bone fragment from the first bone fragment increases.

Bracing element 4811 may be configured to substantially fix a position of soft tissue 4809 relative to support 4801. Bracing element 48011 may substantially fix a position of the first bone segment relative to support 4803.

Apparatus 4800 may include bracing element 4813. Bracing element 4813 may have one or more features in common with bracing element 4811.

Apparatus 4800 may include support 4825. Support 4825 may include receptacle 4821. Receptacle 4821 may be configured to threadedly engage tensioning knob 4815. Threaded engagement of tensioning knob 4815 and receptacle 4821 may increase tension in spring 4819. Tension in spring 4821 may increase tension on tensioner 4817 and soft tissue grasper 4823. Increased tension on soft tissue grasper 4823 may increase traction to soft tissue 4809.

Apparatus 4800 may include set screw 4805. Set screw 4805 may be configured to fix a position of support 4803 relative to support 4801. Set screw 4805 may be configured to fix a position of the first bone fragment relative to the second bone fragment. Apparatus 4800 may be configured to reduce fractures Fa and Fh in bone B (shown in FIG. 3A).

Apparatus 4800 may reduce a fracture in bone B through application of forces applied in tension, translation, angle, and any suitable manipulation of bone segments of bone B relative to each other. Apparatus 4800 may be "self-contained" in that it may be secured directly only to the patient's body and to no other structure or support. Because apparatus 4800 may be self-contained, the clinician may freely manipulate apparatus 4800 to accommodate personal, clinical or therapeutic positioning requirements and preferences while maintaining reduction.

Figure 48B:
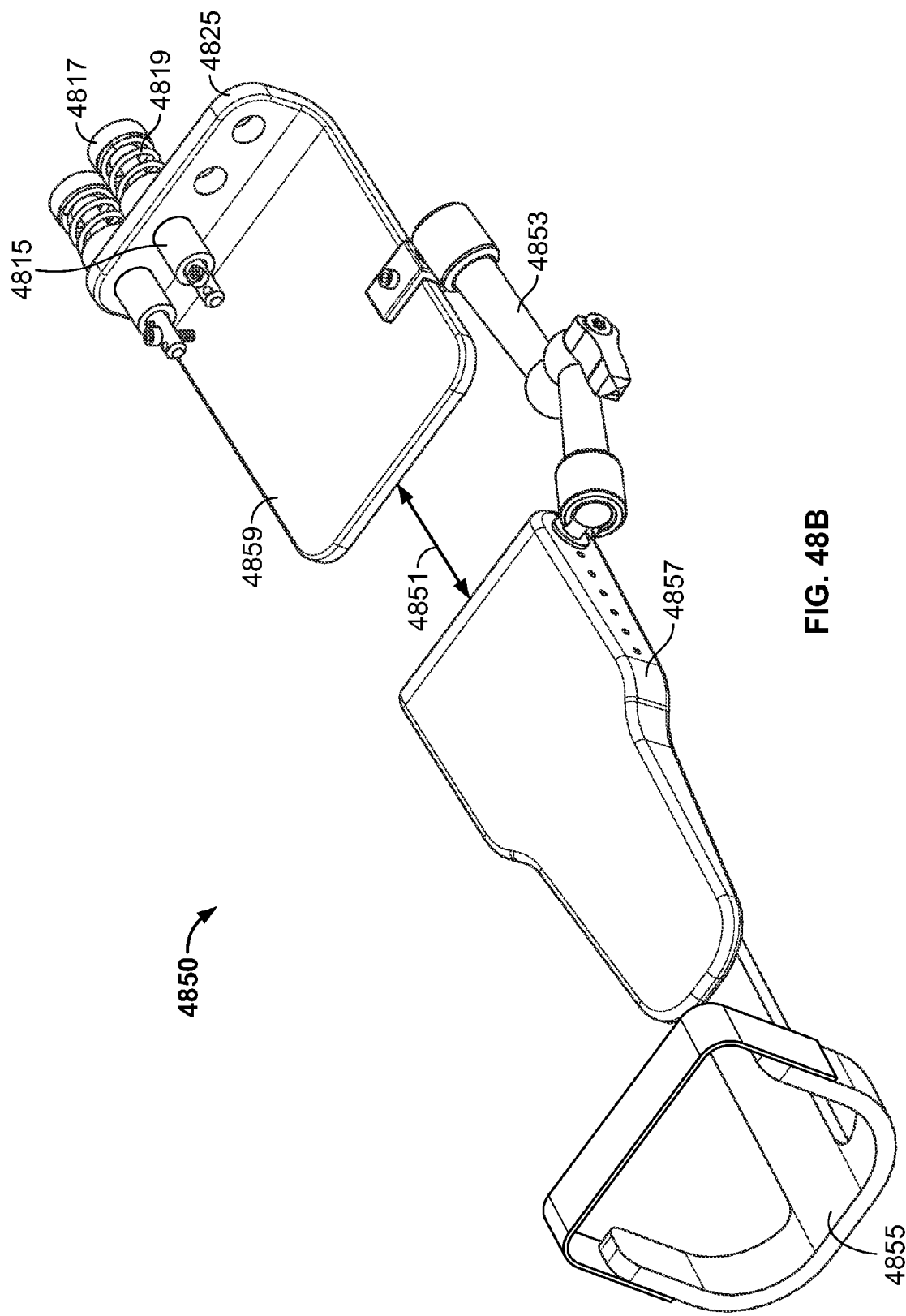
FIG. 48B shows yet other apparatus in accordance with the principles of the invention, along with anatomy.

FIG. 48B shows illustrative apparatus 4850. Elements of apparatus 4850 may have features in common with corresponding features of apparatus 4800 (shown in FIG. 48). For example, support 4857 may correspond to support 4801. Support 4859 may correspond to support 4803.

Apparatus 4850 may include brace 4855. Brace 4855 may secure soft tissue 4808 (shown in FIG. 48) against sliding relative to support 4857. Brace 4855 may secure soft tissue 4808 against sliding, for example, by providing resistance against an anterior region of the humerus.

Articulating lock 4853 may fix a position and orientation of support 4859 relative to support 4857. When lock 4853 is unlocked, gap 4851, between support 4857 and support 4859 may be lengthened or shortened.

For example, during a reduction procedure, supports 4857 and 4859 may be arranged in substantially the same plane. Gap 4851 may be lengthened to apply traction. Support 4859 may then be translated downward, while maintaining the attitude of support 4859. Support 4859 may then be tilted or rotated relative to support 4857. Lock 4853 may then be actuated to fix the position and orientation of support 4859 relative to support 4857.

Figure 49:
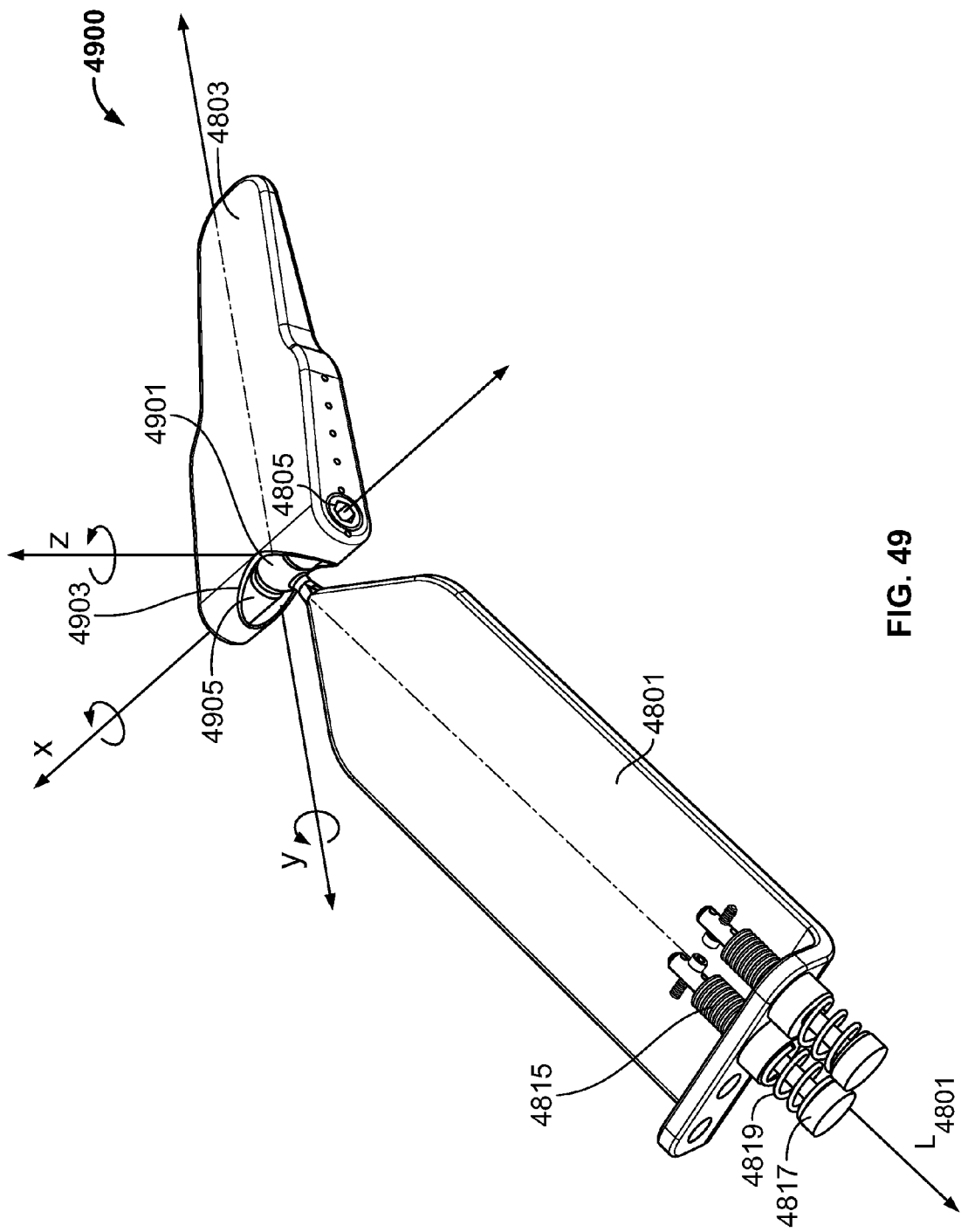
FIG. 49 shows the apparatus of FIG. 48A in a configuration that is different from that shown in FIG. 48A.

FIG. 49 shows illustrative apparatus 4900. Apparatus 4900 may have one or more features in common with apparatus 4800. Apparatus 4900 may include supports 4803 and 4801 (shown in FIG. 48). Apparatus 4900 may include ball joint 4901. Ball joint 4901 may be fixed to support 4801. Support 4805 may include a socket 4903. Socket 4903 may be configured to receive ball joint 4901. Ball joint 4901 may articulate against a portion of socket 4903.

Supports 4801 and 4803 may be configured to translate along axes X, Y and Z. Support 4801 and 4803 may be configured to rotate about axes X, Y and Z. Supports 4801 and 4803 may be positioned at an angle sigma. Angle sigma may correspond to a relative elevation of support 4801 relative to support 4803. Supports 4801 and 4803 may be positioned at an angle phi. Angle phi may correspond to a planar orientation, in plane X-Y, of support 4801 relative to support 4803.

Set screws 4805 4905 may threadedly engage base 4803. Set screws 4805 4905 may be configured to engage ball joint 4901. Set screws 4805 4905 may apply pressure to ball joint 4901. The pressure may fix a position of support 4801 relative to support 4803.

Figure 50:
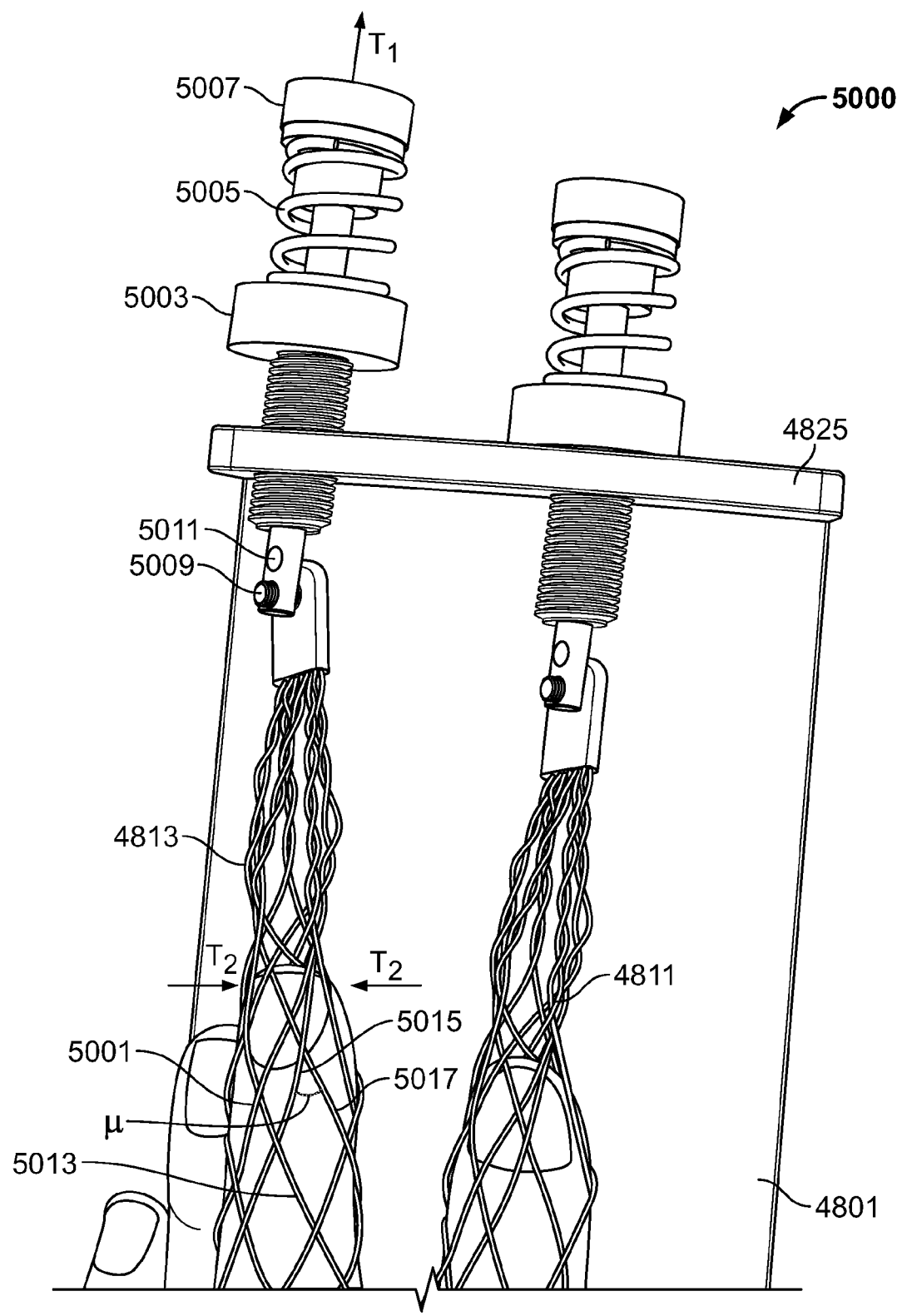
FIG. 50 shows a portion of the apparatus shown in FIG. 48A.

FIG. 50 shows a close-up view 5000 of a portion of apparatus 4800. View 5000 shows bracing element 4813. Bracing element 4813 may include web 5001. Web may include strands 5015 and 5017. Strands 5015 and 5017 may form angle mu.

Tensioning knob 5003 may be threadedly engagement with support 4825. Threaded engagement of tensioning knob 5003 and support 4825 may compress spring 5005 against tensioner 5007. The compression may induce tension in bracing element along axis T1. The tension and traction of soft tissue 5013 against web 5001 may decrease magnitude of angle mu.

Decreasing the magnitude of angle mu may increase a length of web 5001 along axis T1. Decreasing the magnitude of angle mu may compress web 5001 about lines T2-T2. Decreasing the magnitude of angle mu may increase traction of web 5001 against soft tissue 5013. Increased traction against soft tissue 5001 may fix a position of soft tissue 5013 relative to base 4801.

Tensioner 5007 may include receptacle 5011. Set screw 5009 may be configured to threadedly engage receptacle 5011. Set screw 5009 may fix a position of bracing element 4813 relative to tensioner 5007.

Figure 51:
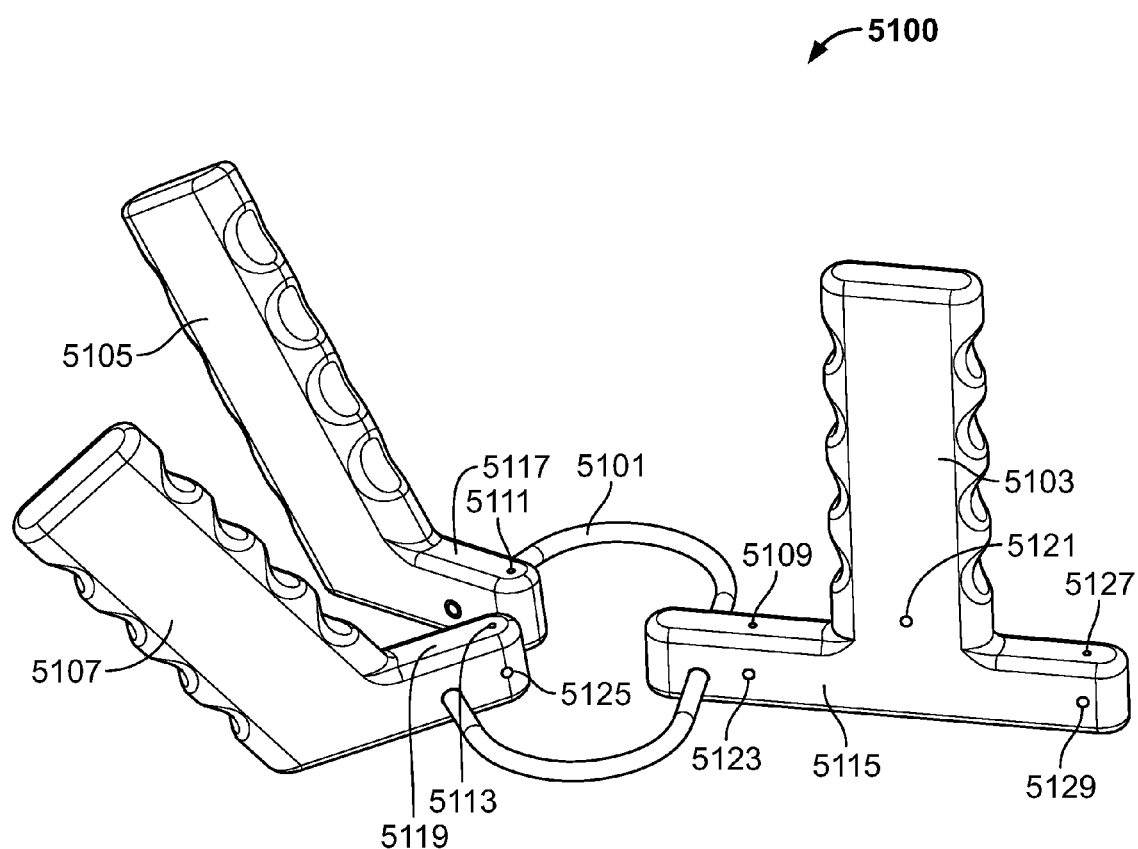
FIG. 51 shows yet other apparatus in accordance with the principles of the invention.

FIG. 51 shows illustrative apparatus 5100. Apparatus 5100 may include malleable frame 5101. Collars 5115, 5117 and 5119 may be fixed to malleable frame 5101.

Collar 5115 may include receptacles 5109 and 5123. Receptacle 5109 may be configured to receive a bone penetrating member. Receptacle 5123 may be configured to receive a set screw (not shown). Engagement of the set screw and receptacle may apply pressure to a bone penetrating member received by receptacle 5109. The pressure may fix a position of the bone penetrating member with respect to collar 5115.

Collar 5115 may include receptacle 5127. Receptacle 5127 may have one or more features in common with receptacle 5109. Collar 5115 may include receptacle 5129. Receptacle 5129 may have one or more features in common with receptacle 5123. Collar 5115 may be configured to be secured to one or more bone segments, such as bone segments Pa, Ph or Pb (shown in FIG. 3A).

Handle 5103 may position a bone segment secured to collar 5115 about a center of the bone segment. The center of the bone segment may correspond to origin O1 or O2 (shown in FIG. 7). Handle 5103 may position collar 5115 relative to collar 5117.

Apparatus 5100 may include release mechanism 5121. Release mechanism 5121 may be configured to release handle 5103 from collar 5115. Handle 5103 may be removable from collar 5115.

Collar 5117 may have one or more features in common with collar 5115. Collar 5117 may include receptacle 5111. Receptacle 5111 may be configured to receive a bone penetrating member. A bone penetrating member received by receptacle 5111 may be secured to a bone segment. A position of collar 5117 relative to the bone penetrating member may be fixed. Collar 5117 may be secured to a bone segment such as bone segments Pa, Ph or Pb (shown in FIG. 3A).

Handle 5101 may include one or more of the features of handle 5103. Handle 5101 may include a release mechanism. Handle 5105 may position a bone segment secured to collar 5117 about a center of the bone segment. The center of the bone segment may correspond to origin O1 or O2 (shown in FIG. 7). Handle 5105 may position collar 5117 relative to collar 5115. Handle 5101 may be removable from collar 5117.

Collar 5119 may include one or more of the features of collar 5115. Collar 5119 may include receptacle 5113. Receptacle 5113 may be configured to receive a bone penetrating member (not shown). A bone penetrating member received by receptacle 5113 may be secured to a bone segment. A position of collar 5119 relative to the bone penetrating member may be fixed. Collar 5119 may be secured to a bone segment such as bone segments Pa, Ph or Pb (shown in FIG. 3A).

Handle 5101 may include one or more of the features of handle 5103. Handle 5101 may include a release mechanism. Handle 5105 may position a bone segment secured to collar 5117 about a center of the bone segment. The center of the bone segment may correspond to origin O1 or O2 (shown in FIG. 7). Handle 5105 may position collar 5117 relative to collar 5115. Handle 5101 may be removable from collar 5117.

Malleable frame 5101 may be configured to retain a position of bone segments Pa and Ph relative to bone segment Pb. Apparatus 5100 may be configured to reduce a fracture in bone B. Apparatus 5100 may be configured to reduce fractures Fh and Fa in bone B (shown in FIG. 3A).

Figure 52:
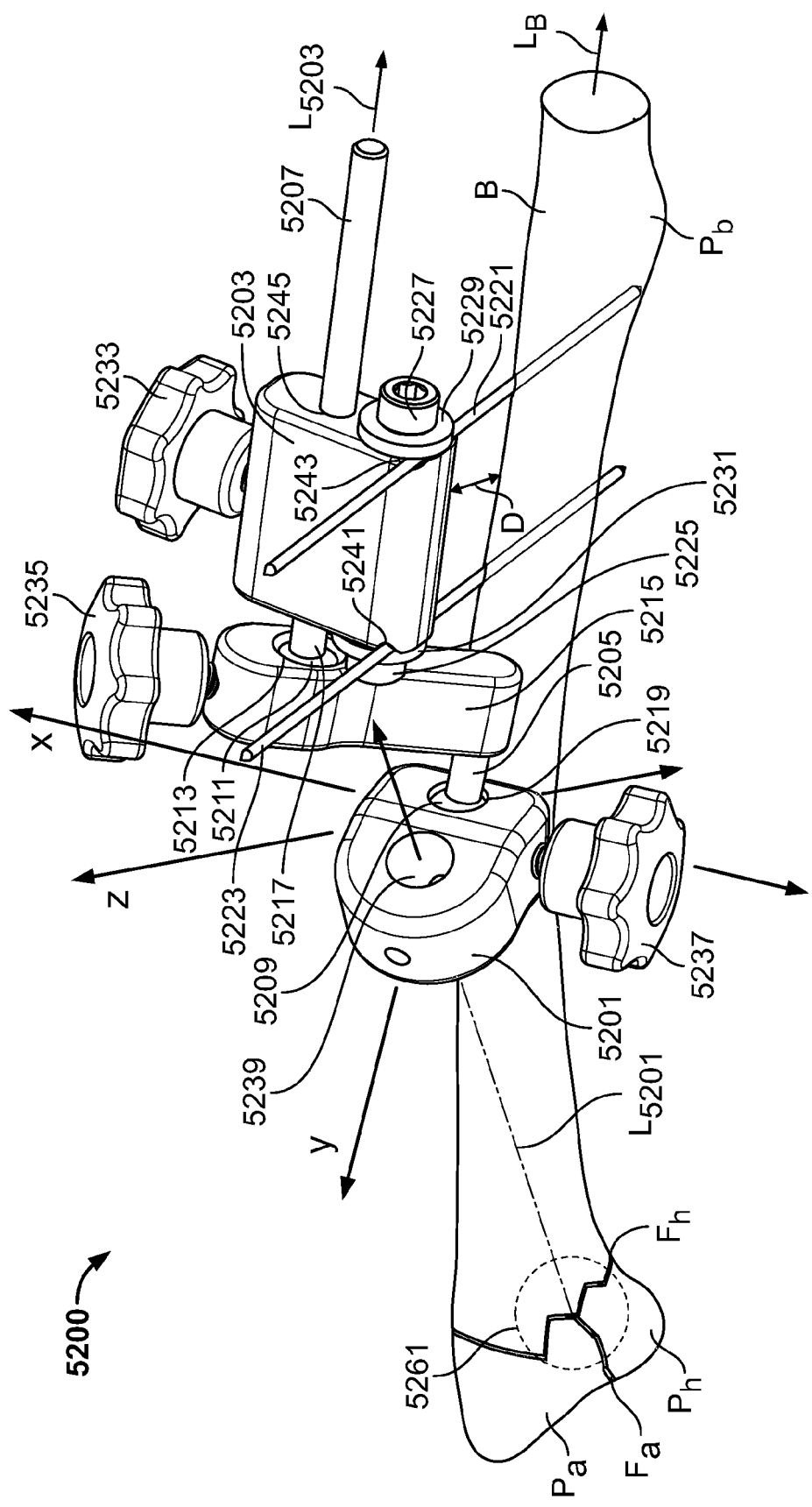
FIG. 52 shows yet other apparatus in accordance with the principles of the invention.

FIG. 52 shows illustrative apparatus 5200. Apparatus 5200 may include tool bracket 5201. Axes X, Y and Z may be three orthogonal axes.

Apparatus 5200 may include platform 5203. Platform 5203 may be positioned proximal to fractures Fa and Fh. Bone penetrating members 5223 and 5221 may be secured to bone B.

Bone penetrating member 5223 may pass alongside indent 5241 and washer 5231. Set screw 5225 may threadedly engage platform 5203. Threaded engagement of set screw 5225 and platform 5203 may press washer 5231 against platform 5203. Threaded engagement of set screw 5225 and platform 5203 may fix a position of platform 5203 relative to bone penetrating member 5223. Threaded engagement of set screw 5225 and platform 5203 may fix a position of platform 5203 relative to bone B.

Bone penetrating member 5221 may pass alongside indent 5243 and washer 5229. Set screw 5227 may threadedly engage platform 5203. Threaded engagement of set screw 5227 and platform 5203 may press washer 5229 against platform 5203. Threaded engagement of set screw 5227 and platform 5203 may fix a position of platform 5203 relative to bone penetrating member 5221. Threaded engagement of set screw 5227 and platform 5203 may fix a position of platform 5203 relative to bone B.

Threaded engagement of set screws 5227 and 5225 with platform 5203 may secure platform 5203 to bone B. Threaded engagement of set screws 5227 and 5225 with platform 4203 may fix distance D. Distance D may correspond to a position of platform 5203 relative to bone B.

Apparatus 5200 may include housing 5215. Rod 5205 may extend from housing 5215 to ball joint 5209. Ball joint 5209 may be configured to articulate against socket 5219 of tool bracket 5201. Articulation of ball joint 5209 against socket 5219 may provide tool bracket 5201 freedom to translate along and rotate about three orthogonal axes, such as axes X, Y and Z.

Knob 5237 may threadedly engage tool bracket 5201. Threaded engagement of knob 5237 and tool bracket 5201 may apply pressure to ball joint 5209. The pressure may fix a position of tool bracket 5201 along or about three orthogonal axes. The pressure may limit displacement of tool bracket 5201 relative to bone B.

Rod 5217 may extend from ball joint 5211 through bore 5245 in platform 5203. Ball joint 5211 may be configured to articulate against socket 5213 of housing 5215. Articulation of ball joint 5211 against socket 5213 may provide housing 5201 freedom to translate along and rotate about three orthogonal axes. Articulation of ball joint 5211 against socket 5213 may provide tool bracket 5201 freedom to translate along and rotate about three orthogonal axes, such as axes X, Y and Z.

Knob 5235 may threadedly engage housing 5215. Threaded engagement of knob 5235 and housing 5215 may apply pressure to ball joint 5211. The pressure may fix a position of housing 5215 along or about three orthogonal axes. The pressure may limit displacement of tool bracket 5201 relative to bone B.

Housing 5215 may be translatable, relative to platform 5203, along axis L5203. Housing 5215 may be translatable, relative to bone B, along axis L5203. Knob 5233 may be configured to threadedly engage platform 5203. Threaded engagement of knob 5233 and platform 5203 may apply pressure to rod 5217. The pressure may fix a position of housing 5215 along axis L5203. The pressure may limit displacement of tool bracket 5201 relative to bone B.

Pressure applied by knobs 5237, 5235 and 5233 may fix a position of tool bracket 5201 relative to bone B. Tool bracket 5201 may be fixed outside bone B relative to site 5261 interior to bone B. Tool bracket 5201 may include cannula 5239. Center axis L5201 of cannula 5239 may be aligned to correspond to an axis of site 5261. A position of tool bracket 5201 may be fixed such that axis L5201 corresponds to an axis of site 5261.

Figure 53:
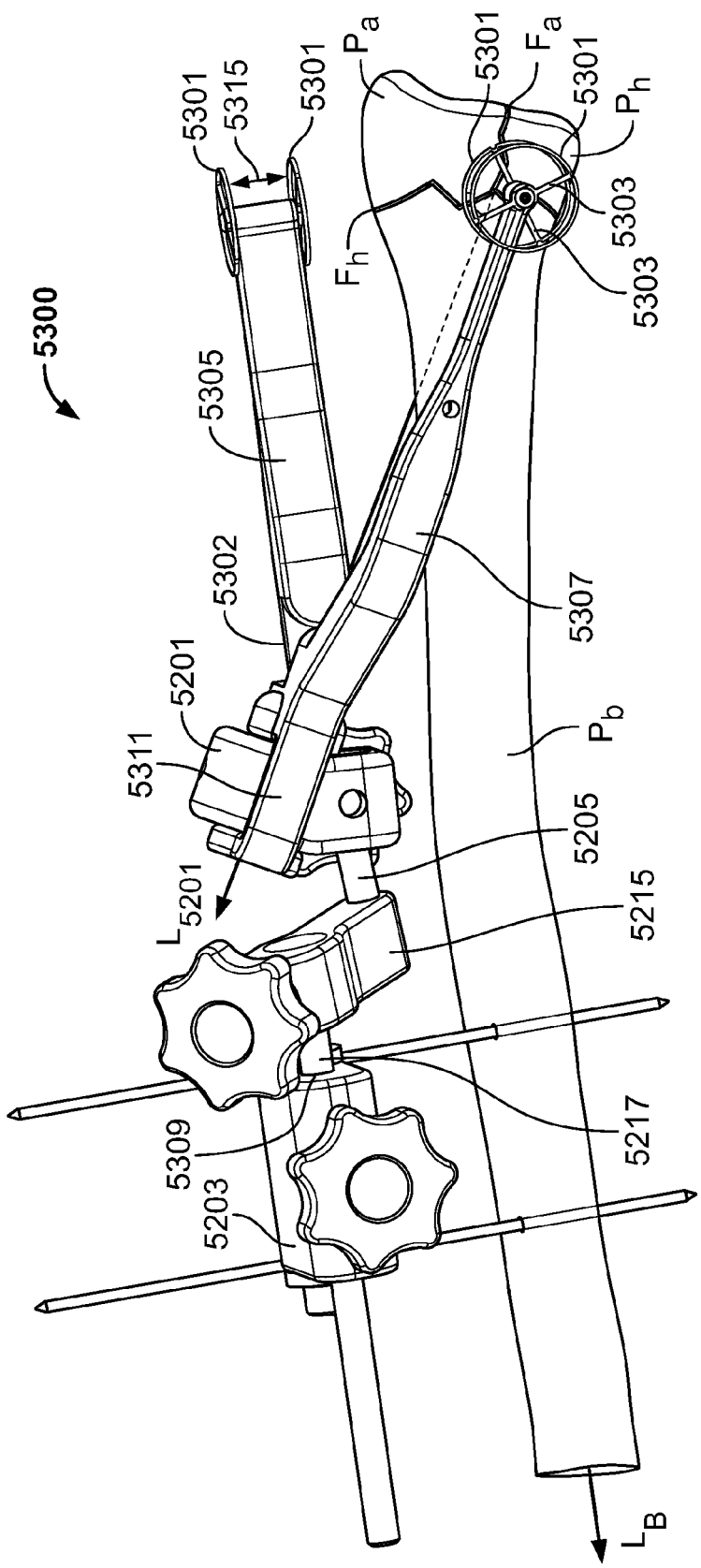
FIG. 53 shows a portion of the apparatus shown in FIG. 52, along with anatomy.

FIG. 53 shows illustrative apparatus 5300. Apparatus 5300 may have one or more features in common with apparatus 5200. Apparatus 5300 may include radiopaque target 5302. Radiopaque target 5302 may be configured to attach to tool bracket 5201. Seat 5311 may be configured to attach radiopaque target 5302 to tool bracket 5201.

Radiopaque target 5302 may be configured to be removable from tool bracket 5201.

Radiopaque target 5302 may include extension 5305. Extension 5305 may include targets 5301. Targets 5301 may include spokes 5303. Targets 5301 may be separated by distance 5315. Spokes 5303 and distance 5315 may be configured to reduce parallax error when targeting a site, such as site 5261 (shown in FIG. 52), interior to bone B.

Radiopaque target 5302 may include extension 5307. Extension 5307 may include targets 5301. Extension 5305 may be positioned substantially parallel to a first anatomical viewing plane, such as plane 200 or 202 (shown in FIG. 2B). Extension 5307 may be positioned substantially parallel to a second anatomical viewing plane, such as plane 200 or 202 (shown in FIG. 2B). Extensions 5307 and be positioned in substantially orthogonal planes. Extension 5305 may be adjusted relative to extension 5307.

Displacement of tool bracket 5201 along and about axes X, Y and Z (shown in FIG. 52) may position targets 5301 relative to bone B. Medical imaging may be used to position targets 5301 relative to site 5261 interior to bone B. Seat 5311 may be configured such that positioning of targets 5301 relative to site 5261 positions tool bracket 5201 relative to site 5261. Seat 5311 may be configured such that positioning of targets 5301 relative to site 5261 positions tool bracket 5201 relative to center-line Lb (shown in FIG. 3A) of bone B.

Positioning targets 5301 relative to site 5261 may position tool bracket 5201 relative to site 5261 (shown in FIG. 52). Site 5261 may be interior to bone B. Positioning targets 5301 relative to site 5261 may register tool bracket 5201 to site 5261. Registering tool bracket 5201 to site 5261 may include aligning axis L5201 with an axis of the site. After registering tool bracket 5201 to site 5261, knobs 5237, 5235 and 5233 may be configured to lock a position of tool bracket 5201 relative to site 5261.

Figure 54:
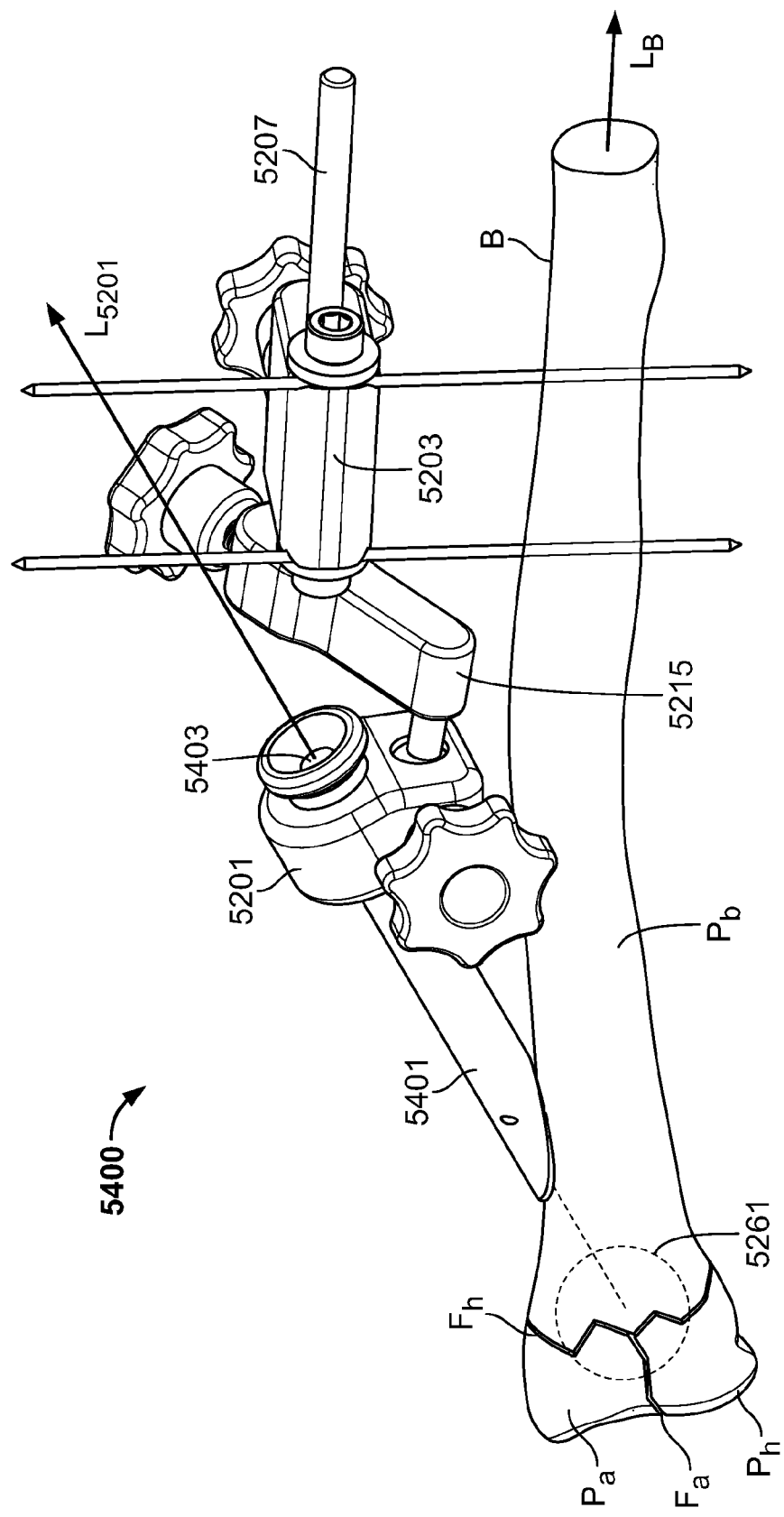
FIG. 54 shows a portion of the apparatus shown in FIG. 52, along with anatomy.

FIG. 54 shows illustrative apparatus 5400. Apparatus 5400 may have one or more features in common with apparatus 5200.

Apparatus 5400 may include guide tube 5401. Guide tube 5401 may be configured to attach to tool bracket 5201. Guide tube 5401 may be configured to be removed from tool bracket 5201. Guide tube 5401 may be inserted into cannula 5239.

Radiopaque target 5302 may be configured to position tool bracket 5201 such that guide tube 5401, when inserted into cannula 5239, is configured to guide a surgical tool to site 5261. The surgical tool may be a rotary surgical tool (not shown). Cannula 5403 may guide the surgical tool. Cannula 5403 may be configured to guide the surgical tool along axis L5201.

Figure 55:
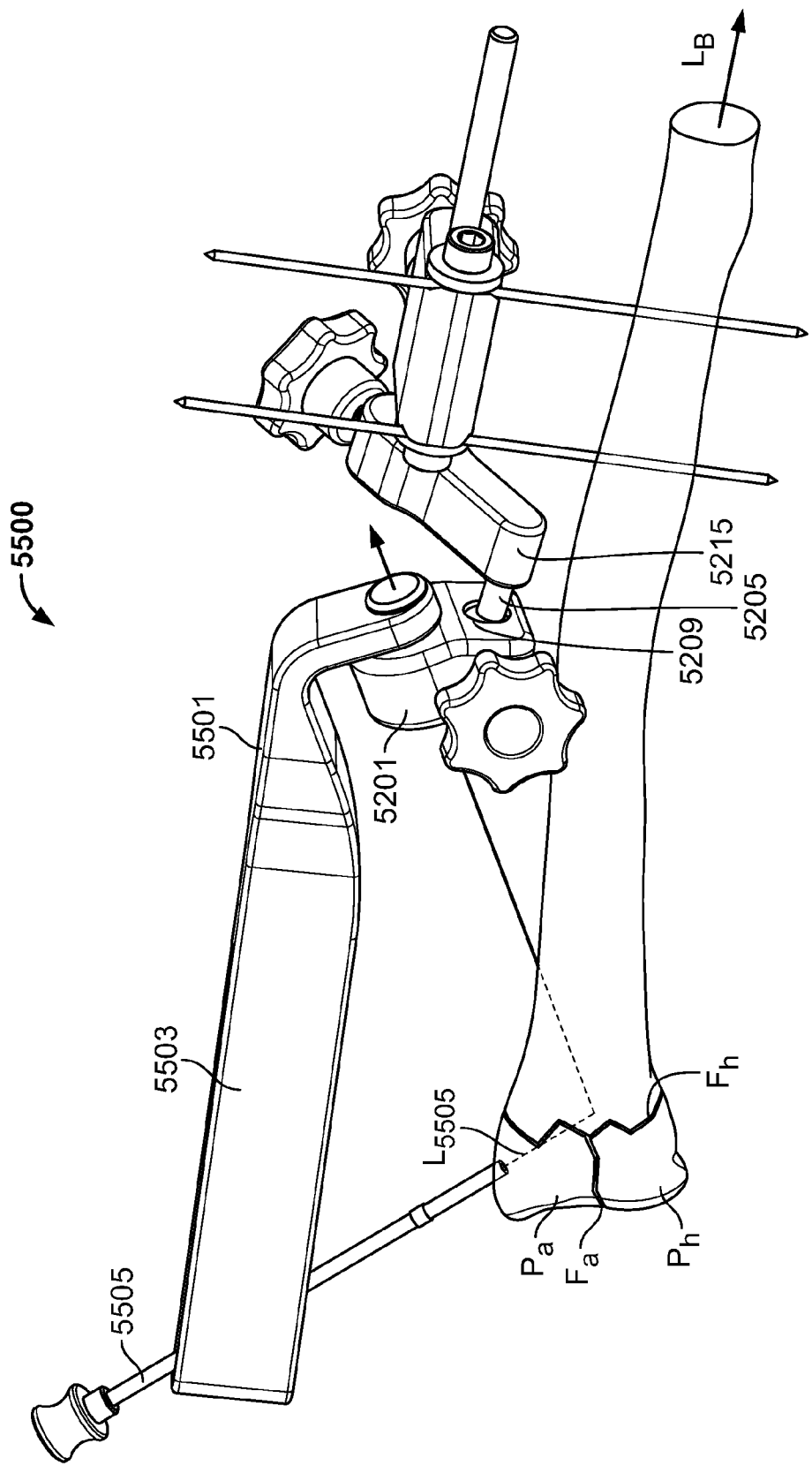
FIG. 55 shows a portion of the apparatus shown in FIG. 52, along with anatomy.

FIG. 55 shows illustrative apparatus 5500. Apparatus 5500 may have one or more features in common with apparatus 5200.

Apparatus 5500 may include fixture 5501 fixture 5501 may be attached to tool bracket 5201. Fixture 5501 may include guide passageway 5503. Guide passageway 5503 may be configured receive wire support 5505. Wire support 5505 may be configured to receive a bone penetrating element such as anchors 329 or 326 (shown in FIG. 3B). The bone penetrating element may be secured to a bone segment, such as bone segments Pa or Ph.

Radiopaque target 5302 may be configured to position tool bracket 5201 such that guide passageway, when attached to tool bracket 5201, is oriented relative to site 5261. Radiopaque target 5302 may be configured to position tool bracket 5201 such that guide passageway 5503, when attached to tool bracket 5201, is oriented relative to center-line LB (shown in FIG. 3A) of bone B.

When attached to tool bracket 5201, guide passageway 5503 may be aligned with an axis of site 5261 (shown in FIG. 52). When attached to tool bracket 5201, guide passageway 5503 may direct a bone penetrating member received by wire support 5505 into bone segment Pa. The bone penetrating member received by wire support 5505 may be secured to implant 300 (shown in FIG. 3B). Implant 300 may be deployed at site 5261 (shown in FIG. 52). The bone penetrating member received by wire support 5505 may secure bone segment Pa to implant 300.

Table 3 lists illustrative steps that may be taken for therapeutic use of the apparatus.

TABLE 3

Illustrative steps that may be taken for therapeutic use of the apparatus

| Illustrative FIG. | Illustrative Steps and Illustrative Reference Numerals |
|---|---|
| 10, 11, 12A, 12B, 12C | 1. Reduce and stabilize bone (employing one or both of subchondral and transfracture k-wires, as appropriate).<br>2. Place k-wire 1001 in distal end of dorsal ulnar radius.<br>3. Place jig on k-wire and center base along radius.<br>4. Insert styloid k-wire 1007.<br>5. Center jig on radius (restore radial inclination).<br>6. Insert radius k-wire 1023.<br>7. Lock k-wires.<br>8. Restore radial height.<br>9. Restore volar tilt. |
| 13, 26 | 1. Place bone penetrating members into fracture fragments, 1314 and 1315.<br>2. Place 1311 in radius or unfractured bone section.<br>3. Manipulate 1314 and 1315 so that bone fragments are positioned into desired locations.<br>4. Lock position using feature 1329<br>5. Adjust relative position of fragments using adjustment of member 1307, 1305. |
| 29, 28, 30 | 1. Position k-wire into desired location of distal tip of the implant. Usually centered under the lunate facet.<br>2. Apply jig onto k-wire engagement feature 2815.<br>3. Swing down jig until it comes into contact with the bone.<br>4. Drill into bone at location identified in step 3. |

TABLE 3-continued

Illustrative steps that may be taken for therapeutic use of the apparatus

| Illustrative FIG. | Illustrative Steps and Illustrative Reference Numerals |
|---|---|
| 32, 33 | 1. Position k-wire into desired location of distal tip of the implant. Usually centered under the lunate facet. Drill into bone until shoulder of wire rests on surface of bone.<br>2. Apply jig onto k-wire engagement feature 3309. Bring jig down onto shoulder of k-wire.<br>3. Swing down jig until it comes into contact with the bone, extend length of arc as necessary to contact bone in desired location.<br>4. Drill into bone at location identified in step 3. |
| 36 | 1. Place wire under subchondral surface entering at the radial Styloid centered in the dorsal palmer aspect.<br>2. Place jig over wire.<br>3. Swing jig down onto bone.<br>4. Place toe nail wires securing the jig onto the bone.<br>5. Use drill guide tube to direct access into bone cavity. |
| 37 | 1. Position k-wire into desired location of distal tip of the implant. Usually centered under the lunate facet.<br>2. Apply jig onto k-wire engagement feature 3724.<br>3. Swing down jig until it comes into contact with the bone.<br>4. Slide up and down wire as necessary to contact bone in desired location.<br>5. Place toe nail wires securing the jig onto the bone.<br>6. Use drill guide tube to direct access into bone cavity. |
| 38, 39, 40 | 1. Apply k-wires through distal hole locations into the bone fracture segments. Position these wires such that the member 3809 is centered on the bone in the position of the center of the implant.<br>2. Apply k-wires on proximal aspect of jig 3833 and 3835 into the long bone section of the radius.<br>3. Adjust height of the height of the broken segments with member 3839.<br>4. Adjust volar tilt of fragments using member 3837.<br>5. Adjust radial inclination using member 3831.<br>6. When bone is in desired position mount arm 3811 onto base jig and swing down onto bone in desired position.<br>7. Secure jig to bone using 3843 k-wire toe nail features.<br>8. Adjust drill tube angle to be parallel with bone axis using feature 3821 and 3817.<br>9. Access bone cavity through guide tube 3847. |
| 37, 38 | 1. Position radiopaque targets into desired implant location.<br>2. Apply jig until it comes into contact with the bone.<br>3. Place toe nail wires securing the jig onto the bone.<br>4. Use drill guide tube to direct access into bone cavity. |
| 41 | 1. Place bone penetrating members into fracture fragments, through 4211.<br>2. Place k-wires through 4107, 4109 in reference bone fragment.<br>3. Manipulate 4139 and 4110 so that bone fragments are positioned into desired locations.<br>4. Lock position using feature 4213, 4115, 4121.<br>5. Adjust relative position of fragments using adjustment of member 4102.<br>6. Position 4149 in to desired location of implant.<br>7. Attach swing arm onto 4149 and follow similar steps as above. |
| 46 | 1. Place bone penetrating members into fracture fragments, through 4613, 4614, 4625.<br>2. Place k-wires through 4645, 4647 in radius or unfractured bone section.<br>3. Manipulate 4633, 4631 so that bone fragments are positioned into desired locations.<br>4. Lock position using feature 4613, 4627, 4617.<br>5. Adjust relative position of fragments using adjustment of member 4605. |
| 48 | 1. Place broken wrist over member 4805 on jig.<br>2. Place fingers into traps. |
| | 3. Attach forearm to jig 4803 with some member 4807 such as coban or ace bandage.<br>4. Apply tension to fingers using 4817.<br>5. Position angle of jig using 4805 such that the wrist is put into extension and flexion. |
| 51 | 1. Place bone penetrating members into fracture fragments, through 5113 5111<br>2. Place k-wires through 5129 in radius or unfractured bone section.<br>3. Manipulate 5107, 5125 so that bone fragments are positioned into desired locations. |

There are numerous other steps that may be included. Different embodiments of the apparatus shown and described herein may be used in conjunction with different steps of methods of the invention, whether or not listed in Table 4.

Thus, apparatus and methods for preparing a fractured bone for repair. Persons skilled in the art will appreciate that the present invention can be practiced by other than the described embodiments, which are presented for purposes of illustration rather than of limitation.

The present invention is limited only by the claims that follow.

What is claimed is:

1. Apparatus for reducing a fracture of a bone, the apparatus comprising:
   a bridging member that defines a first receptacle and a second receptacle, the bridging member spanning from the first receptacle to the second receptacle;
   a channel within the bridging member;
   a pressure distribution member that is slidable in the channel between an unlock position and a lock position; and
   a base rigidly affixed to the bridging member, the base comprising a collar that defines a third receptacle;
   wherein:
   the first receptacle is configured to receive a first bone penetrating element at a position, operatively external to the bone, on the first bone penetrating element;
   the second receptacle is configured to receive a second bone penetrating element at a position, operatively external to the bone, on the second bone penetrating element;
   the third receptacle is configured to receive a third bone penetrating element at a position, operatively external to the bone, on the third bone penetrating element;
   in the unlock position, the bridging member is moveable relative to the first and the second bone penetrating elements, and
   in the lock position;
   the pressure distribution member is configured to fix the bridging member relative to the first and the second bone penetrating elements; and,
   the base is configured to move along the third bone penetrating element and bend the third bone penetrating element along a length of the third bone penetrating element, the length extending between the bone and the base.

2. The apparatus of claim 1, wherein, the base is configured to move along the third bone penetrating element and adjust an angle of the first bone penetrating element relative to a segment of the third bone penetrating element.

3. The apparatus of claim 2 wherein, the length of the third bone penetrating element is a first length;
the base is configured to bend the third bone penetrating element along the first length; and
the collar is configured to maintain a second length of the third bone penetrating element substantially parallel to the first and the second bone penetrating elements.

4. The apparatus of claim 1 wherein:
the first receptacle comprises a first pass-through and a second pass-through; and
the second receptacle comprises a first pass-through and a second pass-through;
wherein the first pass-throughs are spaced apart from the second pass-throughs by a depth of the channel.

5. The apparatus of claim 1 wherein the pressure distribution member is configured to slide within the channel from the unlock position to the lock position and simultaneously apply pressure to:
the first bone penetrating element when the first bone penetrating element is within the first receptacle; and
the second penetrating element when the second bone penetrating element is within the second receptacle.

6. The apparatus of claim 1 further comprising a set screw that is configured to maintain the pressure distribution member in the lock position.

7. The apparatus of claim 1 wherein the pressure distribution member defines a first pass-through that corresponds to the first receptacle and defines a second pass-through that corresponds to the second receptacle.

8. The apparatus of claim 7 wherein:
the first pass-through of the pressure distribution member comprises a wide end that has a diameter greater than or equal to a diameter of the first receptacle; and
the second pass-through of the pressure distribution member comprises a wide end that has a diameter greater than or equal to a diameter of the second receptacle.

9. The apparatus of claim 7 wherein:
the first pass-through of the pressure distribution member comprises a narrow end that has a diameter less than the diameter of the first receptacle; and
the second pass-through of the pressure distribution member comprises a narrow end that has a diameter less than the diameter of the second receptacle.

10. The apparatus of claim 9 wherein, in the unlock position:
the wide end of the first pass-through of the pressure distribution member is aligned with the first receptacle; and
the wide end of the second pass-through of the pressure distribution member is aligned with the second receptacle.

11. The apparatus of claim 10 wherein:
the first bone penetrating element defines a first longitudinal axis;
the second bone penetrating element defines a second longitudinal axis; and,
in the unlock position, the first bone penetrating element is moveable along the first longitudinal axis and the second bone penetrating element is moveable along the second longitudinal axis.

12. The apparatus of claim 11 wherein, in the unlock position, the first bone penetrating element is rotatable about the first longitudinal axis and the second bone penetrating element is rotatable about the second longitudinal axis.

13. The apparatus of claim 12 wherein, in the lock position, the pressure distribution member is configured to fix each of the first and second bone penetrating elements longitudinally and rotationally relative to the bridging member.

14. The apparatus of claim 9 wherein, in the lock position:
the narrow end of the first pass-through of the pressure distribution member is configured to apply pressure to the first bone penetrating element in the first receptacle; and
the narrow end of the second pass-through of the pressure distribution member is configured to apply pressure to the second bone penetrating element in the second receptacle.

15. The apparatus of claim 14 wherein, the pressure applied to the first and the second bone penetrating elements is configured to fix the first and the second bone penetrating elements relative to the bridging member.

16. The apparatus of claim 1 wherein, the channel is a first channel, the apparatus further comprising a second channel and the collar is slidably mounted in the second channel.

17. The apparatus of claim 16 further comprising a length lock configured to fix a position of the collar along the second channel.

18. The apparatus of claim 1 further comprising an elevation lock configured to fix the base along the third bone penetrating element.

19. The apparatus of claim 18, the base further comprising a third channel and the elevation lock is configured to slide in the third channel in response to movement of the collar in the second channel.

20. The apparatus of claim 1 further comprising a support that rigidly fixes the base to the bridging member.

21. The apparatus of claim 20 wherein the support defines a recess that is configured to provide unobstructed imaging of the fracture.

22. Apparatus for reducing a fracture of a bone, the bone comprising a first segment, a second segment and a third segment, the apparatus comprising:
a bridging member:
defining a first receptacle that is configured to receive a first bone penetrating element at a position, operatively external to the first segment, on the first bone penetrating element when the first bone penetrating element is inserted into the first segment;
defining a second receptacle that is configured to receive a second bone penetrating element at a position, operatively external to the second segment, on the second bone penetrating element when the second bone penetrating element is inserted into the second segment; and
comprising a pressure source that is configured to fix a position of the bridging member relative to the first and the second bone penetrating elements;
a base rigidly joined to the bridging member, the base comprising a channel extending along a longitudinal axis of the base;
a collar that is slidable in the channel, the collar defining a third receptacle that is configured to receive a third bone penetrating element at a first position, operatively external to the third segment, on the third bone penetrating element when the third bone penetrating element is inserted into the third segment; and
a length lock that is configured to fix a position of the collar along the channel;
wherein, in operation, when the bridging member is fixed with respect to the first and the second bone penetrating elements and the collar is fixed at the position along the channel, the collar is configured to move along the third bone penetrating element and bend the third bone penetrating element at a second position, operatively external to the third segment, on the third bone penetrating element.

23. The apparatus of claim 22 wherein the channel is a first channel, the base comprising:
   a second channel that extends along the longitudinal axis and is substantially perpendicular to the first channel; and
   an elevation lock that is configured to:
      slide in the second channel when the collar slides in the first channel; and
      fix a position of the collar on the third bone penetrating element.

24. The apparatus of claim 22 wherein the length lock comprises a set screw that is in mechanical communication with the collar, and rotation of the set screw is configured to move the collar along the first channel.

25. The apparatus of claim 22, wherein, the bone is a first bone, a support that rigidly joins the base to the bridging member defines a fourth receptacle that is configured to:
   receive a fourth bone penetrating element; and
   direct the fourth bone penetrating element into a second bone.

26. The apparatus of claim 25 wherein the first bone is a radius and the second bone is an ulna.

\* \* \* \* \*

UNITED STATES PATENT AND TRADEMARK OFFICE
CERTIFICATE OF CORRECTION

PATENT NO. : 9,968,478 B2
APPLICATION NO. : 15/056918
DATED : May 15, 2018
INVENTOR(S) : Kyle Taylor et al.

It is certified that error appears in the above-identified patent and that said Letters Patent is hereby corrected as shown below:

On the Title Page

Item (63), replace "Continuation" with --Divisional--.

Signed and Sealed this
Sixteenth Day of October, 2018

Andrei Iancu
*Director of the United States Patent and Trademark Office*